US006878704B2

(12) United States Patent
Aitken et al.

(10) Patent No.: US 6,878,704 B2
(45) Date of Patent: Apr. 12, 2005

(54) HETEROCYCLIC MUTILIN ESTERS AND THEIR USE AS ANTIBACTERIALS

(75) Inventors: Steven Aitken, Harlow (GB); Gerald Brooks, Harlow (GB); Steven Dabbs, Harlow (GB); Colin Henry Frydrych, Harlow (GB); Steven Howard, Cambridge (GB); Eric Hunt, Harlow (GB)

(73) Assignee: SmithKline Beecham p.l.c., Brentford (GB)

( * ) Notice: Subject to any disclaimer, the term of this patent is extended or adjusted under 35 U.S.C. 154(b) by 0 days.

(21) Appl. No.: 10/343,596

(22) PCT Filed: Aug. 2, 2001

(86) PCT No.: PCT/EP01/08949

§ 371 (c)(1), (2), (4) Date: Oct. 17, 2003

(87) PCT Pub. No.: WO02/12199

PCT Pub. Date: Feb. 14, 2002

(65) Prior Publication Data

US 2004/0058937 A1 Mar. 25, 2004

(30) Foreign Application Priority Data

Aug. 3, 2000 (GB) ............................................ 0018951

(51) Int. Cl.$^7$ ....................... C07D 213/02; A61K 31/44

(52) U.S. Cl. ................................ 514/231.2; 514/252.1; 514/258; 514/350; 514/354; 514/356; 546/301; 546/326; 544/106; 544/250; 544/251; 544/336

(58) Field of Search ................................ 546/326, 301; 514/354, 356, 252.1, 258, 350, 231.2; 544/106, 250, 251, 336

(56) References Cited

FOREIGN PATENT DOCUMENTS

| | | | |
|---|---|---|---|
| WO | WO 97/25309 | 7/1997 | |
| WO | WO 00/07974 | 2/2000 | |
| WO | WO 00/27790 | * 5/2000 | ......... C07C/69/013 |
| WO | WO 00/37074 | 6/2000 | |
| WO | WO 00/73287 | 12/2000 | |

* cited by examiner

*Primary Examiner*—Zinna Northington Davis
(74) *Attorney, Agent, or Firm*—Linda E. Hall; Stephen Venetianer; Charles M. Kinzig

(57) ABSTRACT

Pleuromutilin compounds of the formula:

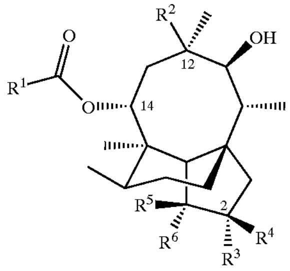

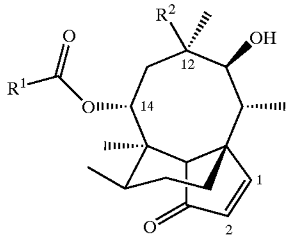

are of use in anti-bacterial therapy.

20 Claims, No Drawings

HETEROCYCLIC MUTILIN ESTERS AND THEIR USE AS ANTIBACTERIALS

The present invention relates to novel compounds, to processes for their preparation, to pharmaceutical compositions containing them and to their use in medical therapy, particularly antibacterial therapy.

Pleuromutilin, the compound of formula (A), is a naturally occurring antibiotic which has antimycoplasmal activity and modest antibacterial activity. Mutilin and other compounds with a free OH at C-14 are inactive. The impact of further modification at C-14 on the activity of pleuromutilin has been investigated (H. Egger and H. Reinshagen, *J. Antibiotics*, 1976, 29, 923). Replacing the hydroxy group of the glycolic ester moiety at position 14 by another O, S or N-linked group was found to improve anti-microbial activity. Thus, introducing a diethylaminoethylthio group gives the compound of formula (B), also known as Tiamulin, which is used as a veterinary antibiotic (G. Hogenauer in *Antibiotics*, Vol. V, part 1, ed. F. E. Hahn, Springer-Verlag, 1979, p.344).

(A)

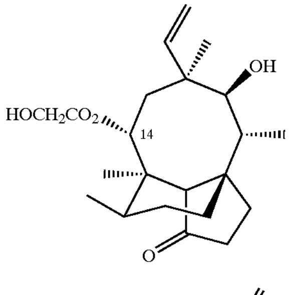

(B)

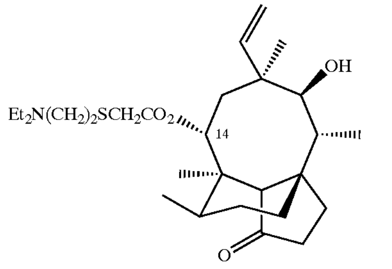

In this application, the non-conventional numbering system which is generally used in the literature (G. Hogenauer, loc. cit.) is used.

WO 97/25309 (SmithKline Beecham) describes further modification of the acyloxy group, disclosing inter alia 14-O-acylcarbamoyl ($R^aCONR^bCO_2$—) derivatives of mutilin in which $R^a$ may have a range of values, including optionally substituted heterocyclic and $R^b$ is a selected from a variety of monovalent groups.

WO 98/05659 (SmithKline Beecham) describes further 14-O-carbamoyl derivatives of mutilin in which the N-atom of the carbamoyl group is acylated by a group which includes an azabicyclic moiety.

WO 99/21855 (SmithKline Beecham) describes further derivatives of mutilin or 19,20-dihydromutilin, in which the glycolic ester moiety at position 14 is replaced by the group $R^2(CH_2)_mX(CH_2)_nCH_2COO$— in which $R^2$ is a non-aromatic mono- or bicyclic group.

WO 00/27790 (SmithKline Beecham) describes C-14 spirocyclic, acylcarbamate, heteroarylalkyl carboxylate or arylalkoxyalkyl carboxylate derivatives of mutilin or 19,20-dihydromutilin.

WO 00/37074 (SmithKline Beecham) describes further derivatives of mutilin or 19,20-dihydromutilin having a heteroaryl acetate substituent at the C-14 position.

WO 01/14310 (SmithKline Beecham) describes further derivatives of mutilin or 19,20-dihydromutilin having a β-keto ester substituent at the C-14 position.

In addition, 19,20-Dihydro-2α-hydroxy-mutilin is described by G. Schulz and H. Berner in *Tetrahedron*, 1984, vol. 40, pp 905–917.

The present invention is based on the unexpected discovery that certain novel C-14 ester derivatives of mutilin have potent antimicrobial activity.

Accordingly the present invention provides a compound of formula (IA) or (IB):

(IA)

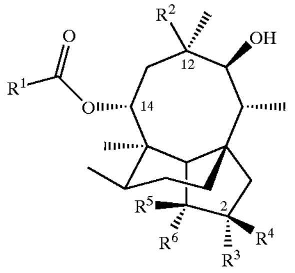

(IB)

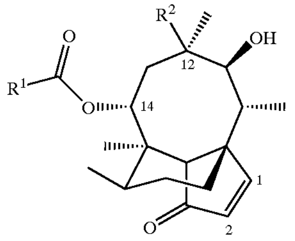

in which:

$R^1$ is:

a 5- or 6-membered aromatic or heteroaromatic ring attached via a ring carbon atom, preferably pyridyl, and comprising a substituent selected from halo, $R^7O$—, $R^7S$— or $R^8R^9N$— on a ring carbon adjacent to the carbon of attachment; or a 5- or 6-membered dihydro heteroaromatic ring attached via a ring carbon atom and comprising one oxygen or one or two nitrogen atoms and optionally fused to phenyl, a 5- or 6-membered heteroaryl ring comprising one or two nitrogen atoms or a 5- or 6-membered heterocyclyl ring comprising a sulphur, oxygen or nitrogen atom and further comprising a substituent selected from oxo or thioxo on a ring carbon adjacent to the carbon of attachment;

a 6-membered tetrahydro heteroaromatic ring attached via a ring carbon atom comprising one or two nitrogen atoms and farther comprising two substituents independently selected from oxo or thioxo wherein one of the substituents is on a ring carbon adjacent to the carbon of attachment; or a bicyclic heteroaryl ring attached via a ring carbon atom and comprising nine or ten ring atoms and from one to four nitrogen atoms;

wherein the ring of $R^1$ may be optionally further substituted;

$R^2$ is vinyl or ethyl;

$R^3$ is H, OH or F and $R^4$ is H, or $R^3$ is H and $R^4$ is F and $R^5$ and $R^6$ together form an oxo group;

or $R^3$ and $R^4$ is each H and $R^5$ is H, or OH and $R^6$ is H or $R^5$ is H and $R^6$ is H or OH;

$R^7$ is optionally substituted $C_{(1-6)}$alkyl; and $R^8$ and $R^9$ are independently selected from hydrogen or optionally substituted $C_{(1-6)}$alkyl.

Examples of compounds of formula (IA) include those in which $R^3$ and $R^4$ are both hydrogen, and $R^5$ and $R^6$ together form an oxo group.

Examples of rings for $R^1$ include pyrazole, pyrazine, pyridine, pyrimidine, and pyran which may be optionally fused with a 6 membered aromatic or non-aromatic ring, optionally containing up to two nitrogen atoms, for instance quinoline, azaquinolone, diazaquinilone, pyrimido[4,5-c]-pyridazine, chromane, in particular, the following:

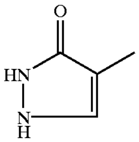 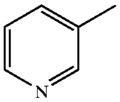 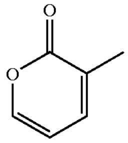

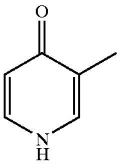 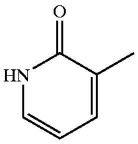 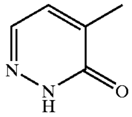

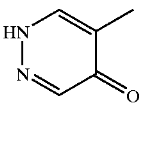 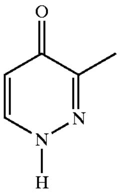 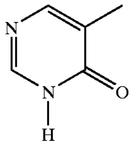

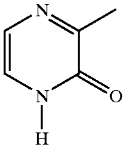 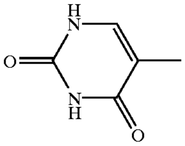

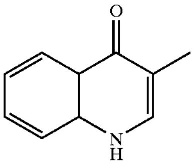 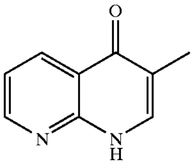

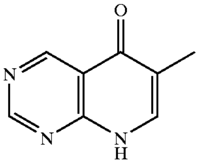 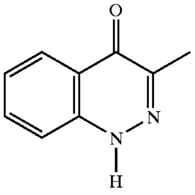

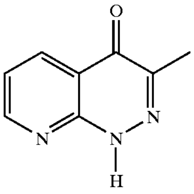 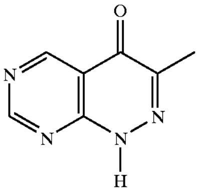

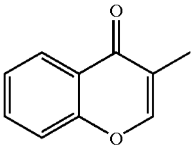 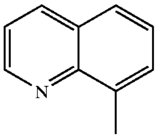

-continued

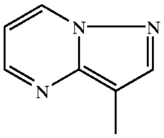 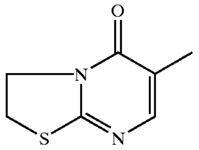

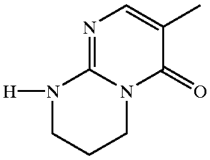 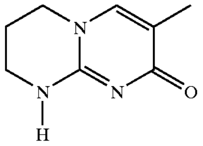

Preferred monocyclic examples of the ring for $R^1$ include:

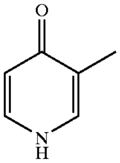 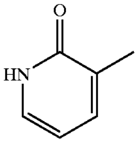 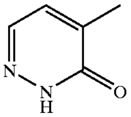

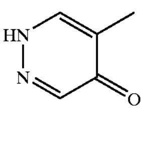 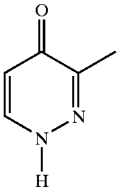 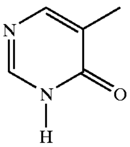

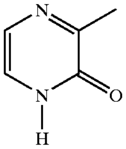

in particular those comprising the moiety

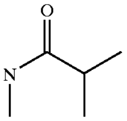

for example:

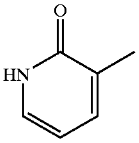 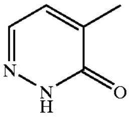

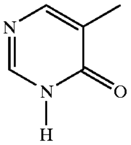 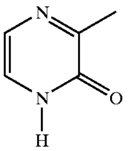

Preferred bicyclic examples of the ring for $R^1$ include:

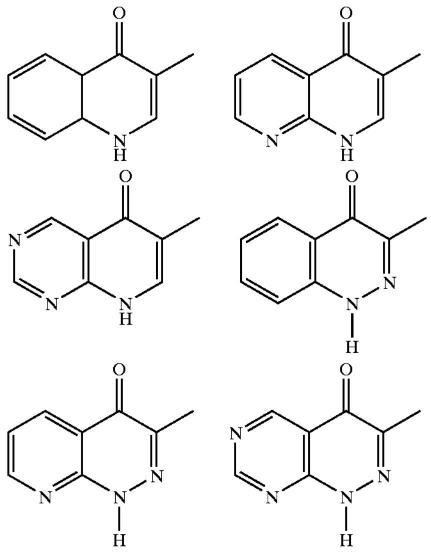

Examples of groups for $R^7$ include $(C_{1-6})$alkoxy, e.g. methoxy and ethoxy.

Examples of groups for $R^8$ and $R^9$ include hydrogen.

When further substituted, an $R^1$ group may comprise up to three substituents, preferably one or two, and may be substituted on a carbon atom and/or on a nitrogen atom.

Examples of optional substituents for carbon atoms of $R^1$ include halogen, $(C_{1-6})$alkyl, aryl, aryl$(C_{1-6})$alkyl, $(C_{1-6})$alkoxy, $(C_{1-6})$alkoxy$(C_{1-6})$alkyl, aryl$(C_{1-6})$alkoxy, hydroxy, nitro, cyano, azido, amino, mono- and di-N-$(C_{1-6})$alkylamino, acylamino, arylcarbonylamino, acyloxy, carboxy esters, carbamoyl, mono- and di-N-$(C_{1-6})$alkylcarbamoyl, $(C_{1-6})$alkoxycarbonyl, aryloxycarbonyl, hydrazino, ureido, guanidino, $(C_{1-6})$alkylguanidino, amidino, $(C_{1-6})$alkylamidino, sulphonylamino, aminosulphonyl, $(C_{1-6})$alkylthio, $(C_{1-6})$alkylsulphinyl, $(C_{1-6})$alkylsulphonyl, heterocyclyl, heteroaryl, heterocyclyl $(C_{1-6})$alkyl and heteroaryl$(C_{1-6})$alkyl.

Representative examples of optional substituents for carbon atoms of $R^1$ include $(C_{1-6})$alkyl, $(C_{1-6})$alkylthio, amino, mono- and di-N-$(C_{1-6})$alkylamino, $R^{10}(C_{1-6})$alkylamino, imidazolinyl, piperidinyl, piperazinyl (optionally substituted on N by $R^{11}$), pyridyl, hydrazino, N-$(C_{1-3})$alkylhydrazino, aminomethylcarbonylhydrazino, heterocyclyl$(C_{1-3})$alkyl in which heterocyclyl comprises a 6-membered ring with 1 nitrogen atom and optionally an oxygen or a second nitrogen, and in which:

$R^{10}$ is hydroxy, amino, heteroaryl in which heteroaryl comprises a 5 or 6-membered ring with 1 or 2 nitrogen atoms, heterocyclylin which heterocyclyl comprises a 6-membered ring with 1 nitrogen atom and optionally an oxygen or a second nitrogen, $R^{11}$-amino, in which:

$R^{11}$ is $(C_{1-3})$alkyl, hydroxy$(C_{1-3})$alkyl, carbamoyl, methylsulfonyl, amino$(C_{1-3})$alkylcarbonyl, for instance glycyl, aminocarbonyl$(C_{1-3})$alkyl.

Examples of optional substituents for nitrogen atoms of $R^1$, in particular nitrogen of a pyridine, pyridazine, pyrimidine or pyrazine ring, include $R^{12}(C_{1-6})$alkyl (preferably $R^{12}(C_{1-3})$alkyl), amino, mono- or di-$(C_{1-6})$alkylamino, N-(pyridyl$(C_{1-3})$alkyl)-N-$(C_{1-3})$alkylamino (in which pyridyl is optionally substituted, for example by $(C_{1-6})$alkoxy and/or amino, mono- or di-$(C_{1-6})$alkylamino), acyl- or sulfonyl amino, acyl- or sulfonyl-mono$(C_{1-6})$alkylamino, optionally substituted phenyl, $R^{13}C{=}N$—, $R^{14}(C_{1-4})$alkylN(H/Me)-, $R^{15}$CON(H/Me)- and $R^{16}$N(CHO)—, in which:

$R^{12}$ is hydrogen, halo, nitrilo, amino, $(C_{1-6})$alkoxy, $(C_{1-3})$alkoxy$(C_{1-6})$alkoxy, $(C_{1-6})$alkylcarboxy, $(C_{1-6})$alkoxy, heteroaryl, heteroarylcarbonyl, imidazolylthio, heterocyclyl, optionally substituted phenyl;

$R^{13}$ is $(C_{0-4})$alkylheteroaryl in which the heteroaryl ring is 5- or 6-membered and has 1 or 2 nitrogen atoms, for example pyridine, pyrazine and imidazole and which may be substituted by 1 or 2 substituents, for instance by $(C_{1-6})$alkoxy, nitro, amino, $(C_{1-6})$alkylamino, di-$(C_{1-6})$alkylamino, oxo;

$R^{14}$ is $(C_{1-4})$alkylheteroaryl in which the heteroaryl ring is 5 or 6 membered and has 1 or 2 nitrogen atoms, for example pyridine, and which may be substituted by 1 or 2 substituents, for instance by $(C_{1-6})$alkoxy, nitro, amino, $(C_{1-6})$alkylamino, di-$(C_{1-6})$alkylamino, oxo, $R^{15}$ is $(C_{1-6})$alkyl, $(C_{1-6})$alkoxy, aminomethyl, mono or dialkyl$(C_{1-6})$aminomethyl, a 4, 5 or 6 membered heterocyclic ring comprising a heteroatom selected from NH, NMe, and, for pyrrolidine, optionally substituted by hydroxy or methoxy, dioxothietane, imidazole, pyridine, pyridazine, pyrimidine, pyrazine; and $R^{16}$ is hydrogen, $(C_{1-6})$alkyl, benzyl or pyridinylmethyl.

Preferably, the ring in $R^1$ comprises one substituent.

Preferred values of $R^1$ include:

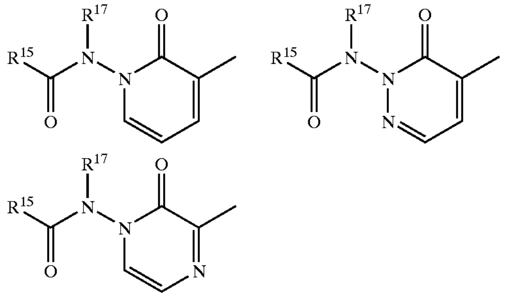

in which $R^{15}$ is as hereinbefore defined, preferably such that the moiety $R^{15}$NCO is derived from (D)- or (L)-proline, more preferably (L)-proline, and $R^{17}$ is hydrogen or $(C_{1-6})$alkyl, preferably methyl, and

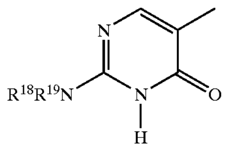

in which:

$R^{18}$ is $R^{10}(C_{1-6})$alkyl, and $R^{19}$ is hydrogen, or $R^{18}R^{19}$N— form a piperazinyl ring optionally substituted on N by $R^{11}$, in which $R^{10}$ and $R^{11}$ are as hereinbefore defined.

$R^1$ groups containing a substituent selected from oxo or thioxo on a ring carbon adjacent to the carbon of attachment are referred to as β-oxo and β-thioxo groups respectively.

When used herein, the term "aryl" refers to, unless otherwise defined, phenyl or naphthyl. A substituted aryl group comprises up to five, preferably up to three substituents.

Suitable substituents for an aryl group, including phenyl when forming part of a benzyl group, include, for example, and unless otherwise defined, halogen, $(C_{1-6})$alkyl, aryl, aryl$(C_{1-6})$alkyl, $(C_{1-6})$alkoxy, $(C_{1-6})$alkoxy$(C_{1-6})$alkyl, halo $(C_{1-6})$alkyl, aryl$(C_{1-6})$alkoxy, hydroxy, nitro, cyano, azido, amino, mono- and di-N-$(C_{1-6})$alkylamino, acylamino, arylcarbonylamino, acyloxy, carboxy, carboxy salts, carboxy esters, carbamoyl, mono- and di-N-$(C_{1-6})$alkylcarbamoyl, $(C_{1-6})$alkoxycarbonyl, aryloxycarbonyl, ureido, guanidino, $(C_{1-6})$alkylguanidino, amidino, $(C_{1-6})$alkylamidino, sulphonylamino, aminosulphonyl, $(C_{1-6})$alkylthio, $(C_{1-6})$alkylsulphinyl, $(C_{1-6})$alkylsulphonyl, heterocyclyl, heteroaryl, heterocyclyl$(C_{1-6})$alkyl and heteroaryl$(C_{1-6})$alkyl. In addition, two adjacent ring carbon atoms may be linked by a $(C_{3-5})$alkylene chain, to form a carbocyclic ring.

When used herein, the terms "alkyl" and "alkenyl" refer to (individually or as part of alkoxy or alkenyloxy) straight and branched groups containing up to six carbon atoms.

When used herein, the terms "cycloalkyl" and "cycloalkenyl" refer to groups having from three to eight ring carbon atoms.

When substituted, an alkyl, alkenyl, cycloalkyl or cycloalkenyl group may comprise up to four substituents, preferably up to two substituents. Suitable substituents for alkyl, alkenyl, cycloalkyl or cycloalkenyl groups include aryl, heteroaryl, heterocyclyl, $(C_{1-6})$alkoxy, $(C_{1-6})$alkylthio, aryl$(C_{1-6})$alkoxy, aryl$(C_{1-6})$alkylthio, amino, mono- or di-$(C_{1-6})$alkylamino, cycloalkyl, cycloalkenyl, carboxy and esters thereof, amide, ureido, guanidino, $(C_{1-6})$alkylguanidino, amidino, $(C_{1-6})$alkylamidino, $(C_{1-6})$acyloxy, azido, hydroxy, and halogen.

When used herein the terms "heterocyclyl" and "heterocyclic" refer to, unless otherwise defined, non-aromatic, single and fused, rings suitably containing up to four heteroatoms in each ring, each of which is selected from oxygen, nitrogen and sulphur. Each heterocyclic ring preferably has from 4 to 7, preferably 5 or 6, ring atoms. A fused heterocyclic ring system may include carbocyclic rings and need include only one heterocyclic ring.

When substituted, a heterocyclyl group may comprise up to three substituents. Preferably a substituent for a heterocyclyl group is selected from oxo, and the group hereinbefore defined as suitable aryl substituents.

When used herein, the term "heteroaryl" suitably includes, unless otherwise defined, a mono- or bicyclic heteroaromatic ring system comprising up to four, preferably 1 or 2, heteroatoms each selected from oxygen, nitrogen and sulphur. Each ring may have from 4 to 7, preferably 5 or 6, ring atoms. A bicyclic heteroaromatic ring system may include a carbocyclic ring.

When substituted, a heteroaryl group may comprise up to three substituents. Preferably a substituent for a heteroaryl group is selected from the group hereinbefore defined as suitable aryl substituents.

When used herein, the term "acyl" includes formyl and $(C_{1-6})$alkylcarbonyl.

When used herein the term "sulfonyl" includes $(C_{1-6})$alkylsulfonyl.

The term halo or halogen includes fluoro, chloro, bromo and iodo.

Depending on the substituents, two or more diastereoisomers may be possible. In that situation the present invention includes the individual diastereoisomers and mixtures thereof.

The 2-hydroxy-substituted compounds of formula (I) are of the 2 (S) configuration.

Preferred compounds of the invention include:

(4-Oxo-6,7,8,9-tetrahydro-4H-pyrimido[1,2-a]pyrimidine-3-carboxylic acid) mutilin 14-ester;

[2-(3-Morpholino-propylamino)-6-oxo-1,6-dihydro-pyrimidine-5-carboxylic acid) mutilin 14-ester;

(8-Ethyl-2-piperazin-1-yl-5-oxo-5,8-dihydro-pyrido[2,3-d]pyrimidine-6-carboxylic acid) mutilin 14-ester;

{1,6-Dihydro-1-[N-methyl-N-(D)-prolylamino]-6-oxo-pyridazine-5-carboxylic acid} mutilin 14-ester;

{1,2-Dihydro-1-[N-methyl-N-(D)-prolylamino]-2-oxo-pyridine-3-carboxylic acid} mutilin 14-ester;

{1,6-Dihydro-1-[N-methyl-N-(L)-prolylamino]-6-oxo-pyridazine-5-carboxylic acid} mutilin 14-ester; and {1,6-Dihydro-1-[N-methyl-N-(L)-trans-methoxy-prolylamino]-6-oxo-pyridazine-5-carboxylic acid} mutilin 14-ester.

The compounds of this invention may be in crystalline or non-crystalline form, and, if crystalline, may optionally be hydrated or solvated. This invention includes within its scope stoichiometric hydrates as well as compounds containing variable amounts of water.

The compounds according to the invention are suitably provided in substantially pure form, for example at least 50% pure, suitable at least 60% pure, advantageously at least 75% pure, preferably at least 85% pure, more preferably at least 95% pure, especially at least 98% pure, all percentages being calculated as weight/weight.

Compounds of the invention that contain a basic group such as an amino substituent may be in the form of a free base or an acid addition salt. Compounds having an acidic group such as a carboxy substituent may be in the form of a pharmaceutically acceptable salt. Compounds of the invention having both a basic and an acidic centre may be in the form of zwitterions, acid addition salt of the basic centre or alkali metal salts (of the carboxy group). Pharmaceutically acceptable salts are preferred.

Pharmaceutically acceptable acid-addition salts include those described by Berge, Bighley, and Monkhouse, *J. Pharm. Sci.*, 1977, 66, 1–19. Suitable salts include the hydrochloride, maleate, and methanesulphonate; particularly the hydrochloride.

Pharmaceutically acceptable salts for acidic groups include those described by Berge, Bighley, and Monkhouse, *J. Pharm. Sci.*, 1977, 66, 1–19. Suitable salts include alkali metal salts such as the sodium and potassium salts.

Compounds of the present invention may be readily prepared from a mutilin or a 19,20-dihydro-mutilin derivative by adapting procedures well known in the art for forming ester groups. Suitable procedures are reviewed in, for example, I. O. Sutherland in *Comprehensive Organic Chemistry*, Vol. 2, ed. I. O. Sutherland, p. 871–907, Pergamon, 1979.

Accordingly, the present invention provides a process for preparing a compound of formula (IA) or (IB) which comprises reacting a compound of formula (IIA) or (IIB):

(IIA)

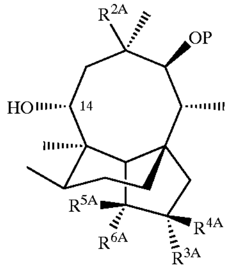

-continued (IIB)

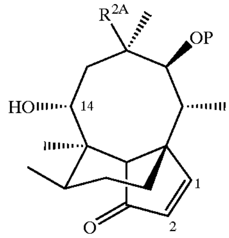

in which:

P is hydrogen or an hydroxy-protecting group;

$R^{2A}$, $R^{3A}$, $R^{4A}$, $R^{5A}$ and $R^{6A}$ are $R^2$, $R^3$, $R^4$, $R^5$ and $R^6$ as defined for formulae (IA) and (IB) or a group convertible to $R^2$, $R^3$, $R^4$, $R^5$ and $R^6$ respectively; and is as hereinbefore defined;

with a compound of formula (III):

(III)

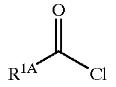

in which:

$R^{1A}$ is $R^1$ as defined for formulae (IA) and (IB) or a group convertible to $R^1$;

in an esterification reaction and thereafter, and if so needed; converting P to hydrogen, and if necessary converting an $R^{1A}$, $R^{2A}$, $R^{3A}$, $R^{4A}$, $R^{5A}$ and $R^{6A}$ group to an $R^1$, $R^2$, $R^3$, $R^4$, $R^5$ and $R^6$ group.

Suitable ester forming conditions include an organic solvent such as dichloromethane at a temperature of 10° C. to 30° C., in the presence of either silver oxide or an organic base such as pyridine or triethylamine.

In a further aspect, the present invention provides a process for preparing a compound of formula (IA) or (IB) in which $R^1$ contains an oxo or thioxo moiety on the ring adjacent to the carbon of attachment (i.e. a β-oxo or β-thioxo group) which comprises reacting a compound of formula (IVA) or (IVB):

(IVA)

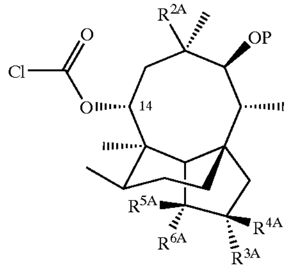

(IVB)

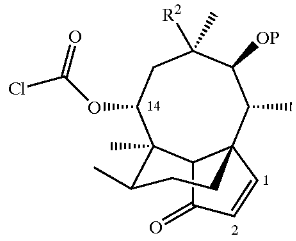

in which P, $R^{2A}$, $R^{3A}$, $R^{4A}$, $R^{5A}$ and $R^{6A}$ are as hereinbefore defined;

with a compound of formula (V):

(V)

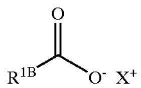

in which $R^{1B}$ is $R^1$ as hereinbefore defined containing a β-oxo or β-thioxo substituent, and X is a salt forming group; and thereafter treating the resulting mixed anhydride with 4-dimethylaminopyridine and thereafter, and if so needed; converting P to hydrogen, and if necessary converting an $R^{1A}$, $R^{2A}$, $R^{3A}$, $R^{4A}$, $R^{5A}$ and $R^{6A}$ group to an $R^1$, $R^2$, $R^3$, $R^4$, $R^5$ and $R^6$ group.

X is preferably sodium or triethylamine.

Suitable anhydride formation conditions are well known in the art and include an organic solvent such as dichloromethane, at a temperature of −20° C. to 20° C. (preferably −10° C. to 5° C.).

In a yet further aspect, the present invention provides a process for preparing a compound of formula (IA) or (IB) in which $R^1$ contains a β-oxo or β-thioxo group which comprises reacting a compound of formula (V) as hereinbefore defined, with phosgene and thereafter treating the resulting intermediate with a compound of formula (IIA) or (IIB) as hereinbefore defined, and thereafter and if so needed; converting P to hydrogen, and if necessary converting an $R^{1A}$, $R^{2A}$, $R^{3A}$, $R^{4A}$, $R^{5A}$ and $R^{6A}$ group to an $R^1$, $R^2$, $R^3$, $R^4$, $R^5$ and $R^6$ group.

Suitable conditions for the reaction of phosgene with compounds of formula (V) are well known in the art and include an organic solvent such as dichloromethane or N,N-dimethylformamide at a temperature of 0° C. to 40° C. (preferably 15° C. to 25° C.).

Conversion of an $R^{1A}$, $R^{2A}$, $R^{3A}$, $R^{4A}$, $R^{5A}$ and $R^{6A}$ group to an $R^1$, $R^2$, $R^3$, $R^4$, $R^5$ and $R^6$ group typically arises if a protecting group is needed during the above reactions or during the preparation of the reactants by the procedures described below.

When P is a hydroxyl protecting group, a preferred protecting group is acyl, for example so that —OP is trifluoroacetoxy or dichloroacetoxy. When the intended $R^3$, $R^5$ or $R^6$ is also hydroxyl, then $R^{3A}$, $R^{5A}$ and $R^{6A}$ is also preferably acyloxy, for example acetoxy or dichloroacetoxy. Hydroxyl groups at positions 11, 3 and 2 (as groups OP, $R^{5A}$ and $R^{6A}$ and $R^{3A}$) may be protected using, for example, trifluoroacetic anhydride or dichloroacetic anhydride and pyridine in tetrahydrofuran or N-trifluoroacetyl-imidazole in tetrahydrofuran at 0° C. After the reaction described above with (III) is complete, the protecting acyl groups may be removed to restore the hydroxyl groups, for instance by hydrolysis e.g. using NaOH in either MeOH or tetrahydrofuran/water solution.

Suitable hydroxy, carboxy and amino protecting groups are those well known in the art and which may be removed under conventional conditions and without disrupting the remainder of the molecule. A comprehensive discussion of the ways in which hydroxy, carboxy and amino groups may be protected and methods for cleaving the resulting protected derivatives is given in for example *Protective Groups in Organic Chemistry*, T. W. Greene and P. G. M. Wuts, (Wiley-Interscience, New York, 2nd edition, 1991). Particularly suitable hydroxy protecting groups include, for example, triorganosilyl groups such as, for instance, trialkylsilyl and also organocarbonyl and organooxycarbonyl groups such as, for instance, acetyl, allyloxycarbonyl and 4-methoxybenzyloxycarbonyl. Particularly suitable carboxy protecting groups include alkyl and aryl esters, for instance methyl, ethyl and phenyl. Particularly suitable amino protecting groups include alkoxycarbonyl and 4-methoxybenzyloxycarbonyl.

$R^{2A}$ is typically the $R^2$ group vinyl, and this may be converted to the alternative $R^2$ ethyl group by hydrogenating the vinyl group to form an ethyl group, typically by hydrogenation over a palladium catalyst (e.g. 10% palladium-on-carbon) in a solvent such as ethyl acetate, ethanol, dioxane, or tetrahydrofuran.

$R^{3A}$ is typically hydrogen, fluoro or protected hydroxyl, such as acyloxy. After the coupling reaction, if required, protecting acyl groups may be removed to restore the hydroxyl groups by hydrolysis e.g. using NaOH in MeOH.

A compound of formula (IA) may also be prepared from an epi-mutilin starting material. Accordingly, in a further aspect, the present invention provides a process for preparing a compound of formula (IA) in which $R^3$ and $R^4$ are both hydrogen and $R^5$ and $R^6$ form an oxo group, which comprises reacting an epi-mutilin compound of formula (IIC):

(IIC)

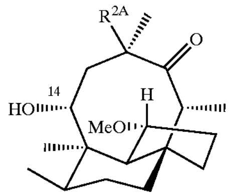

wherein $R^{2A}$ is as hereinbefore defined;

with a compound (III), as hereinbefore defined; under ester forming conditions as hereinbefore defined;

and then treating the product with an acid;

and where required or desired converting an $R^{1A}$ group to an $R^1$ group and an $R^{2A}$ group to an $R^2$ group.

In a further aspect, the present invention provides a process for the preparation of a compound of formula (IA) in which $R^3$ and $R^4$ are both hydrogen and $R^5$ and $R^6$ form an oxo group, which comprises reacting a compound of formula (IIC) as hereinbefore defined with an acid chloride of formula (III), as hereinbefore defined in the presence of N,N-dimethylformamide; and then treating the product with an acid;

and where required or desired converting an $R^{1A}$ group to an $R^1$ group and an $R^{2A}$ group to an $R^2$ group.

In a yet further aspect, the present invention provides a process for preparing a compound of formula (IA) in which $R^3$ and $R^4$ are both hydrogen and $R^5$ and $R^6$ form an oxo group, which comprises reacting an epi-mutilin compound of formula (VI):

(VI)

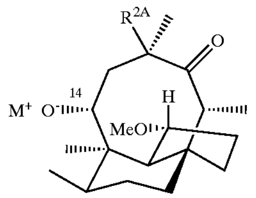

wherein $R^{2A}$ is as hereinbefore defined and M is an alkali metal;

with a compound (III), as hereinbefore defined in an ester forming reaction;

and then treating the product with an acid;

and where required or desired converting an $R^{1A}$ group to an $R^1$ group and an $R^{2A}$ group to an $R^2$ group.

Suitable ester forming conditions are known in the art and include an organic solvent such as tetrahydrofuran at −78° C. to 35° C.

Alkali metals include lithium, sodium and potassium, particularly lithium.

In a yet further aspect, the present invention provides a process for preparing a compound of formula (IA) in which $R^3$ and $R^4$ are both hydrogen, $R^5$ and $R^6$ form an oxo group and $R^1$ contains a β-oxo or β-thioxo group, which comprises reacting a compound of formula (IVC):

(IVC)

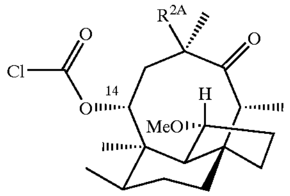

wherein $R^{2A}$ is as hereinbefore defined;

with a compound of formula (V) as hereinbefore defined in an anhydride forming reaction as hereinbefore defined;

and thereafter treating the resulting mixed anhydride with 4-dimethylaminopyridine and thereafter treating the product with an acid;

and where required or desired converting an $R^{1A}$ group to an $R^1$ group and an $R^{2A}$ group to an $R^2$ group.

In a yet further aspect, the present invention provides a process for preparing a compound of formula (IA) in which $R^3$ and $R^4$ are both hydrogen, $R^5$ and $R^6$ form an oxo group and $R^1$ contains a β-oxo or β-thioxo group, which comprises reacting a compound of formula (V) as hereinbefore defined, with phosgene and thereafter treating the resulting intermediate with a compound of formula (IVC) as hereinbefore defined, and thereafter treating the product with an acid;

and where required or desired converting an $R^{1A}$ group to an $R^1$ group and an $R^{2A}$ group to an $R^2$ group.

The acid treatment indicated above converts the epi-mutilin configuration to the usual mutilin nucleus of formula (IIA). Typically this conversion is carried out by treatment with conc. HCl or Lukas reagent (conc. HCl saturated with $ZnCl_2$) in dioxane.

It should be appreciated that it may be necessary to interconvert one $R^1$, $R^2$, $R^3$, $R^4$, $R^5$ or $R^6$ group to another $R^1$, $R^2$, $R^3$, $R^4$, $R^5$ or $R^6$ group. This typically arises when one compound of formula (IA/B) is used as the immediate precursor of another compound of formula (IA/B) or when it is easier to introduce a more complex or reactive substituent at the end of a synthetic sequence. A substituent group in $R^1$ can be converted into another substituent group using one of the general methods for functional group transformation described in the literature (e.g. a carboxylic ester can be hydrolysed to a carboxylic acid with base; an acid can be converted into an amide; a tert-butoxycarbonylamino group can be converted into an amine by treatment with trifluoroacetic acid; an amino group can be alkylated or acylated), provided that the method chosen is compatible with other functional groups in the molecule (e.g. the ketone at C-3 in the pleuromutilin nucleus).

Functional group transformations are well known in the art and are described in, for instance, *Comprehensive Organic Functional Group Transformations*, eds. A. R. Katritzky, O. Meth-Cohn, and C. W. Rees (Elsevier Science Ltd., Oxford, 1995), *Comprehensive Organic Chemistry*, eds. D. Barton and W. D. Ollis (Pergamon Press, Oxford, 1979), and *Comprehensive Organic Transformations*, R. C. Larock (VCH Publishers Inc., New York, 1989).

Compounds of formula (I) in which $R^1$:

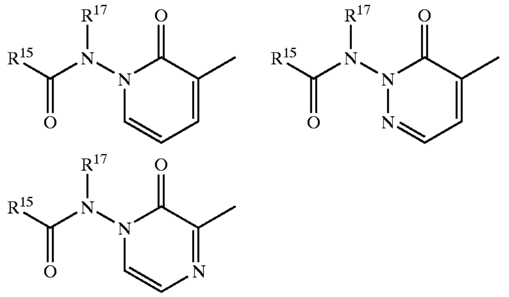

in which $R^{15}$ and $R^{17}$ are as hereinbefore defined; may be conveneniently prepared in a step wise fashion in which the mutilin nucleus is fisrt coupled with an unsubstituted pyridinone, pyridazinone or pyrazinone ($R^{1A}$) to give an intermediate which is then successively aminated, acylated (with $R^{17}CO$) and finally, if need be, N-methylated, to give the final compounds, such reactions being carried out under conventional conditions.

Compounds of formulae (IIA) in which $R^{3A}$ and $R^{4A}$ are hydrogen, (IIB) and (IIC) may be readily prepared according to methods described in the literature, for example G. Schulz and H. Berner, *Tetrahedron*, 1984, 40, 905, and in WO 97/25309 and WO 98/05659 (SmithKline Beecham). Where necessary, and as hereinbefore described, saponification of the C-14 ester may be carried out at an appropriate stage.

Compounds of formula (IIA) in which $R^{3A}$ is hydroxyl or fluoro may be prepared from pleuromutilin, via an intermediate 2-diazo compound, the preparation of which is described by G. Schulz and H. Berner in *Tetrahedron*, 1984, 40, 905. Where necessary, saponification of the C-14 ester group may be carried out at an appropriate stage using conventional techniques such as sodium hydroxide or sodium methoxide in methanol or aqueous tetrahydrofuran solution.

The intermediate 2-diazo compound may be reacted with a carboxylic acid to give a 2-acyloxy-mutilin derivative. Suitably, reaction with dichloroacetic acid gives a 2-dichloroacetoxy-mutilin derivative, which can be deprotected as described above to provide the (2S)-2-hydroxy derivative, at an appropriate stage.

Compounds of formula (IIA) in which $R^{3A}$ is fluoro may be obtained by reacting 2-diazo-mutilin with a source of hydrogen fluoride. Conveniently, the hydrogen fluoride source is an amine complex of hydrogen fluoride such as hydrogen fluoride-pyridine. The reaction may be carried out in an anhydrous solvent (e.g. diethyl ether, tetrahydrofuran, 1,2-dimethoxyethane), at a temperature of −15° C. to 25° C. This reaction produces (2S)-2-fluoro derivatives. (2R)-2-Fluoro-mutilin derivatives may be prepared by treating the (2S)-isomer with a base (e.g. sodium hydroxide or potassium hydroxide in ethanol). This will usually produce a mixture of (2S) and (2R)-isomers that may be separated using conventional techniques such as chromatography and crystallisation.

Compounds of formula (IIA) in which $R^5$ is hydroxy and $R^6$ is hydrogen may be prepared according to methods described in the literature, for example, by reduction of a mutilin with lithium aluminium hydride as described by Birch et al, *Tetrahedronl*, 1966, supp 8 (II), 359–387; or by reduction with lithium tri-tert-butoxyaluminohydride in dioxane as described by G. Schultz et al, *Tetrahedron*, 1984, 40, 905–917.

Compounds of formula (IIA) in which $R^5$ is hydrogen and $R^6$ is hydroxy may be prepared according to the methods described in the literature, for example, by reduction of a mutilin with lithium and methanol in liquid ammonia, as described by Birch et al, *Tetrahedron*, 1966, supp 8 (II), 359–387.

Compounds of formula (IIA) in which $R^5$ and $R^6$ are both hydrogen may be prepared according to the method of G. Schultz et al, *Tetrahedron*, 1984, 40, 905–917, by reduction with potassium hydroxide and hydrazine in refluxing diethylene glycol.

Acid chlorides of formula (III) and (IV) are available commercially, or may be readily prepared by adapting procedures well known in the art for the conversion of carboxylic acids to acid chlorides e.g. M. F. Ansell in *The Chemistry of Acyl Halides*, ed. S. Patai, pp 35–68 (Interscience, London, 1972) and include, for example, oxalyl chloride in dichloromethane solution in the presence of N,N-dimethylformamide.

Carboxylates salts of formula (V) are available commercially or may be readily prepared from the carboxylic acid by methods known to those skilled in the art.

Carboxylic acids may be prepared by adapting procedures well known in the art for preparing such acids e.g. *Comprehensive Organic Chemistry*, Vol. 2, Ed. I. O. Sutherland (Pergamon, Oxford, 1979).

Compounds of formula (VI) may be readily prepared by adapting procedures well known in the art for preparing alkali metal salts. Lithium salts may be prepared by the addition of an alkyl lithium (e.g. n-butyl lithium) or a lithium amide (e.g. lithium hexamethyldisilazide) to 4-epi-mutilin in THF at −78° C. Sodium salts may be prepared using sodium hydride or a sodium amide (e.g. sodium hexamethyldisilazide), and potassium salts may be prepared using potassium tert-butoxide.

The compounds of the present invention may contain a chiral centre, and therefore the above processes may produce a mixture of diastereoisomers. A single diastereoisomer may be prepared by separating such a mixture of diastereoisomers by conventional techniques such as chromatography or fractional crystallisation.

The compounds of this invention may be in crystalline or non-crystalline form, and, if crystalline, may optionally be hydrated or solvated. When some of the compounds of this invention are allowed to crystallise or are recrystallised from organic solvents, solvent of crystallisation may be present in the crystalline product. Similarly, some of the compounds of this invention may be crystallised or recrystallised from solvents containing water. In such cases water of hydration may be present in the crystalline product. Crystallisation procedures will usually produce stoichiometric hydrates. Compounds containing variable amounts of water may be produced by processes such as lyophilisation.

The compounds according to the invention are suitably provided in substantially pure form, for example at least 50% pure, suitable at least 60% pure, advantageously at least 75% pure, preferably at least 85% pure, more preferably at least 95% pure, especially at least 98% pure, all percentages being calculated as weight/weight. An impure or less pure form of a compound according to the invention may, for example, be used in the preparation of a more pure form of the same compound or of a related compound (for example a corresponding derivative) suitable for pharmaceutical use.

The present invention also includes pharmaceutically acceptable salts and derivatives of the compounds of the invention. Salt formation may be possible when one of the substituents carries an acidic or basic group. Salts may be prepared by salt exchange in conventional manner.

Acid-addition salts may be pharmaceutically acceptable or non-pharmaceutically acceptable. In the latter case, such salts may be useful for isolation and purification of the compound of the invention, or intermediates thereto, and will subsequently be converted into a pharmaceutically acceptable salt or the free base.

The compounds of the present invention and their pharmaceutically acceptable salts or derivatives have antimicrobial properties and are therefore of use in therapy, in particular for treating microbial infections in animals, especially mammals, including humans, in particular humans and domesticated animals (including farm animals). The compounds may be used for the treatment of infections caused by, for example, Gram-positive and Gram-negative bacteria and mycoplasmas, including, for example, *Staphylococcus aureus, Staphylococcus epidermidis, Enterococcus faecalis, Streptococcus pyogenes, Streptococcus agalactiae, Streptococcus pneumoniae, Haemophilus* sp., *Neisseria* sp., *Legionella* sp., *Chlamydia* sp., *Moraxella catarrhalis, Mycoplasma pneumoniae*, and *Mycoplasma gallisepticum.*

The present invention also provides a method of treating microbial infections in animals, especially in humans and in domesticated mammals, which comprises administering a compound of the invention or a pharmaceutically acceptable salt or derivative or solvate thereof, or a composition according to the invention, to a patient in need thereof.

Compounds of the present invention show good activity against *Chlamydia pneumoniae*. This has been implicated in heart disease, in particular in promoting vascular infection (see for instance FR 2,771,008-A1, Hoechst Marion Roussel SA). Accordingly, in a further aspect, the present invention provides a method of preventing *C. pneumoniae*-induced atherosclerosis which method comprises treating a subject in need thereof with an effective amount of a compound of formula (I). A compound of formula (I) may also be used in combination with an anti-atherosclerotic agent, to reduce the incidence of heart attack and other cardiac events. Representative examples of anti-atherosclerotic agents include the class of cholesterol-lowering compounds referred to generically as “statins”, for instance atorvastatin (Lipitor, Warner Lambert), pravastatin (Pravachol), simvastatin (Lipovas, Merck) and cerivastatin (Baycol, Bayer). It has also been suggested that *Chlamydia pneumoniae* may contribute to Alzheimer’s Disease. Accordingly, in a further aspect, the present invention provides a method of treating Alzheimer’s Disease which method comprises treating a subject in need thereof with an effective amount of a compound of formula (I).

The invention further provides the use of a compound of the invention or a pharmaceutically acceptable salt or derivative or solvate thereof in the preparation of a medicament for use in the treatment of microbial infections.

Compounds of the present invention may be used to treat skin and soft tissue infections and acne, by topical application. Accordingly, in a further aspect the present invention provides the use of a compound of the invention or a pharmaceutically acceptable salt or derivative or solvate thereof in the preparation of a medicament adapted for topical administration for use in the treatment of skin and soft tissue infections and also in the treatment of acne in humans.

Compounds of the present invention may be also used for the elimination or reduction of nasal carriage of pathogenic bacteria such as *S. aureus, H. influenzae, S. pneumonia* and *M. catarrhalis*, in particular colonisation of the nasospharynx by such organisms, by the administration of a compound of the present invention thereto. Accordingly, in a further aspect, the present invention provides for the use of a compound of the invention or a pharmaceutically acceptable salt or derivative or solvate thereof in the manufacture of a medicament adapted for administration to the nasal cavity, for reducing or eliminating the nasal carriage of pathogenic organisms. Preferably, the medicament is adapted for focussed delivery to the nasopharynx, in particular the anterior nasopharynx.

Such reduction or elimination of nasal carriage is believed to be useful in prophylaxis of recurrent acute bacterial sinusitis or recurrent otitis media in humans, in particular in reducing the number of episodes experienced by a patient over a given period of time or increasing the time intervals between episodes. Accordingly, in a further aspect, the present invention provides for the use of a compound of the invention or a pharmaceutically acceptable salt or derivative or solvate thereof in the manufacture of a medicament adapted for administration to the nasal cavity, for prophylaxis of recurrent acute bacterial sinusitis or recurrent otitis media.

Compounds of the present invention are also useful in treating chronic sinusitis. Accordingly, in a further aspect, the present invention provides for the use of a compound of the invention or a pharmaceutically acceptable salt or derivative or solvate thereof in the manufacture of a medicament, for treating of chronic sinusitis.

The compounds according to the invention may suitably be administered to the patient at a daily dosage of from 1.0 to 50 mg/kg of body weight. For an adult human (of approximately 70 kg body weight), from 50 to 3000 mg, for example about 1500 mg, of a compound according to the invention may be administered daily. Suitably, the dosage for adult humans is from 5 to 20 mg/kg per day. Higher or lower dosages may, however, be used in accordance with normal clinical practice.

To lessen the risk of encouraging the development of resistant organisms during prophylaxis of recurrent otitis media or recurrent acute bacterial sinusitis, it is preferred to administer the drug on an intermittent, rather than a continual, basis. In a suitable intermittent treatment regimen for prophylaxis of recurrent otitis media or recurrent sinusitis, drug substance is administered on a daily basis, for a small number of days, for instance from 2 to 10, suitably 3 to 8, more suitably about 5 days, the administration then being repeated after an interval, for instance, on a monthly basis over a period of months, for instance up to six months. Less preferably, the drug substance may be administered on a continuing, daily basis, over a prolonged period, for instance several months. Suitably, for prophylaxis of recurrent otitis media or recurrent sinusitis, drug substance is administered once or twice a day. Suitably, drug substance is administered during the winter months when bacterial infections such as recurrent otitis media and recurrent sinusitis tend to be more prevalent. The drug substance may be administered at a dosage of from 0.05 to 1.00 mg, typically about 0.1 to 0.2 mg, in each nostril, once or twice a day.

More generally, the compounds and compositions according to the invention may be formulated for administration in any convenient way for use in human or veterinary medicine, by analogy with other antibiotics.

Accordingly, in a further aspect, the present invention provides a pharmaceutical composition comprising a compound of the invention or a pharmaceutically acceptable salt or derivative or solvate thereof together with a pharmaceutically acceptable carrier or excipient.

The compounds and compositions according to the invention may be formulated for administration by any route, for example oral, topical or parenteral. The compositions may, for example, be made up in the form of tablets, capsules, powders, granules, lozenges, creams, syrups, sprays or liquid preparations, for example solutions or suspensions, which may be formulated for oral use or in sterile form for parenteral administration by injection or infusion.

Tablets and capsules for oral administration may be in unit dosage form, and may contain conventional excipients including, for example, binding agents, for example, syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; and pharmaceutically acceptable wetting agents, for example sodium lauryl sulphate. The tablets may be coated according to methods well known in normal pharmaceutical practice.

Oral liquid preparations may be in the form of, for example, aqueous or oily suspensions, solutions, emulsions, syrups or elixirs, or may be presented as a dry product for reconstitution with water or another suitable vehicle before use. Such liquid preparations may contain conventional additives, including, for example, suspending agents, for example sorbitol, methyl cellulose, glucose syrup, gelatin, hydroxyethyl cellulose, carboxymethyl cellulose, aluminium stearate gel or hydrogenated edible fats; emulsifying agents, for example lecithin, sorbitan monooleate or acacia; non-aqueous vehicles (which may include edible oils), for example almond oil, oily esters (for example glycerine), propylene glycol, or ethyl alcohol; preservatives, for example methyl or propyl p-hydroxybenzoate or sorbic acid; and, if desired, conventional flavouring and colour agents.

Compositions according to the invention intended for topical administration may, for example, be in the form of ointments, creams, lotions, eye ointments, eye drops, ear drops, nose drops, nasal sprays, impregnated dressings, and aerosols, and may contain appropriate conventional additives, including, for example, preservatives, solvents to assist drug penetration, and emollients in ointments and creams. Such topical formulations may also contain compatible conventional carriers, for example cream or ointment bases, ethanol or oleyl alcohol for lotions and aqueous bases for sprays. Such carriers may constitute from about 1% to about 98% by weight of the formulation; more usually they will constitute up to about 80% by weight of the formulation.

Compositions according to the invention intended for topical administration, in addition to the above, may also contain a steroidal anti-inflammatory agent; for example, betamethasone.

Compositions according to the invention may be formulated as suppositories, which may contain conventional suppository bases, for example cocoa-butter or other glycerides.

Compositions according to the invention intended for parenteral administration may conveniently be in fluid unit dosage forms, which may be prepared utilizing the compound and a sterile vehicle, water being preferred. The compound, depending on the vehicle and concentration used, may be either suspended or dissolved in the vehicle. In preparing solutions, the compound may be dissolved in water for injection and filter-sterilised before being filled into a suitable vial or ampoule, which is then sealed. Advantageously, conventional additives including, for example, local anaesthetics, preservatives, and buffering agents can be dissolved in the vehicle. In order to enhance the stability of the solution, the composition may be frozen after being filled into the vial, and the water removed under vacuum; the resulting dry lyophilised powder may then be sealed in the vial and a accompanying vial of water for injection may be supplied to reconstitute the liquid prior to use. Parenteral suspensions may be prepared in substantially the same manner except that the compound is suspended in the vehicle instead of being dissolved and sterilisation cannot be accomplished by filtration. The compound may instead be sterilised by exposure to ethylene oxide before being suspended in the sterile vehicle. Advantageously, a surfactant or wetting agent is included in such suspensions in order to facilitate uniform distribution of the compound.

A compound or composition according to the invention is suitably administered to the patient in an antimicrobially effective amount.

A composition according to the invention may suitably contain from 0.001% by weight, preferably (for other than spray compositions) from 10 to 60% by weight, of a compound according to the invention (based on the total weight of the composition), depending on the method of administration.

When the compositions according to the invention are presented in unit dosage form, for instance as a tablet, each unit dose may suitably comprise from 25 to 1000 mg, preferable from 50 to 500 mg, of a compound according to the invention.

Representative compositions of the present invention include those adapted for intranasal administration, in particular, those that will reach into the nasopharynx. Such compositions are preferably adapted for focussed delivery to, and residence within, the nasopharynx. The term 'focussed delivery' is used to mean that the composition is delivered to the nasopharynx, rather than remaining within the nares. The term 'residence' within the nasopharynx is used to mean that the composition, once delivered to the nasopharynx, remains within the nasopharynx over a course of several hours, rather than being washed away more or less immediately. Preferred compositions include spray compositions and creams. Representative spray compositions include aqueous compositions, as well as oily compositions that contain amphiphilic agents so that the composition increases in viscosity when in contact with moisture. Creams may also be used, especially creams having a rheology that allows the cream to spread readily in the nasopharynx.

Preferred aqueous spray compositions include, in addition to water, further excipients including a tonicity modifier such as a salt, for instance sodium chloride; preservative, such as benzalkonium salt; a surfactant such as a non-ionic surfactant, for instance a polysorbate; and buffer, such as sodium dihydrogen phosphate; present in low levels, typically less than 1%. The pH of the composition may also be adjusted, for optimum stability of the drug substance during storage. For compounds of the present invention, a pH in the range 5 to 6, preferably about 5.3 to 5.8, typically about 5.5 is optimal.

Representative oily spray and cream compositions are described in WO 98/14189 (SmithKline Beecham). Representative aqueous sprays are described in International Application No. PCT/GB98/03211 (SmithKline Beecham).

Suitably, the drug substance is present in compositions for nasal delivery in between 0.001 and 5%, preferably 0.005 and 3%, by weight of the composition. Suitable amounts include 0.5% and 1% by weight of the composition (for oily compositions and creams) and from 0.01 to 0.2% (aqueous compositions).

Spray compositions according to the present invention may be delivered to the nasal cavity by spray devices well known in the art for nasal sprays, for instance an air lift pump. Preferred devices include those that are metered to provide a unit volume of composition, preferably about 100 μl, and optionally adapted for nasal administration by addition of a modified nozzle.

The invention is illustrated by the following Examples.

EXAMPLES

Preparation 1 (2S)-2-Dichloroacetoxy-11-O-trifluoroacetylmutilin

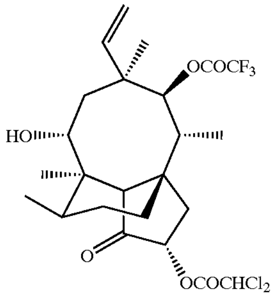

(a) Formylated derivatives of mutilin—The reaction was carried out similarly to that described by A. J. Birch, C. W. Holzapfel and R. W. Rickards (Tet (Suppl) 1996 8 part III 359). Mutilin (6 g) in toluene (330 ml) and methyl formate (100 ml) was treated with sodium methoxide (3 g) and stirred under argon for 8 hours. Ice-water (100 ml) was added, followed by 2N HCl (220 ml). The mixture was shaken and separated and the aqueous extracted with ether. The combined organic was dried and evaporated and the residue chromatographed, eluting with ethyl acetate/hexane mixtures. First eluted was 2-hydroxymethylenemutilin 11,14-diformate (2.33 g) $^1$HNMR ($CDCl_3$) inter alia 5.02 (1H, d), 5.77 (1H, d), 6.94 (1H, s), 7.89 (1H, s), 8.10 (1H, s). Second to be eluted was 2-hydroxymethylenemutilin 11-formate (3.0 g): $^1$H NMR δ($CDCl_3$) inter alia 4.40 (1H, d), 5.11 (1H, d), 7.06 (1H, s), 8.25 (1H, d, J 0.8 Hz). Third to be eluted was a mixture (2:1) of 2-hydroxymethylenemutilin 14-formate and 2-hydroxymethylenemutilin (1.8 g).

(b) 2-Hydroxymethylenemutilin—A mixture of 2-hydroxymethylenemutilin 11,14-diformate (2.33 g) and [2-hydroxymethylenemutilin 14-formate+2-hydroxymethylenemutilin] (1.8 g) was dissolved in ethanol (30 ml) and treated with 0.5M KOH in ethanol (60 ml). After 1 hour the solution was diluted with ethyl acetate (200 ml), washed with 2M HCl (120 ml) and water (100 ml), dried and evaporated to provide 2-hydroxymethylenemutilin as a foam (3.6 g); $^1$H NMR δ($CDCl_3$) inter alia 3.45 (1H, d), 4.37 (1H, d), 6.97 (1H, s).

(c) 2-Diazomutilin—A solution of 2-hydroxymethylenemutilin (3.6 g) in dichloromethane was cooled to −10° C. under argon, treated with triethylamine (4.6 ml) and tosyl azide (3.55 g) and warmed to room temperature. After 6 hours the solution was washed with 0.5M HCl (150 ml) and water (100 ml), dried and evaporated. The 2-diazomutilin was obtained as yellow crystals (1.7 g) from ethyl acetate/hexane; IR ($CHCl_3$) 3634, 2082 and 1670 $cm^{-1}$.

(d) (2S)-2-Dichloroacetoxymutilin—A solution of 2-diazomutilin (1.7 g) in dichloromethane (40 ml) was ice-cooled and treated dropwise with dichloracetic acid (0.5 ml). The bath was removed and after 30 minutes the solution was colourless. It was washed with aqueous $NaHCO_3$ (50 ml), dried and evaporated. Chromatography, eluting with 1:3 ethyl acetate/hexane, gave the title compound as the less polar of 2 major products (white foam, 1.6 g): $^1$H NMR δ($CDCl_3$) inter alia 3.33 (1H, t, J 5.8 Hz), 4.33 (1H, d, J 7 Hz), 5.04 (1H, t, J 9 Hz), 5.2–5.4 (2H, m), 5.96 (1H, s), 6.14 (1H, dd, J 17.5 and 10.5 Hz).

(e) (2S)-2-Dichloroacetoxy-11-O-trifluoroacetylmutilin—(2S)-2-Dichloroacetoxymutilin (5.8 g, 0.012 mole) in dry tetrahydrofuran (120 ml) was treated with trifluoroacetylimidazole (1.54 ml, 0.0135 mole) and stirred at ambient temperature for 18 hours. Ethyl acetate (200 ml) was added to the mixture which was then washed with dilute sodium chloride solution (2×200 ml). The organic layer was separated, dried ($Na_2SO_4$), filtered and evaporated to dryness. Chromatography on silica gel, eluting with ethylacetate/hexane (9:1) gave the title compound 4.98 g (71%) $^1$H NMR δ($CDCl_3$) inter alia 0.85 (3H, d, J 7 Hz), 0.95 (3H, d, J 7 Hz), 1.05 (3H, s), 1.39 (3H, s), 4.29 (1H, t, J 7 Hz), 4.86 (1H, d, J 7 Hz), 5.08 (1H, t, J 9 Hz), 5.99 (1H, s).

Preparation 2 Sodium 3-pyridazinol-4-carboxylate

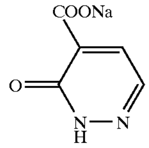

(a) Ethyl 3-pyridazinol-4-carboxylate—A solution of ethyl 6-chloro-3-pyridazinol-4-carboxylate (1.01 g) (T. Kuraishi, Chem. Pharm. Bull. (1957) 587–589) in ethanol (40 ml) was treated with 35% aqueous anmmonia (0.317 ml) and 10% Pd/C (200 mg) and stirred under hydrogen at atmospheric pressure for 45 mins. The mixture was filtered through kieselguhr and the filtrate evaporated. The residue was taken up in chloroform (20 ml) and solid filtered off. The filtrate was chromatographed, eluting with EtOAc/hexane to give title compound (0.55 g) as a white solid. MS (+ve ion chemical ionisation) m/z 169 ($MH^+$, 100%).

(b) Sodium 3-pyridazinol-4-carboxylate—A solution of ethyl 3-pyridazinol-4-carboxylate (0.52 g) in dioxan (15 ml) was treated with 2N aqueous NaOH (1.7 ml), stirred 1½ hours, treated with a further 0.7 ml of 2N NaOH solution and left for 2 hours. The solution was evaporated to dryness and the resulting white solid dried under vacuum in the presence of $P_2O_5$. NMR δ($D_2O$) 7.22(1H, d, J6.8 Hz), 8.09(1H, d, J6.8 Hz).

Preparation 3 4-Quinolone-3-carboxylic acid

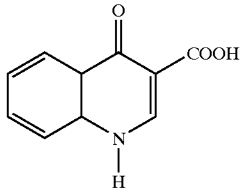

A suspension of ethyl 4-quinolone-3-carboxylate (900 mg) (Maybridge Chemical Co. Ltd) in dioxan (6 ml)/water (6 ml) was treated with 40% NaOH solution (8 ml) and refluxed 6 hours. The solution was cooled, acidified to pH2 with conc. HCl and the solid filtered off and dried under vacuum in the presence of $P_2O_5$ to provide the title compound (785 mg). MS (−ve ion chemical ionisation) m/z 188([M−H]$^-$, 100%).

Preparation 4 BOC derivatives of 2-amino-4-hydroxypyrimidine-5-carboxylic acid (a) BOC derivatives of ethyl 2-amino-4-hydroxypyrimidine-5-carboxylate—A mixture of ethyl 2-amino-4-hydroxypyrimidine-5-carboxylate (1.83 g), $Et_3N$ (1.39 ml), 4-dimethylaminopyridine (100 mg) and di-t-butyldicarbonate (8.6 g) in dichloromethane (30 ml) was stirred overnight, applied to a column and eluted with ethyl acetate/hexane. The oily product (1.8 g) was a mixture of BOC derivatives.

(b) BOC derivatives of 2-amino-4-hydroxypyrimidine-5-carboxylic acid—The product from step (a) in dioxan (20 ml)/water (5 ml) was treated with 2N NaOH solution (5 ml) and stirred overnight. EtOAc (40 ml) and an aqueous solution of citric acid (3 g in 20 ml) were added, the layers shaken and separated. The organic was washed with water, dried and evaporated to provide the title mixture as a white solid. MS (−ve ion electrospray) m/z 354 ([M−H]$^-$ for bis BOC derivative, 100%).

Preparation 5 1-(3-Nitrophenyl)-3-oxo-2,3-dihydro-1H-pyrazole-4-carboxylic acid

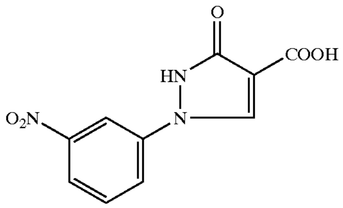

1-(3-Nitrophenyl)-3-oxo-2,3-dihydro-1H-pyrazole-4-carboxylic acid methyl ester (1.43 g, 0.005 mole) (Taylor A. W. et al, Tetrahedron, 1987, 43 (3), 607–616) in 1,4-dioxane (100 ml) and water (100 ml) was treated with sodium hydroxide (2 g, 0.05 mole) and heated under reflux for 6 hours. The mixture was allowed to cool then concentrated to a small volume in-vacuo, and acidified with concentrated hydrochloric acid. The resulting solid was filtered off and dried in-vacuo to give the title compound as an off-white solid (0.78 g, 60%). M.S. (−ive ion electrospray) m/z 248 ([M−H]$^-$, 25%), 276 (100%).

Preparation 6 7-(4-tert-Butoxycarbonylpiperazin-1-yl)-1-ethyl-6-fluoro-4-oxo-1,4-dihydroquinoline-3-carboxylic acid

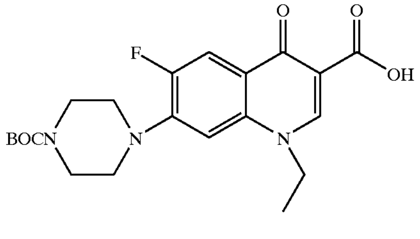

7-(1-Piperazinyl)-1-ethyl-6-fluoro-4-oxo-1,4-dihydroquinoline-3-carboxylic acid (2.0 g) in tetrahydrofuran/water 1:1 (200 ml) was treated with 2.0 M sodium hydroxide (3.5 ml) followed by di-tert-butyldicarbonate (1.5 g) and stirred at ambient temperature for 18 hours. The tetrahydrofuran was removed in-vacuo and the mixture acidified with citric acid. The resulting precipitate was filtered off and dried in-vacuo to give the title compound (2.6 g). M.S. (+ve ion chemical ionisation) m/z 420 (MH$^+$, 20%), 276 (100%).

Preparation 7 14-O-Chlorocarbonyl-(2S)-2-dichloroacetoxy-11-O-trifluoroacetylmutilin

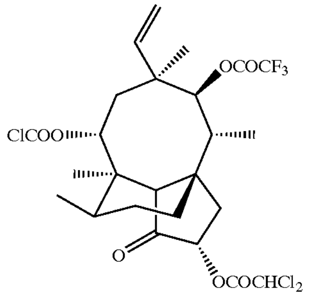

A solution of (2S)-2-dichloroacetoxy-11-O-trifluoroacetylmutilin (542 mg) in dichloromethane (5 ml) was treated with pyridine (0.081 ml) and triphosgene (296 mg) and stirred three hours. EtOAc (30 ml) was added, the solution washed with water (2×20 ml), dried and evaporated to give title compound.

Preparation 8 3,4-Dihydro-4-oxopyrimidine-5-carboxylic acid

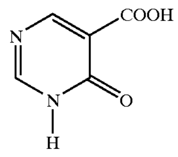

Ethyl 3,4-dihydro-4-oxopyrimidine-5-carboxylate (K R Huffman, F C Schaefer and G A Peters, J. Org. Chem. (1962) 27, 551–8) (1.68 g) was dissolved in 1N NaOH (23 ml) and heated at 60° C. overnight. After cooling in ice, the solution was acidified to pH2 with 2N HCl, stirred 5 mins and the solid filtered off and dried under vacuum to give title compound (1.25 g).

Preparation 9 3,4-Dihydro-2-methylthio-4-oxopyrimidine-5-carboxylic acid

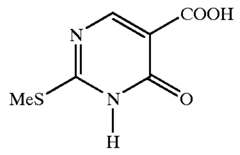

A solution of ethyl 3,4-dihydro-2-methylthio-4-oxopyrimidine-5-carboxylate (C. W. Todd, J. H. Fletcher and D. S. Tarbell, J. Am. Chem. Soc. (1943), 65, 350–4) (1.95 g) in dioxan (15 ml) was treated with aqueous NaOH (0.73 g in 15 ml) and heated at 85° C. overnight. After cooling, the solution was acidified with 2N HCl to pH3 and the white solid filtered off and dried under vacuum to give title compound (1.03 g). MS (−ve ion chemical ionisation) m/z 185 ([M−H]⁻, 70%), 141 (100%).

Preparation 10 3,4-Dihydro-2-dimethylamino-4-oxopyrimidine-5-carboxylic acid

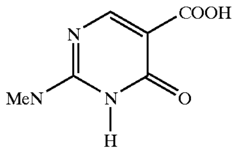

Ethyl 3,4-dihydro-2-dimethylamino-4-oxopyrimidine-5-carboxylate (P. Dostert, T Imbert, J F Ancher, M Langlois, B Bucher and G Mocquet, Eur. J. Med. Chem.-Chim. Ther. (1982), 17, 437–44) (0.64 g) was refluxed with NaOH (304 mg) in water (16 ml) for 2 hours. The cooled solution was acidified to pH2 with 1N HCl, solid filtered off and dried under vacuum at 75° C. to give title compound (0.52 g). MS (−ve ion chemical ionisation) m/z 182 ([M−H]⁻, 100%).

Preparation 11 3,4-Dihydro-2-(N-BOC-N-methylamino)-4-oxopyrimidine-5-carboxylic acid

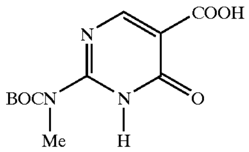

Ethyl 3,4-dihydro-2-methylamino-4-oxopyrimidine-5-carboxylate (P. Dostert et al, Eur. J. Med. Chem.-Chim. Ther. (1982), 17, 437–44) (0.67 g) in dichloromethane (10 ml) was treated with $Et_3N$ (0.472 ml), DMAP (catalytic) and di-t-butyl dicarbonate (2.15 g). After leaving overnight, the solution was added to a silica column and eluted 15% EtOAc/hexane to obtain as the major product a bis-BOC compound (0.47 g). A solution of this in dioxan (5 ml)/water (2 ml) was treated with 2 N NaOH (3 ml) and stirred overnight. Excess citric acid was added and the mixture extracted with EtOAc (10 ml). The organic was washed with water (10 ml), dried and evaporated to leave the title compound as a white solid (0.318 g). MS (−ve ion chemical ionisation) m/z 218 ([M−H]⁻, 100%).

Preparation 12 3,4-Dihydro-4-oxo-2-(4-pyridyl) pyrimidine-5-carboxylic acid

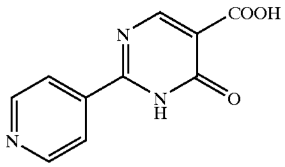

Ethyl 3,4-dihydro-4-oxo-2-(4-pyridyl)pyrimidine-5-carboxylate (M. Palanki, Bioorg. and Med. Chem. Lett., (2000), 10, 1645–8) was hydrolysed by the procedure of Preparation 11 (63%). NMR δ ($CD_3OD$) 8.27 (2H, d, J 7 Hz), 8.68 (2H, d, J 7 Hz), 8.91 (1H, s).

Preparation 13 Sodium 1-methyl-4-pyridone-3-carboxylate

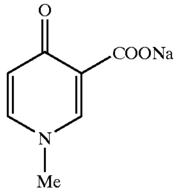

(a) Ethyl 1-methyl-4-pyridone-3-carboxylate—Ethyl 4-pyridone-3-carboxylate (M. Balogh et al., J. Het. Chem. (1980), 17(1), 359–368) (1.67 g) in DMP (15 ml) was treated with potassium carbonate (2.07 g) and iodomethane (0.625 ml) and stirred overnight. After filtration, the solution was evaporated and the residue chromatographed (eluent EtOH) to give title compound (1.2 g).

(b) Sodium 1-methyl-4-pyridone-3-carboxylate—Obtained by the procedure of Preparation 2 step (b). MS (+ve ion chemical ionisation) m/z 154 ($MH^+$, 25%), 110 (100%).

Preparation 14 6-Chloro-3-chloromethylpyridazine

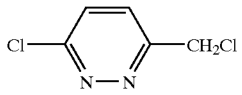

A suspension of 3-chloro-6-methylpyridazine (3 g), benzoyl peroxide (150 mg) and N-chlorosuccinimide (3.12 g) in $CCl_4$ (30 ml) was refluxed 16 hours, cooled, filtered and evaporated. Chromatography (EtOAc/hexane) gave title compound (1.67 g). NMR δ($CDCl_3$) 4.87 (2H, s), 7.58 (1H, d), 7.71 (1H, d).

Preparation 15 2-(Bis-t-butoxycarbonylamino)-4-pyridone-5-carboxylic acid

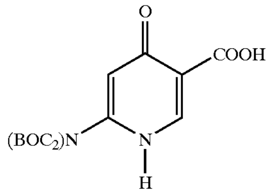

(a) Methyl 7-methoxy-tetrazolo[1,5-a]pyridine-6-carboxylate—A solution of methyl 6-chloro-4-methoxynicotinate (G. Lhommet and P. Maitte, C. R. Acad.Sci.Paris, series C, (1972), 275(21), 1317–18, prepared analogously) (4.52 g) in DMF (100 ml) was treated with sodium azide (2.92 g) and heated at 90° C. overnight. After evaporation, the residue was taken up in $CHCl_3$, filtered and the filtrate chromatographed (EtOAc/hexane 1:1) to give title compound (2.31 g). MS (+ve ion chemical ionisation) m/z 209 ($MH^+$ 100%).

(b Methyl 6-amino-4-methoxynicotinate—Material from step (a) (350 mg) with triphenylphosphine (490 mg) in chlorobenzene (5 ml) was heated to 135° C. for 1.5 hours and evaporated. The residue was dissolved in HOAc (8 ml)/water (2 ml), heated at 100° C. for 30 mins. and the solution evaporated. Chromatography (EtOAc) gave the title compound (306 mg).

(c) Methyl 2-amino-4-pyridone-5-carboxylate—The material from step (b) in conc. HI was heated to 85° C. for 48 hours and evaporated to dryness. The residue in methanol (10 ml) was treated with conc. $H_2SO_4$ (0.3 ml), refluxed overnight and evaporated to low volume. The residue was treated with excess aqueous $NaHCO_3$ and extracted several times with chloroform. The organic was dried and evaporated to give the title compound as a white solid (220 mg). MS (−ve ion chemical ionisation) m/z 167 ($[M-H]^-$, 100%).

(d) 2-(Bis-t-butoxycarbonylamino)-4-pyridone-5-carboxylic acid—Material from step (c) was converted by the procedure of Preparation 4 into title compound (366 mg). MS (−ve ion electrospray) m/z 353 ($[M-H]^-$, 70%), 179 (100%).

Preparation 16 3,4-Dihydro-3-methyl-4-oxopyrimidine-5-carboxylic acid

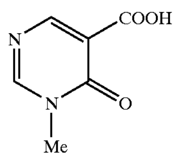

Ethyl 3,4-dihydro-4-oxopyrimidine-5-carboxylate was methylated by the procedure of Preparation 13 step (a) and hydrolysed by the procedure of Preparation 2, step (b). The aqueous solution was acidified to pH2 with 2N HCl, saturated with NaCl and extracted several times with $CHCl_3$. The organic solution was dried and evaporated to give title compound (60%). MS (−ve ion chemical ionisation) m/z 153 ($[M-H]^-$, 20%), 109 (100%).

Preparation 17 1,6-Dihydro-1-methyl-6-oxopyridazine-5-carboxylic acid

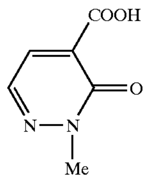

Made by the procedure of Preparation 16 from ethyl 3-pyridazinol-4-carboxylate (overall 74%). NMR δ($CDCl_3$) 3.97 (3H,s), 8.13 (1H, d, J 6.3 Hz), 8.19 (1H, d, J 6.3 Hz), 13.8 (1H, broad).

Preparation 18 1-(2-Bis-t-butoxycarbonylaminoethyl)-4-pyridone-3-carboxylic acid

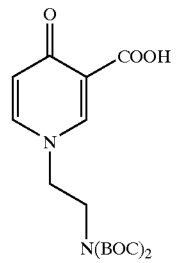

(a) Ethyl 1-(2-acetoxyethyl)-4-pyridone-3-carboxylate—A mixture of ethyl 4-pyridone-3-carboxylate (1.8 g), $K_2CO_3$ (2.5 g), 2-bromoethyl acetate (1.49 ml) and DMF (36 ml) was heated at 50° C. overnight, evaporated and the residue taken up in ethanol and filtered. After evaporation of the filtrate, the crude was chromatographed (EtOAc/EtOH 1:1) to give title compound (1.66 g). MS (+ve ion chemical ionisation) m/z 254 ($MH^+$, 100%).

(b) Ethyl 1-(2-hydroxyethyl)-4-pyridone-3-carboxylate—Material from step (a) (1.64 g) in ethanol (30 ml) was kept 5 hours with a catalytic amount of NaOEt, evaporated to low volume, added to a silica column and eluted with ethanol to give title compound (1.2 g). MS (+ve ion chemical ionisation) m/z 212 ($MH^+$, 100%).

(c) Ethyl 1-(2-bis-t-butoxycarbonylaminoethyl)-4-pyridone-3-carboxylate—Material from step (b) (211 mg), triphenylphosphine (394 mg) and $(BOC)_2NH$ (326 mg) in THF (5 ml) were treated with diethyl azodicarboxylate (0.246 ml), stirred 30 mins. and the solution evaporated. The residue was chromatographed (EtOH/EtOAc) to give title compound (153 mg). MS(+ve ion chemical ionisation m/z 411 ($MH^+$, 100%).

(d) 1-(2-Bis-t-butoxycarbonylaminoethyl)-4-pyridone-3-carboxylic acid—Material from step (c) was hydrolysed by the procedure of Preparation 4 step (b) to give title compound (86%). MS(−ve ion electropsray) m/z 381 ($[M-H]^-$, 10%), 138 (100%).

Preparation 19 7-(4-(t-Butyloxycarbonyl)piperazin-1-yl)-1-ethyl-4-oxo-1,4-dihydro-6,8-diazaquinoline-3-carboxylic acid

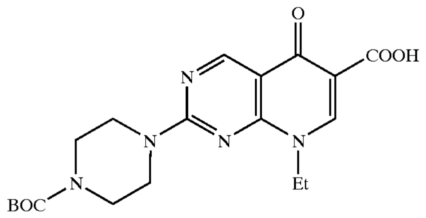

7-(1-Piperazinyl)-1-ethyl-4-oxo-1,4-dihydro-6,8-diazaquinoline-3-carboxylic acid (607 mg) in dichloromethane (20 ml) was heated with triethylamine (405 mg) and di-tert-butyldicarbonate (873 mg). The mixture was stirred overnight at ambient temperature then oncentrated in vacuo. The product was collected by filtration, washed with hexane and dried in vacuo to give a white solid (682 mg). MS (−ve ion electrospray) m/z 402 ($[M-H]^-$, 100%).

Preparation 20 4-Oxo-1,4-dihydropyrido[2,3-c]pyridazine-3-carboxylic acid

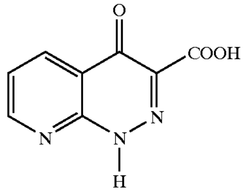

(a) 3-(2-Chloropyridin-3-yl)-2-diazo-3-oxopropionic acid ethyl ester—2-Chloronicotinoyl chloride (10 g) and ethyl diazoacetate (19.4 g) were heated together at 55° C. for 3 hours then left at ambient temperature for 18 hours. The mixture was concentrated in vacuo and the residue chromatographed on silica gel, eluting with 30–50% ethyl acetate in hexane. This gave the title compound (9.08 g, 63%). NMR ($CDCl_3$) δ1.15 (3H, t), 4.15 (2H, q), 7.25 (1H, t), 7.58 (1H, dd), 8.48 (1H, dd).

(b) 4-Oxo-1,4-dihydropyrido[2,3-c]pyridazine-3-carboxylic acid ethyl ester—3-(2-Chloropyridin-3-yl)-2-diazo-3-oxopropionic acid ethyl ester (5 g) in diisopropyl ether (150 ml) was treated with triphenylphosphine (5.7 g) and stirred at ambient temperature for 18 hours. The resulting solid was filtered off and dried in vacuo then treated with methanol (250 ml) and water (50 ml) and heated under reflux for 2 hours. The methanol was distilled off and the resulting aqueous extracted with EtOAc. The organic was dried and evaporated. Chromatography (EtOAc/hexane) gave title compound (3.2 g). MS (−ve ion chemical ionisation) m/z 218 ($[M-H]^-$, 100%).

(c) 4-Oxo-1,4-dihydropyrido[2,3-c]pyridazine-3-carboxylic acid—Material from step (b) was hydrolysed by the procedure of Preparation 10 to give title compound (62%). MS (+ve ion electrospray) m/z 192 ($MH^+$, 65%).

Preparation 21 3-Methoxy-2-nitropyridine-6-carboxaldehyde

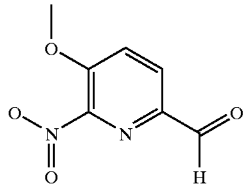

A mixture of 3-methoxy-6-methyl-2-nitropyridine (S. Lindstrom, T. Ahmad and S. Grivas, Heterocycles (1994), 38(3), 529–540) (30 mmole) and N-bromosuccinimide (60 mmole) in $CCl_4$ (50 ml) was refluxed under a 500 watt tungsten lamp for 16 hours, cooled, filtered and evaporated. A portion (2.4 g) of the crude product was mixed with sodium formate (1 g), water (1 ml) and ethanol (7 ml), refluxed for 24 hours, cooled and concentrated to low volume. The residue was partitioned between dichloromethane and water, the organic dried and evaporated. Chromatography gave the title compound (25%).

Pyrazolo[1,5-a]pyrimidine carboxylic acid was obtained from Chembridge. 2,3-Dihydro-5-oxothiazolo[3,2-a]pyrimidine-6-carboxylic acid was obtained from Maybridge Chemical Co. Ltd. 2-Oxopyran-3-carbonyl chloride was prepared by the method of G. H. Posner, J. Org. Chem., 60, (1995) 4617–28.

1,4-Dihydro-6-methyl-4-oxopyridazine-3-carboxylic acid was prepared according to I. Ichimoto, K. Fujii and C. Tatsumi, Agric. Biol. Chem. (1967), 31, 979.

4-Methoxynicotinic acid was prepared according to W. Ross, J. Chem. Soc.C, (1966), 1816.

Example 1

(2,4-Dihydroxypyrimidine-5-carboxylic acid) mutilin 14-ester

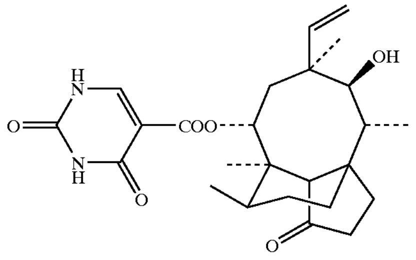

(a) (2,4-Dihydroxypyrimidine-5-carboxylic acid)(3R)-3-deoxo-11-deoxy-3-methoxy-11-oxo-4-epimutilin 14-ester—A solution of (3R)-3-deoxo-11-deoxy-3-methoxy-11-oxo-4-epimutilin (334 mg) in DMF (2 ml) was treated with 2,4-dihydroxypyrimidine-5-carbonyl chloride mono DMF complex half hydrochloride (266 mg)(O. Miyashita, K. Matsumura, T. Kasahara, H. Shimadzu and N. Hashimoto, Chem. Pharm. Bull. (1982),30, 887–898) and heated at 110° C. for 6 hours. The solution was cooled, diluted with EtOAc (20 ml), washed with water (3×20 ml), dried and evaporated. Chromatography, eluting with EtOAc/hexane, gave the title compound as a foam (60 mg). MS (−ve ion electrospray) m/z 471 ($[M-H]^-$, 100%).

(b) (2,4-Dihydroxypyrimidine-5-carboxylic acid) mutilin 14-ester—The product of step (a) above was dissolved in dioxan (3 ml), treated with conc. HCl (1.5 ml) and kept 5 hours. EtOAc (10 ml) and water (10 ml) were added, followed by solid $NaHCO_3$ until basic. The layers were shaken, separated and the organic dried and evaporated. The solid was triturated under dichloromethane and filtered to give the title compound (48 mg). MS (−ve ion electrospray) m/z 457 ($[M-H]^-$, 100%).

Examples 2–7 were prepared analogously to Example 1. Acid chlorides were prepared by refluxing the carboxylic acids or Na salts in thionyl chloride for periods of between 2 and 24 hours, evaporation to dryness and desiccation under vacuum. Products of step (b) were in some cases chromatographed.

Step (a)
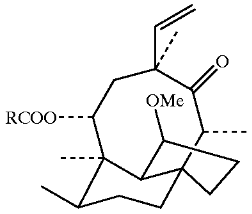
| Example No | R | yield (%) | MS (−ve ion electrospray) m/z |
|---|---|---|---|
| 2 | 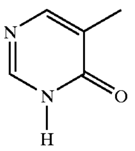 | 21 | 455 ([M − H]$^-$, 100%) |
| 3 | 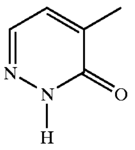 | 25 | 455 ([M − H]$^-$, 100%) |
| 4 | 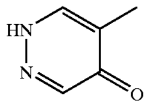 | 30 | 455 ([M − H]$^-$, 100%) |
| 5 | 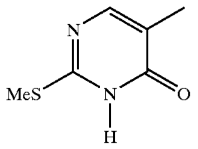 | 54 | 501 ([M − H]$^-$, 100%) |
| 6 | 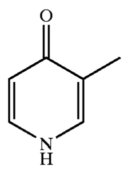 | 47 | 454 ([M − H]$^-$, 25%), 138 (100%) |
| 7 | 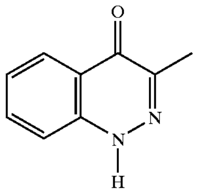 | 14 | 505 ([M − H]$^-$, 100%) |
Step (b)
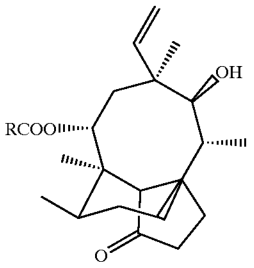
| Example No. | R | yield (%) | MS (−ve ion electrospray) m/z |
|---|---|---|---|
| 2 | 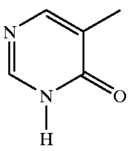 | 100 | 441 ([M − H]$^-$, 100%) |
| 3 | 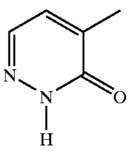 | 100 | 441 ([M − H]$^-$, 40%), 139 (100%) |
| 4 | 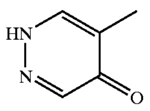 | 100 | 441 ([M − H]$^-$, 100%) |
| 6 | 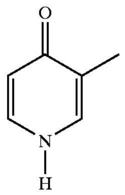 | 92 | 440 ([M − H]$^-$, 10%), 138 (100%) |
| 7 | 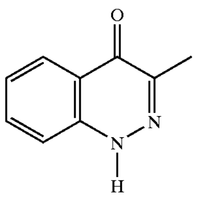 | 73 | 491 ([M − H]$^-$, 100%) |

Example 8

(7-Methylthio-4-oxo-1,4-dihydropyrimido[4,5-c]pyridazine-3-carboxylic acid) 19,20-dihydromutilin 14-ester

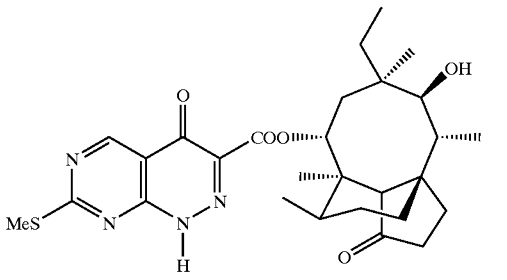

(a) (7-Methylthio-4-oxo-1,4-dihydropyrimido[4,5-c]pyridazine-3-carboxylic acid) (3R)-3-deoxo-11-deoxy-19,20-dihydro-3-methoxy-11-oxo-4-epimutilin14-ester—7-Methylthio-4-oxo-1,4-dihydropyrimido[4,5-c]pyridazine-3-carboxylic acid (Y. Kimura, Chem.Pharm.Bull., (1976), 24(11), 2637) was converted into acid chloride by reflux in thionyl chloride and evaporation to dryness. This was reacted with (3R)-3-deoxo-11-deoxy-19,20-dihydro-3-methoxy-11-oxo-4-epimutilin (produced by atmospheric pressure hydrogenation of (3R)-3-deoxo-11-deoxy-3-methoxy-11-oxo-4-epimutilin with 10% Pd/C in ethanol) by the procedure of Example 1, step (a) to give title compound (31%). MS (−ve ion electrospray) m/z. 555 ([M−H]$^-$, 100%).

(b) (7-Methylthio-4-oxo-1,4-dihydropyrimido[4,5-c]pyridazine-3-carboxylic acid) 19,20-dihydromutilin 14-ester—Material from step (a) was rearranged by the procedure of Example 1 step (b) to give title compound (82%). MS (−ve ion electrospray) m/z 541 ([M−H]$^-$, 100%).

Example 9

Nalidixic Acid Mutilin 14-Ester

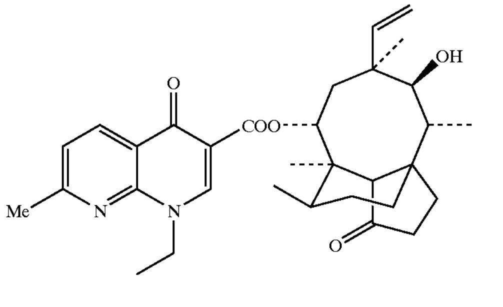

(a) Nalidixic acid (3R)-3-deoxo-11-deoxy-3-methoxy-11-oxo-4-epimutilin 14-ester A suspension of nalidixic acid (232 mg) in dichloromethane (5 ml) was treated with 1 drop of DMF and oxalyl chloride (0.1 ml), stirred for 15 minutes and evaporated. Toluene (5 ml) was added and evaporated and the residue redissolved in dichloromethane (5 ml). (3R)-3-Deoxo-11-deoxy-3-methoxy-11-oxo-4-epimutilin (100 mg) and $Ag_2O$ (464 mg) were added and the mixture stirred overnight at room temp. and filtered through kieselguhr. Chromatography of material contained in the filtrate, eluting with EtOAc/hexane, gave the title compound as a foam (65 mg). MS (+ve ion electrospray) m/z 571 (MNa$^+$, 15%), 549 (MH$^+$, 55%), 233 (100%).

(b) Nalidixic acid mutilin 14-ester—Nalidixic acid (3R)-3-deoxo-11-deoxy-3-methoxy-11-oxo-4-epimutilin 14-ester was treated as in Example 1, step (b) to give the title compound as a white solid (86%). MS (+ve ion electrospray) m/z 535(MH$^+$, 15%), 233(100%).

Example 10

1-Methyl-4-pyridone-3-carboxylic acid) mutilin 14-ester

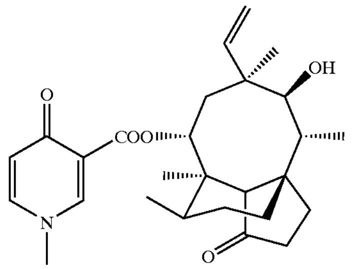

Sodium 1-methyl-4-pyridone-3-carboxylate (175 mg) in thionyl chloride (4 ml) was refluxed overnight, evaporated to dryness and the residue dried under vacuum. The resulting acid chloride was esterified by the procedure of Example 9 step (a) (16%) and rearranged by the procedure of Example 1 step (b) to give title compound (98%). MS (+ve ion electrospray) m/z 456 (MH$^+$, 25%), 154 (100%).

Example 11

(2-Oxo-1,2-dihydropyrazine-3-carboxylic acid) mutilin 14-ester

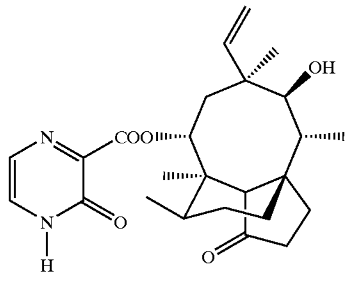

2-Oxo-1,2-dihydropyrazine-3-carboxylic acid (A. Krapcho. et. al., J. Het. Chem. (1997), 34, 27–32) (1 g) was refluxed in thionyl chloride (20 ml) for 3 hours and evaporated to dryness. The resulting acid chloride was esterified by the procedure of Example 9, step (a) (16%) and rearranged by the procedure of Example 1 step (b) to give title compound (100%). MS (−ve ion electrospray) m/z 441 ([M−H]$^-$, 100%).

Example 12

(2,4-Dihydroxypyrimidine-5-carboxylic acid)(3R)-3-deoxo-11-deoxy-3-methoxy-11-oxo-4-epimutilin 14-ester A solution of (3R)-3-deoxo-11-deoxy-3-methoxy-11-oxo-4-epimutilin (170 mg) in dichloromethane (5 ml) was treated with $Ag_2O$ (348 mg) and 2,4-dihydroxypyrimidine-5-carbonyl chloride mono DMF complex half hydrochloride (266 mg) and stirred for 3 days. The mixture was filtered and the filtrate evaporated to give the title compound mixed with an equimolar amount of (3R)-3-deoxo-11-deoxy-3-methoxy-11-oxo-4-epimutilin (220 mg).

Example 13

(2,4-Dihydroxypyrimidine-5-carboxylic acid)(2S)-2-hydroxymutilin 14-ester

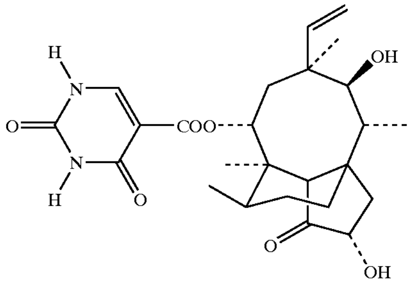

(a) (2,4-Dihydroxypyrimidine-5-carboxylic acid)(2S)-2-dichloroacetoxy-11-O-trifluoroacetylmutilin 14-ester—A solution of (2S)-2-dichloroacetoxy-11-O-trifluoroacetylmutilin 14-ester (271 mg) in dichloromethane (10 ml) was treated with silver oxide (700 mg) and 2,4-dihydroxypyrimidine-5-carbonyl chloride mono DMF complex half hydrochloride (see Example 1)(532 mg) and stirred for 1 week at room temp. The mixture was filtered and the solid washed with dichloromethane (10 ml). The title compound was not found in the filtrate, but was obtained by washing the solid with ethanol (2×10 ml). Evaporation of ethanol, dissolving the residue in EtOAc and filtration of this solution through silica followed by evaporation gave the title compound as a white solid (22 mg). MS (−ve ion electrospray) m/z 679 ($[M-H]^-$, 35%), 437(100%).

(b) (2,4-Dihydroxypyrimidine-5-carboxylic acid)(2S)-2-hydroxymutilin 14-ester—The product from step (a) (22 mg) was suspended in ethanol (5 ml) and treated dropwise with 0.5N KOH (0.128 ml). After 15 minutes the resulting solution was treated with saturated aqueous $NaHCO_3$ (4 ml) and stirred vigorously for 2 hours. EtOAc (15 ml) and water (15 ml) were added, the layers shaken and separated. The aqueous was re-extracted with EtOAc (15 ml) and the combined organic dried and evaporated to give the title compound as a white solid (10 mg). MS (−ve ion electrospray) m/z 473 ([M−H]−, 75%), 155 (100%).

Example 14

(3-Pyridazinol-4-carboxylic acid) mutilin 14-ester

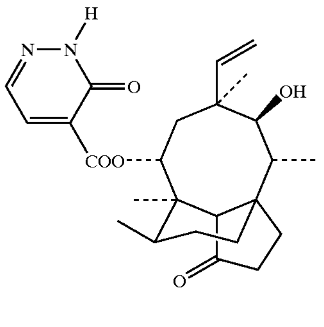

(a) (3-Pyridazinol-4-carboxylic acid) (3R)-3-deoxo-11-deoxy-3-methoxy-11-oxo-4-epimutilin 14-ester A suspension of sodium 3-pyridazinol-4-carboxylate (324 mg) in dichloromethane (15 ml) was treated with 1 drop of DMF and oxalyl chloride (0.262 ml), stirred for 0.5 hour and the solvent evaporated. Benzene (15 ml) was added and evaporated and the residue taken up in dichloromethane (15 ml). Silver cyanate (600 mg) and (3R)-3-deoxo-11-deoxy-3-methoxy-11-oxo-4-epimutilin (668 mg) were added and the mixture stirred at room temp. under argon for 18 hours and filtered through kieselguhr. Chromatography of material contained in the filtrate, eluting with EtOAc/hexane, gave the title compound (200 mg) as a foam. MS (−ve ion electrospray) m/z 455($[M-H]^-$, 100%).

(b) (3-Pyridazinol-4-carboxylic acid) mutilin 14-ester

A solution of (3-pyridazinol-4-carboxylic acid) (3R)-2-deoxo-11-deoxy-3-methoxy-11-oxo-4-epimutilin 14-ester (287 mg) in dioxan (8 ml) was treated dropwise with conc. HCl (4 ml) and left overnight at room temp. The mixture was diluted with chloroform (15 ml) and water (15 ml) and treated with solid $NaHCO_3$ until basic. The layers were shaken and separated, the organic dried over $MgSO_4$ and evaporated. Chromatography (EtOAc/hexane) gave the title compound as a white solid (230 mg). MS (−ve ion electrospray) m/z 441 ($[M-H]^-$, 40%), 139 (100%).

Example 15

Nalidixic acid (3R)-3-deoxo-11-deoxy-3-methoxy-11-oxo-4-epimutilin 14-ester

Using conditions analogous to those of Example 14, the title compound was obtained in 16% yield, identical to the product of Example 9, step (a).

Example 16

(2,4-Dihydroxypyrimidine-5-carboxylic acid) (3R)-3-deoxo-11-deoxy-3-methoxy-11-oxo-4-epimutilin 14-ester Using conditions similar to those of Example 14, the title compound was obtained in 47% yield, identical to the product of Example 1, step (a).

Example 17

(4-Ethoxyquinoline-3-carboxylate) mutilin 14-ester

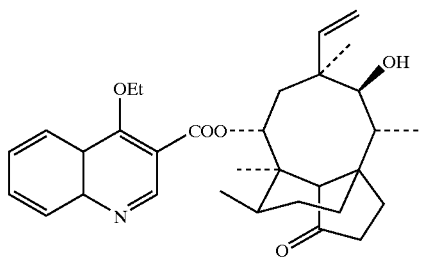

(a) (4-Chloroquinoline-3-carboxylate)(3R)-3-deoxo-11-deoxy-3-methoxy-11-oxo-4-epimutilin 14-ester A suspension of 4-quinolone-3-carboxylic acid (189 mg) in dichloromethane (5 ml) was treated with 1 drop DMF and oxalyl chloride (0.2 ml), stirred 1.5 hours and the solvent evaporated. The residue was briefly put under vacuum to provide 4-chloroquinoline-3-carbonyl chloride as a white solid.

A solution of (3R)-3-deoxo-11-deoxy-3-methoxy-11-oxo-4-epimutilin (334 mg) in THF (5 ml) at −20° C. under argon was treated with a 1M solution of sodium hexamethyldisilazide in THF (1 ml), stirred 15 minutes and treated with the above 4-chloroquinoline-3-carbonylchloride. The mixture was stirred at room temp. overnight, diluted with EtOAc (30 ml), washed with water (30 ml), dried and evaporated. Chromatography (EtOAc/hexane) gave a 1:1 mixture of the title compound with (3R)-3-deoxo-11-deoxy-3-methoxy-11-oxo-4-epimutilin (227 mg). MS (+ve ion electrospray) m/z 524 ($MH^+$, 3%), 208 (100%).

(b) (4-Ethoxyquinoline-3-carboxylate) (3R)-3-deoxo-11-deoxy-3-methoxy-11-oxo-4-epimutilin 14-ester A solution of the product from step (a) (227 mg) in ethanol (3 ml) was treated with 0.5M KOH in EtOH (1 ml) and stirred 6 hours. EtOAc (20 ml) was added, the solution was washed with water (20 ml), dried and evaporated. Chromatography (EtOAc/hexane) gave the title compound (137 mg). MS (+ve ion electrospray) m/z 534 ($MH^+$, 100%).

(c) (4-Ethoxyquinoline-3-carboxylate) mutilin 14-ester

The product of step (b) was rearranged according to the procedure of Example 14, step (b) to provide the title compound as a foam (105 mg). MS (+ve ion electrospray) m/z 520 ($MH^+$, 5%), 218 (100%).

Example 18

(4-Hydroxynicotinic acid) mutilin 14-ester

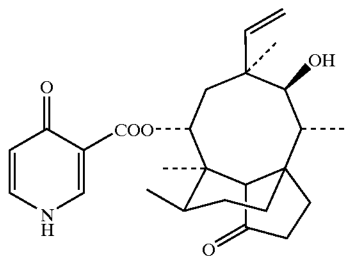

(a) (4-Hydroxynicotinic acid)(3R)-3-deoxo-11-deoxy-3-methoxy-11-oxo-4-epimutilin 14-ester A suspension of calcium 4-hydroxynicotinate (79 mg) (Specs and Biospecs B.V.) in dichloromethane (2.5 ml) was treated with 1 drop of DMF and oxalyl chloride (0.13 ml), stirred 3 hours and evaporated. Benzene (5 ml) was added and evaporated to provide an acid chloride. A solution of (3R)-3-deoxo-11-deoxy-3-methoxy-11-oxo-4-epimutilin (167 mg) in THF (5 ml) at −78° C. under argon was treated with 2.5M n-BuLi in hexane (0.22 ml), left 15 minutes and added to the above acid chloride. The mixture was stirred at room temp. overnight, treated with saturated aqueous $NaHCO_3$ (20 ml) and then EtOAc (20 ml), and the layers shaken and separated. The organic was dried and evaporated. Chromatography (EtOAc/hexane) gave the title compound (23 mg) as a white solid. MS (−ve ion electrospray) m/z 454($[M-H]^-$, 25%), 138 (100%).

(b) (4-Hydroxynicotinic acid) mutilin 14-ester

The product of step (a) was rearranged according to the procedure of Example 14, step (b) to provide the title compound as a white solid (20 mg). MS (−ve ion electrospray) m/z 440($[M-H]^-$, 10%), 138 (100%).

The following were prepared in a similar manner to step (a) of Example 18:

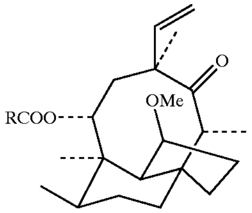

| Example no. | R | % yield | MS (m/z) |
|---|---|---|---|
| 19 | 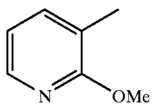 | 48 | (+ve ion C.I.) 470 $MH^+$, 40%), 285 (100%) |
| 20 | 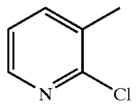 | 56 | (+ve ion C.I.) 474 ($MH^+$, 100%) |
| 21 | 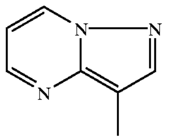 | 3 | (−ve ion C.I.) 510 ($[M + OMe]^-$, 100%) 478 ($[M - H]^-$, 70%) |
| 22 | 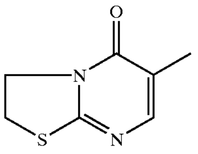 | 32 | (−ve ion electrospray) 573 ($MOAc^-$, 100%) |
| 23 | 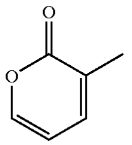 | 16 | (+ve ion electrospray) 479 ($MNa^+$, 40%), 163 (100%) |
| 24 | 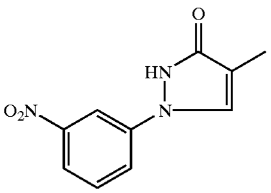 | 2 | (−ve ion electrospray) 564 ($[M - H]^-$, 10%), 333 (100%) |
| 25 | 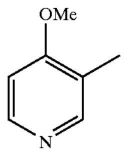 | 34 | (+ve ion electrospray) 470 ($MH^+$, 5%), 154 (100%). |

Example 19

(b) (2-Methoxynicotinic acid) mutilin 14-ester and (2-hydroxynicotinic acid) mutilin 14-ester

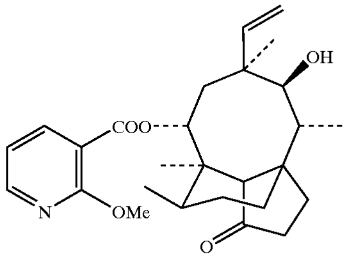

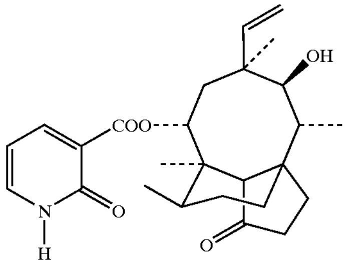

The product of Example 19, step (a) was rearranged according to the procedure of Example 14, step (b) to give the two title compounds.

(2-Methoxynicotinic acid) mutilin 14-ester (15%): MS (+ve ion chemical ionisation) m/z 456 ($MH^+$, 20%), 285 (100%).

(2-Hydroxynicotinic acid) mutilin 14-ester (37%): MS (−ve ion electrospray) m/z 440 ($[M-H]^-$, 100%).

The following were prepared in a similar manner to step (b) of Example 14:

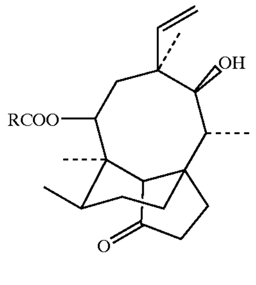

| Example no. | R | % yield | MS (m/z) |
|---|---|---|---|
| 21 | 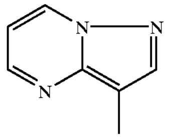 | 98 | (+ve ion electrospray) 488 ($MNa^+$, 60%), 227 (100%) |
| 22 | 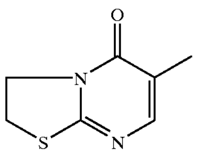 | 100 | (−ve ion electrospray) 559 ($MOAc^-$, 100%) |

-continued

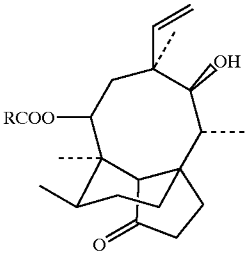

| Example no. | R | % yield | MS (m/z) |
|---|---|---|---|
| 23 | 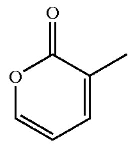 | 55 | (+ve ion electrospray) 465 ($MNa^+$, 30%), 163 (100%) |
| 24 | 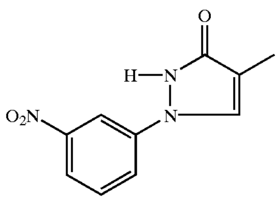 | 100 | (−ve ion electrospray) 550 ($[M-H]^-$, 65%), 248 (100%) |
| 25 | 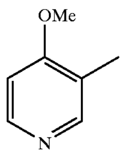 | 100 | (+ve ion electrospray) 456 ($MH^+$, 7%), 154 (100%). |

Example 26

(4-Quinolone-3-carboxylic acid) mutilin 14-ester

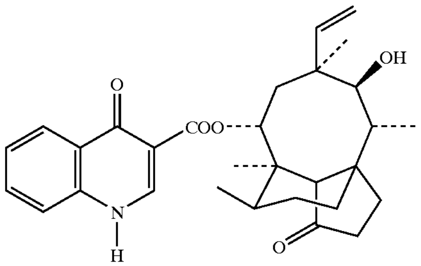

(a) (4-Quinolone-3-carboxylic acid)(3R)-3-deoxo-11-deoxy-3-methoxy-11-oxo-4-epimutilin 14-ester An ice-cooled suspension of 4-quinolone-3-carboxylic acid (189 mg) in dichloromethane (5 ml) was treated with triethylamine (0.139 ml) and (3R)-14-O-chlorocarbonyl-3-deoxo-11-deoxy-3-methoxy-11-oxo-4-epimutilin (200 mg) (Example 12 from U.S. Pat. No. 6,020,368, July 2000). After 15 minutes, 4-dimethylaminopyridine (60 mg) was added and the solution left 3 days at room temp., washed with 0.5N HCl (10 ml) and saturated $NaHCO_3$ solution (10 ml), dried and evaporated. The material obtained was a mixture of (3R)-3-deoxo-11-deoxy-3-methoxy-11-oxo-4-epimutilin with the title compound. MS (−ve ion electrospray) m/z 504 ($[M-H]^-$, 100%).

(b) (4-Quinolone-3-carboxylic acid) mutilin 14-ester

The material from step (a) in dioxan (10 ml) was treated with conc. HCl (5 ml) and left overnight. The solution was diluted with EtOAc (20 ml) and water (20 ml) and treated with solid $NaHCO_3$ until basic. The layers were shaken and separated, the organic dried and evaporated. The residue was triturated under ether and the white solid filtered off and washed with ether to give the title compound (35 mg). MS (−ve ion electrospray) 490 ($[M-H]^-$, 100%).

Example 27

(2-Amino-4-hydroxypyrimidine-5-carboxylic acid) mutilin 14-ester

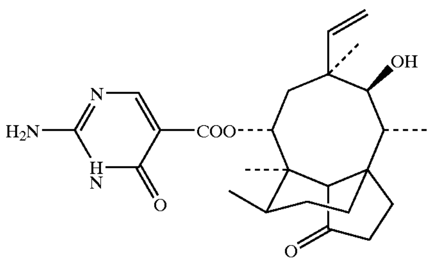

(a) BOC derivatives of (2-amino-4-hydroxypyrimidine-5-carboxylic acid) (3R)-3-deoxo-11-deoxy-3-methoxy-11-oxo-4-epimutilin 14-ester The product from preparation 4 (355 mg) in dichloromethane (5 ml) was ice-cooled, treated with triethylamine (0.139 ml) and (3R)-14-O-chlorocarbonyl-3-deoxo-11-deoxy-3-methoxy-11-ox-4-epimutilin (396 mg) and stirred for 6 hours, while allowing to warm to room temp. 4-Dimethylaminopyridine (60 mg) was added and the mixture left for 3 days, added to silica column and eluted with EtOAc/hexane to obtain the title compounds as a foam (174 mg). MS (+ve ion electrospray) m/z 572 ($MH^+$ for mono BOC derivative, 20%), 256 (100%).

(b) (2-Amino-4-hydroxypyrimidine-5-carboxylic acid) mutilin 14-ester

A solution of the product from step (a) in dioxan (5 ml) was treated with conc. HCl (2.5 ml) and left overnight. EtOAc (10 ml) and water (10 ml) were added, followed by solid $NaHCO_3$ until basic. A further 500 ml EtOAc were added and the layers shaken and separated. The organic was dried and evaporated and the residue crystallised from hot ethanol (10 ml). The solid was filtered off and the filtrate evaporated to provide the title compound as a white solid (55 mg after trituration under ether). MS (−ve ion electrospray) m/z 456 ($[M-H]^-$, 100%).

Example 28

[3,4-Dihydro-2-dimethylamino-4-oxopyrimidine-5-carboxylic acid] mutilin 14-ester (a) [3,4-Dihydro-2-dimethylamino-4-oxopyrimidine-5-carboxylic acid] (3R)-3-deoxo-11-deoxy-3-methoxy-11-oxo-4-epimutilin 14-ester 3,4-Dihydro-2-dimethylamino-4-oxopyrimidine-5-carboxylic acid (92 mg) in dichloromethane (3 ml) was ice-cooled, treated with triethylamine (0.07 ml) and (3R)-14-O-chlorocarbonyl-3-deoxo-11-deoxy-3-methoxy-11-oxo-4-epimutilin (198 mg) and stirred overnight, allowing to warm to room temp. The solution was again ice-cooled, treated with 4-dimethylaminopyridine (30 mg) and stirred overnight, allowing to warm to room temp. The mixture was added to a silica column and eluted with 40% EtOAc/hexane to give title compound (158 mg). MS (−ve ion electrospray) m/z 498 ($[M-H]^-$, 100%).

(b) [3,4-Dihydro-2-dimethylamino-4-oxopyrimidine-5-carboxylic acid] mutilin 14-ester Material from step (a) was rearranged by the procedure of Example 14 step (b) (94%). MS (−ve ion electrospray) m/z 484 ($[M-H]^-$, 100%).

Examples 29–43 Step (a)

The following were prepared analogously to step (a) of Example 28:

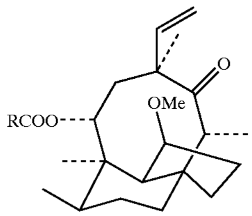

| Example no. | R | % Yield MS (m/z) |
|---|---|---|
| 29 | 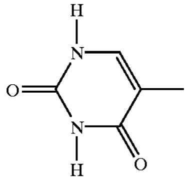 | 9 |

-continued
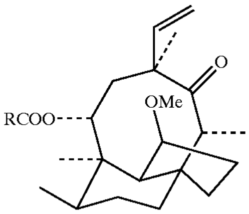
| Example no. | R | % Yield | MS (m/z) |
|---|---|---|---|
| 30 | 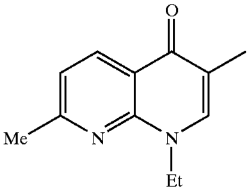 | 53 | |
| 31 | 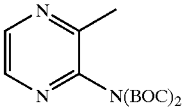 | 29 | (+ve ion electrospray) 678 ($MNa^+$, 100%) |
| 32 | 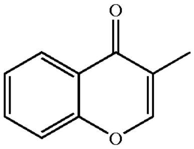 | 37 | |
| 33 | 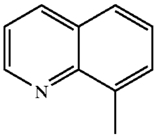 | 54 | (+ve ion electrospray) 512 ($MNa^+$, 20%), 156 (100%) |
| 34 | 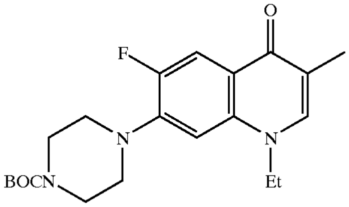 | 37 | (+ve ion electrospray) 735 ($MH^+$, 12%), 420 (100%) |
| 35 | 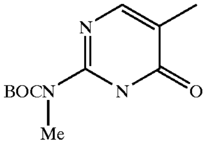 | 44 | (−ve ion electrospray) 584 ($[M-H]^-$, 100%) |
| 36 | 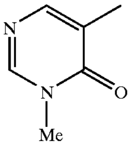 | 37 | (+ve ion electrospray) 963 ($2MNa^+$, 100%), 493 ($MNa^+$, 60%) |
| 37 | 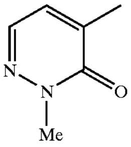 | 58 | (+ve ion electrospray) 493 ($MNa^+$, 35%), 177 (100%) |

-continued
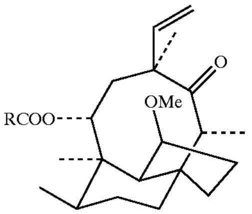
| Example no. | R | % Yield | MS (m/z) |
|---|---|---|---|
| 38 | 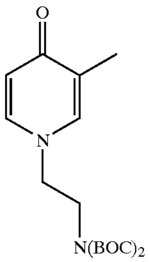 | 53 | (−ve ion electrospray) 757 (MOAc⁻, 100%) |
| 39 | 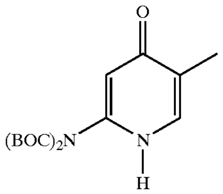 | 39 | (−ve ion electrospray) 669 ([M − H]⁻, 100%) |
| 40 | 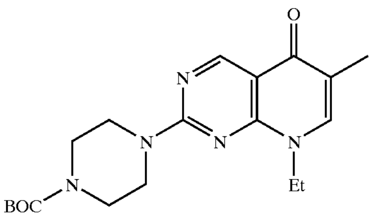 | 15 | |
| 41 | 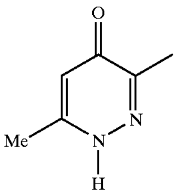 | 21 | (−ve ion electrospray) 469 ([M − H]⁻, 100%) |
| 42 | 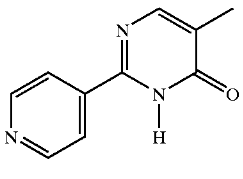 | 34 | (−ve ion electrospray) 532 ([M − H]⁻, 100%) |
| 43 | 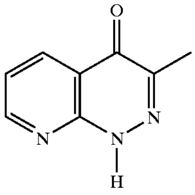 | 48 | (−ve ion electrospray) 506 ([M − H]⁻, 100%) |

Examples 31–43 Step (b)

The following were prepared analogously to step (b) of Example 14:

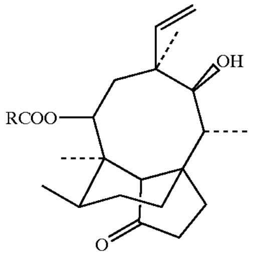

| Example no. | R | % yield | MS (m/z) |
|---|---|---|---|
| 31 | 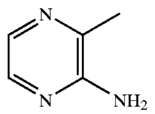 | 76 | (+ve ion C.I.) 442 ($MH^+$, 10%) 303 (100%) |
| 32 | 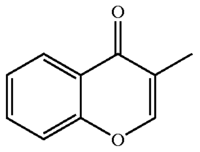 | 72 | (+ve ion electrospray) 515 ($MNa^+$, 60%), 254 (100%) |
| 33 | 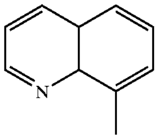 | 83 | (+ve ion electrospray) 498 ($MNa^+$, 50%), 156 (100%) |
| 34 | 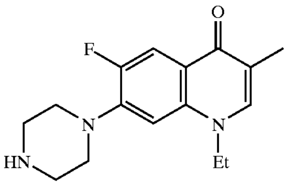 | 75 | (+ve ion electrospray) 622 ($MH^+$, 40%), 320 (100%) |
| 35 | 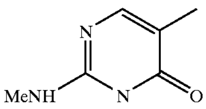 | 100 | (−ve ion electrospray) 470 ($[M-H]^-$, 100%) |
| 36 | 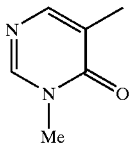 | 100 | (+ve ion electrospray) 935 ($2MNa^+$, 100%), 457 ($MH^+$, 5%) |
| 37 | 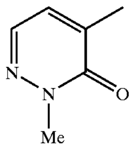 | 98 | (+ve ion electrospray) 520 ($MNa[MeCN]^+$, 100%), 479 ($MNa^+$, 30%) |

-continued

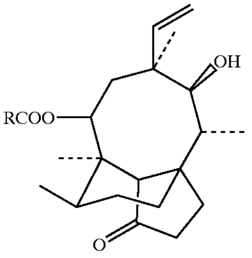

| Example no. | R | % yield | MS (m/z) |
|---|---|---|---|
| 38 | 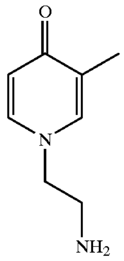 | 100 | (−ve ion electrospray) 543 ($MOAc^-$, 100%) |
| 39 | 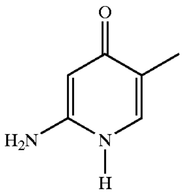 | 100 | (−ve ion electrospray) 455 ($[M-H]^-$, 70%), 153 (100%) |
| 40 | 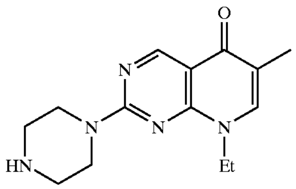 | 76 | (−ve ion electrospray) 606 ($[M-H]^-$, 100%) |
| 41 | 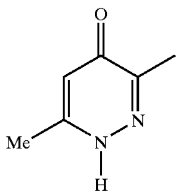 | 100 | (−ve ion electrospray) 455 ($[M-H]^-$, 100%) |
| 42 | 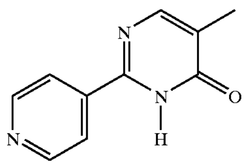 | 39 | (−ve ion electrospray) 518 ($[M-H]^-$, 100%) |
| 43 | 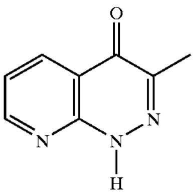 | 95 | (−ve ion electrospray) 492 ($[M-H]^-$, 100%) |

Example 44

(3,4-Dihydro-2-dimethylamino-4-oxopyrimidine-5-carboxylic acid)-(2S)-2-hydroxymutilin 14-ester

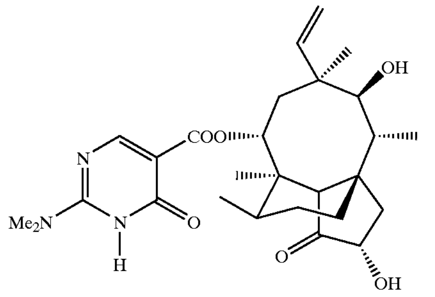

(a) (3,4-Dihydro-2-dimethylamino-4-oxopyrimidine-5-carboxylic acid)-(2S)-2-dichloroacetoxy-11-trifluoroacetylmutilin 14-ester Prepared from 14-O-chloroacarbonyl-(2S)-2-dichloroacetoxy-11-O-trifluoroacetylmutilin by the procedure of Example 28 step (a) (39%). MS (−ve ion electrospray) m/z 706 ($[M-H]^-$, 100%).

(b) (3,4-Dihydro-2-dimethylamino-4-oxopyrimidine-5-carboxylic acid)-(2S)-2-hydroxymutilin 14-ester Material from step (a) was deprotected by the procedure of Example 13, step (b) and chromatographed to give title compound (36%). MS (−ve ion electrospray) m/z 500 ($[M-H]^-$, 60%), 182 (100%).

Example 45

Nalidixic acid (3R)-3-deoxo-11-deoxy-3-methoxy-11-oxo-4-epimutilin 14-ester

A suspension of nalidixic acid (232 mg) in dichloromethane (4.5 ml) was treated with a 20% solution of phosgene in toluene (0.53 ml) and stirred 5 hours at room temp. (3R)-3-deoxo-11-deoxy-3-methoxy-11-oxo-4-epimutilin (167 mg) was added and stirring continued overnight. The mixture was filtered and the filtrate evaporated to provide a crude product shown by NMR to contain a substantial amount of the title compound (by comparison with the product of Example 9, step (a).

This reaction is also successful using DMF as solvent instead of dichloromethane.

Example 46

Nalidixic acid (2S)-2-dichloroacetoxy-11-O-trifluoroacetylmutilin 14-ester

A suspension of nalidixic acid (232 mg) in DMF (4 ml) was ice-cooled, treated with 20% phosgene in toluene (0.53 ml) and stirred for 3 hours. (2S)-2-Dichloroacetoxy-11-O-trifluoroacetylmutilin (200 mg) was added and the mixture stirred for 48 hours at room temp., diluted with EtOAc (30 ml), washed with saturated aqueous $NaHCO_3$ (20 ml) and water (3x20 ml), dried and evaporated. Chromatography (EtOAc/hexane) gave the title compound mixed with nalidixic acid 1,2-didehydro-11-O-trifluoroacetylmutilin 14-ester (137 mg). MS (+ve ion electrospray) m/z 757 ($MH^+$, 10%), 233 (100%).

Example 47

Nalidixic acid (3R)-3-deoxo-11-deoxy-3-methoxy-11-oxo-4-epimutilin 14-ester

Nalidixic acid chloride (1 mmole) was prepared as in Example 9, taken up in dichloromethane (5 ml) and treated with (3R)-3-deoxo-11-deoxy-3-methoxy-11-oxo-4-epimutilin (167 mg) and tri-n-butyl phosphine (0.125 ml). After stirring overnight, the solution was added to a silica column and eluted EtOAc/hexane to give title compound (181 mg), identical to the product of Example 9, step(a).

Example 48

(2-Methylthio-4-oxo-3,4-dihydropyrimidine-5-carboxylic acid) (3R)-3-deoxo-11-deoxy-3-methoxy-11-oxo-4-epimutilin 14-ester A mixture of 2-methylthio-4-oxo-3,4-dihydropyrimidine-5-carboxylic acid (186 mg), (3R)-3-deoxo-11-deoxy-3-methoxy-11-oxo-4-epimutilin (84 mg), 4-dimethylaminopyridine (31 mg) and dicyclohexylcarbodiimide (206 mg) in dichloromethane (2 ml) was stirred overnight. After dilution with dichloromethane (20 ml) the solution was washed with 0.5N HCl, water and aqueous $NaHCO_3$ (20 ml of each), dried and evaporated. NMR analysis showed 40% conversion to the title compound. MS (−ve ion electrospray) m/z 501 ($[M-H]^-$, 100%).

Example 49

(1,6-Dihydro-1-methoxymethyl-6-oxopyrimidine-5-carboxylic acid) mutilin 14-ester and (1,4-dihydro-1-methoxymethyl-4-oxopyrimidine-5-carboxylic acid) mutilin 14-ester

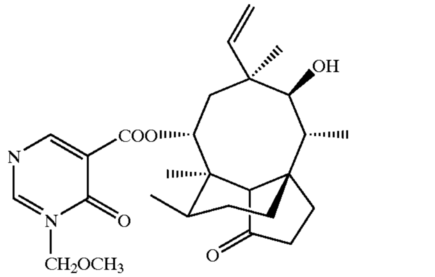

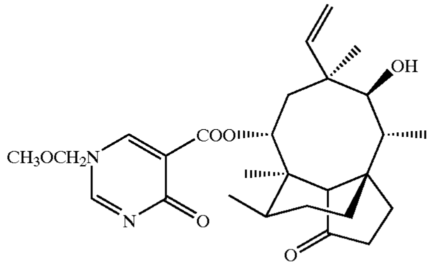

A solution of (1,6-dihydro-6-oxopyrimidine-5-carboxylic acid) mutilin 14-ester (150 mg) in DMF (4 ml) was treated with $K_2CO_3$ (50 mg) and chloromethyl methyl ether (0.027 ml), stirred overnight and diluted with EtOAc (20 ml). The solution was washed with water (3x20 ml), dried and evaporated. Chromatography (EtOAc/hexane) gave the title compounds, respectively 80 mg MS (+ve ion electrospray) m/z 995 ($2MNa^+$, 100%), 509 ($MNa^+$, 45%) and 60 mg MS (+ve ion electrospray) m/z 995 (2 $MNa^+$, 10%), 487 ($MH^+$, 10%), 185 (100%).

The following Examples (50–72) were prepared by alkylation of heterocycles as in Example 49. For Examples 59, 62, 64–66, 0.1 equivalent of tetrabutylammonium iodide was included in the reaction. Alkylating agents were MEM chloride, iodomethane, bromomethylpyridines, bromoacetylpyridine, 6-chloro-3-chloromethylpyridazine, 1,3-dibromopropane, 2-chloromethyl-4-dimethylaminopyrimidine (R. J. Ife and T. H. Brown, U.S. Pat. No. 4,777,172, 1988), bromoacetonitrile, 4-chloromethyl-6-dimethylamino-5-methylpyrimidine (Ife and Brown, U.S. Pat. No. 4,777,172), 1-benzyl-2-chloromethylimidazole (R. G. Jones, JACS (1949), 71, 383–6), 2-chloro-5-chloromethylpyridine (P. Bruneau, C. Delvare, M. P. Edwards and R. M. McMillan, J. Med. Chem. (1991), 34, 1028–36), 2-bromoethyl acetate and 3-bromopropanol.

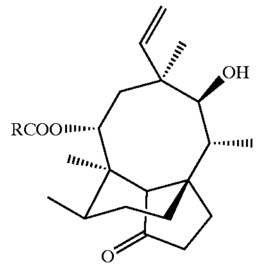

| Example No. | R | yield (%) | MS m/z |
|---|---|---|---|
| 50 | 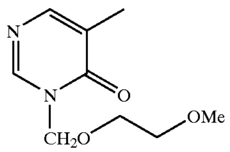 | 51 | (+ve ion electrospray) 553 ($MNa^+$, 90%), 251 (100%) |
| 51 | 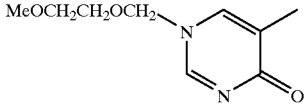 | 28 | (+ve ion electrospray) 553 ($MNa^+$, 100%), 531 ($MH^+$, 40%) |
| 52 | 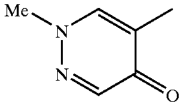 | 61 | (−ve ion electrospray) 515 ($MOAc^-$, 100%) |
| 53 | 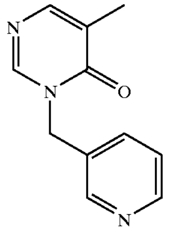 | 71 | (−ve ion electrospray) 592 ($MOAc^-$, 100%), 532 ($[M-H]^-$, 50%) |
| 54 | 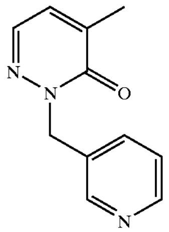 | 63 | (+ve ion electrospray) 534 ($MH^+$, 100%) |
| 55 | 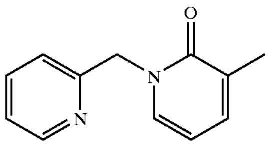 | 45 | (−ve ion electrospray) 591 ($MOAc^-$, 80%) |

-continued
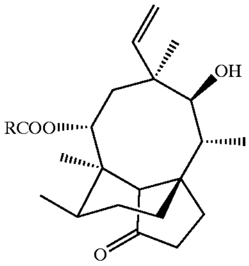
| Example No. | R | yield (%) | MS m/z |
|---|---|---|---|
| 56 | 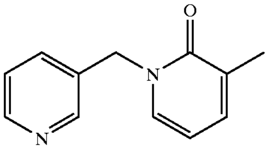 | 34 | (+ve ion chemical ionisation) 533 ($MH^+$, 100%). |
| 57 | 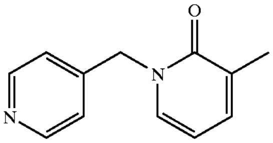 | 21 | (+ve ion chemical ionisation) 533 ($MH^+$, 100%) |
| 58 | 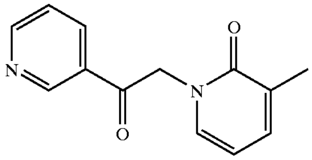 | 34 | (−ve ion electrospray) 559 ($[M - H]^-$ 100%) |
| 59 | 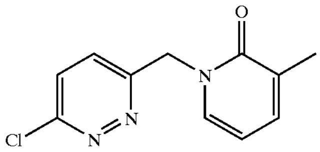 | 78 | |
| 60 | 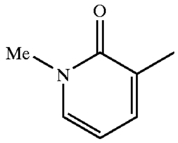 | 58 | |
| 61 | 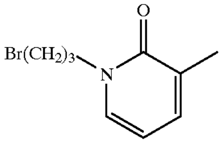 | 71 | (+ve ion chemical ionisation) 584 and 586 ($MNa^+$) |
| 62 | 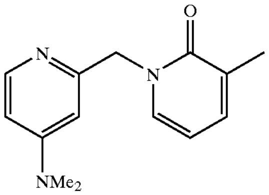 | 18 | (+ve ion electrospray) 577 ($MH^+$, 40%), 275 (100%) |

-continued
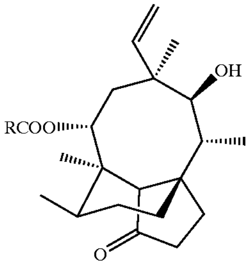
| Example No. | R | yield (%) | MS m/z |
|---|---|---|---|
| 63 | 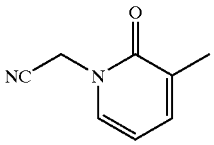 | 100 | (−ve ion elecrospray) 479 ([M − H]$^-$, 100%) |
| 64 | 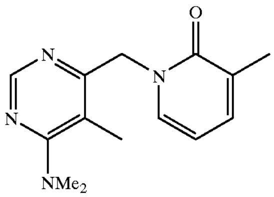 | 41 | (+ve ion electospray) 591 (MH$^+$, 40%), 289 (100%) |
| 65 | 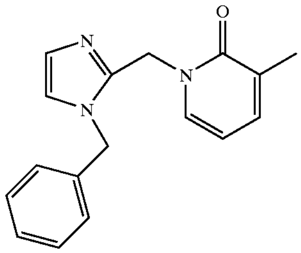 | 29 | (+ve ion electrospray) 612 (MH$^+$, 40%), 171 (100%) |
| 66 | 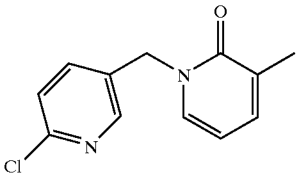 | 66 | (−ve ion electrospray) 625 (MOAc$^-$, 100%) |
| 67 | 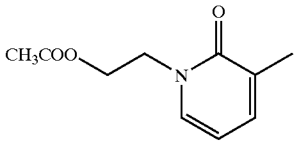 | 63 | (−ve ion electrospray) 586 (MOAc$^-$, 100%) |

-continued
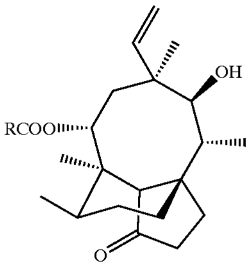
| Example No. | R | yield (%) | MS m/z |
|---|---|---|---|
| 68 | 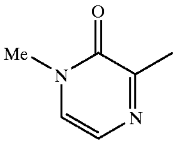 | 58 | (−ve ion electrospray) 515 (MOAc$^-$, 100%) |
| 69 | 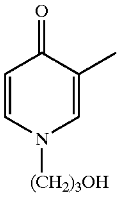 | 38 | (+ve ion electrospray) 500 (MH$^+$, 15%), 198 (100%) |
| 70 | 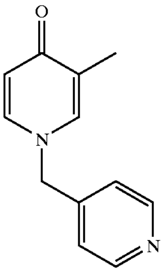 | 61 | (−ve ion electrospray) 531 ([M − H]$^-$, 100%) |
| 71 | 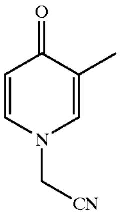 | 69 | (−ve ion electrospray) 479 ([M − H]$^-$, 100%) |
| 72 | 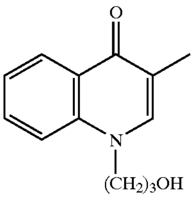 | 34 | (−ve ion electrospray) 608 (MOAc$^-$, 100%) |

Example 73

[2-Oxo-1-(tetrazolo[1,5-b]pyridazin-6-ylmethyl)-1,2-dihydropyridine-3-carboxylic acid] mutilin 14-ester

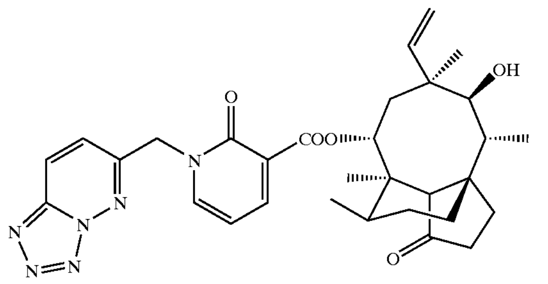

A solution of (1-(3-chloropyridazin-6-ylmethyl)-2-oxo-1,2-dihydropyridine-3-carboxylic acid] mutilin 14-ester (284 mg) in DMF (5 ml) with sodium azide (260 mg) was heated at 130° C. for 5 hours, cooled, diluted with EtOAc (30 ml), washed with water, dried and evaporated. Chromatography (EtOAc/MeOH) gave title compound (50 mg).

Example 74

[1-(3-Aminopyridazin-6-ylmethyl)-2-oxo-1,2-dihydropyridine-3-carboxylic acid] mutilin 14-ester

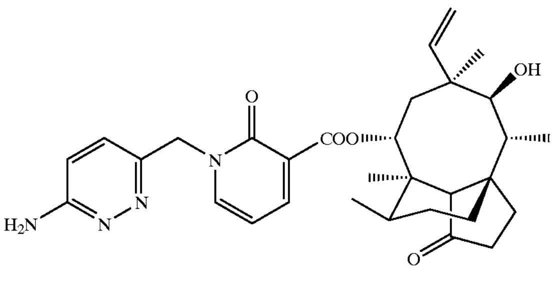

A solution of (2-oxo-1-tetrazolo[1,5-b]pyridazin-6-ylmethyl)-1,2-dihydropyridine-3-carboxylic acid] mutilin 14-ester (271 mg) and triphenylphosphine (123 mg) in chlorobenzene (2 ml) was refluxed 2 hours, cooled and evaporated. The residue was dissolved in HOAc/$H_2O$ (8:1, 10 ml), refluxed 25 mins and evaporated. Chromatography gave the title compound (50 mg). MS (−ve ion electrospray) m/z 607 ($MOAc^-$,100%).

Example 75

[1-(3-hydroxypropyl)-2-oxo-1,2-dihydropyridine-3-carboxylic acid] mutilin 14-ester and (1-(3-imidazolylpropyl)-2-oxo-1,2-dihydropyridine-3-carboxylic acid] mutilin 14-ester

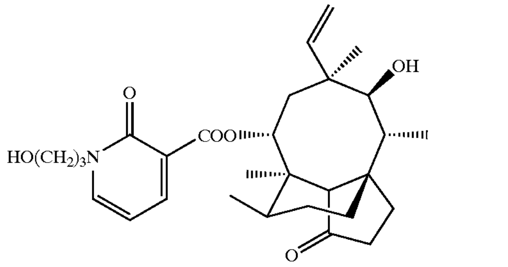

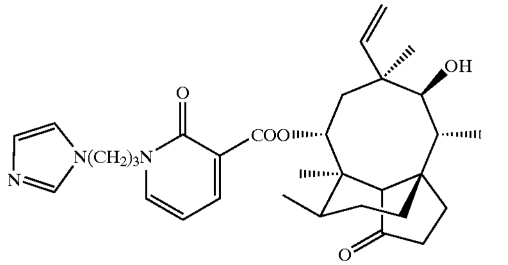

A solution of [1-(3-bromopropyl)-2-oxo-1,2-dihydropyridine-3-carboxylic acid] mutilin 14-ester (90 mg) in DMF (2 ml) was treated with $K_2CO_3$ (33 mg) and imidazole (25 mg) and stirred 16 hours. The mixture was diluted with EtOAc (20 ml), washed with water, dried and evaporated. Chromatography (EtOAc/MeOH) gave the title compounds, respectively 18 mg, MS (+ve ion chemical ionisation) m/z 522 ($MNa^+$, 100%) and 10 mg, MS (+ve ion chemical ionisation) m/z 572 ($MNa^+$, 100%).

The following were prepared similarly, using morpholine, 2-mercaptoimidazole and 4-(3-pyridyl)-1H-imidazole (A. Denis et al., Bioorg. and Med.Chem.Lett. (1999), 9, 3075–80).

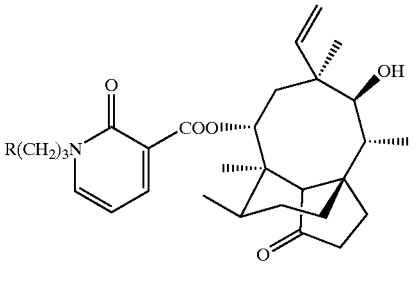

| Example No. | R | yield (%) | MS m/z |
|---|---|---|---|
| 76 | 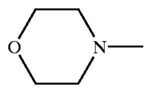 | 84 | (−ve ion electrospray) 627 ($MOAc^-$, 100%) |

-continued

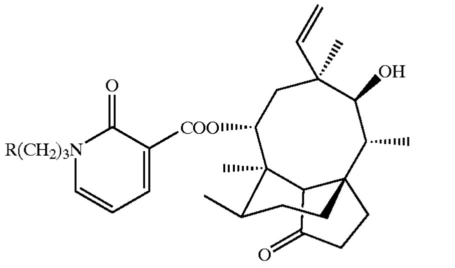

| Example No. | R | yield (%) | MS m/z |
|---|---|---|---|
| 77 | 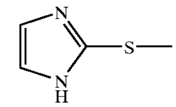 | 46 | (+ve ion electrospray) 604 ($MNa^+$, 100%) |
| 78 | 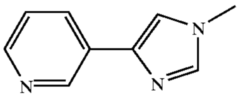 | 11 | (+ve ion electrospray) 627 ($MH^+$ 100%) |

Example 79

[1-(2-hydroxyethyl)-2-oxo-1,2-dihydropyridine-3-carboxylic acid] mutilin 14-ester

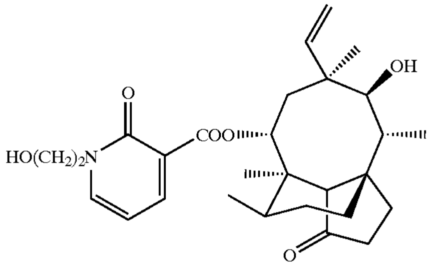

A solution of [1-(2-acetoxyethyl)-2-oxo-1,2-dihydropyridine-3-carboxylic acid] mutilin 14-ester (700 mg) in dioxan (5 ml)/$H_2O$ (5 ml) was treated with 1N NaOH (1.53 ml) and stirred 4 hours. Water (10 ml) was added and the mixture extracted with dichloromethane (3x10 ml). The organic was dried and evaporated to give title compound (550 mg). MS (−ve ion electrospray) m/z 544 ($MOAc^-$, 100%).

Example 80

{1-[3-(Imidazol-1-yl)propyl]-4-oxo-1,4-dihydropyridine-3-carboxylic acid} mutilin 14-ester

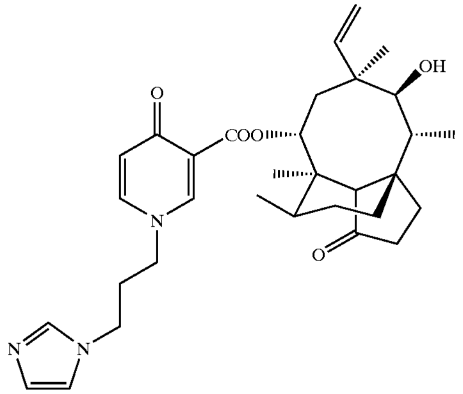

[1-(3-hydroxypropyl)-4-oxo-1,4-dihydropyridine-3-carboxylic acid] mutilin 14-ester (0.18 g) was treated with triethylamine (0.055 ml) and methanesulphonyl chloride (0.029 ml) in dichloromethane (50 ml) at ambient temperature for 18 hours. The solution was washed with saturated sodium hydrogen carbonate solution, separated, dried and evaporated. The residue was dissolved in dimethyl formamide (5 ml) and treated with imidazole (0.12 g) at 90° C. for 18 hours. The mixture was evaporated to dryness and chromatographed on silica gel, eluting with methanol/0.880 ammonia/dichloromethane 9:1:90. This gave the title compound (0.034 g, 20%). MS (+ve ion electrospray) m/z 550 ($MH^+$, 30%), 572 ($MNa^+$, 100%).

Example 81

{1-[3-(1,1-dioxothiomorpholin-4-yl)propyl]-4-oxo-1,4-dihydropyridine-3-carboxylic acid}mutilin 14-ester

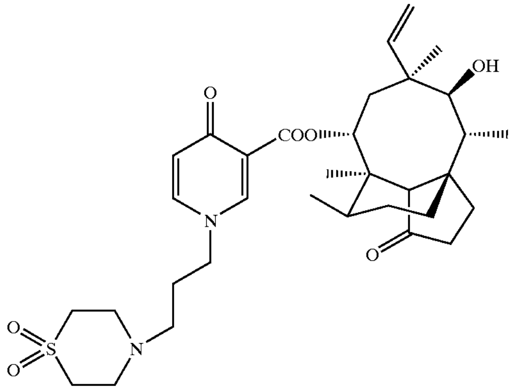

[1-(3-hydroxypropyl)-4-oxo-1,4-dihydropyridine-3-carboxylic acid] mutilin 14-ester (0.215 g) was converted to the mesylate as in Example 80. This was dissolved in toluene (10 ml) and treated with 1,1-dioxothiomorpholine trifluoro acetate salt (0.41 g) and N,N-diisopropylamine (0.57 ml) and heated under reflux for 18 hours. The mixture was evaporated to dryness and the residue partitioned between dichloromethane and saturated sodium hydrogen carbonate solution. The organics were dried and evaporated to dryness. Chromatography on silica gel, eluting with 4–12% methanol/dichloromethane gave the title compound (0.02 g, 10%). MS (+ve ion electrospray) m/z 639 ($MNa^+$, 45%), 315 (100%).

Example 82

[3,4-Dihydro-2-(4-methyl-1-piperazinyl)-4-oxopyrimidine-5-carboxylic acid] mutilin 14-ester

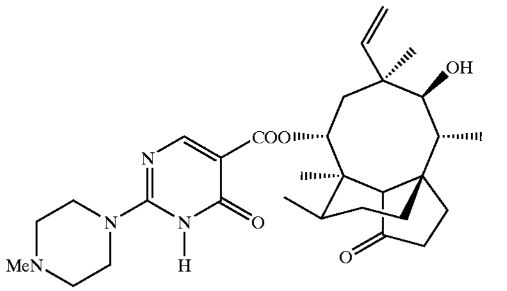

(a) [3,4-Dihydro-2-(4-methyl-1-piperazinyl)-4-oxopyrimidine-5-carboxylic acid] (3R)-3-deoxo-11-deoxy-3-methoxy-11-oxo-4-epimutilin 14-ester A solution of (3,4-dihydro-2-methylthio-4-oxopyrimidine-5-carboxylic acid) (3R)-3-deoxo-11-deoxy-3-methoxy-11-oxo-4-epimutilin 14-ester (Example 5) (0.25 g) in dioxan (3 ml) was treated with 1-methylpiperazine (0.09 ml) and refluxed under argon for 4 days. The solution was evaporated and the residue chromatographed ($CHCl_3$/MeOH/0.88$NH_3$(aq) 97.5:2.5:0.25) to give title compound as a foam (220 mg). MS(−ve ion electrospray) m/z 553 ($[M-H]^-$, 100%).

(b) [3,4-Dihydro-2-(4-methyl-1-piperazinyl)-4-oxopyrimidine-5-carboxylic acid] mutilin 14-ester Material from step (a) in dioxan (5 ml) was treated with conc. HCl (2.5 ml) and stirred overnight. $CHCl_3$ (20 ml) and water (20 ml) were added, followed by solid $NaHCO_3$ until basic. Layers were shaken and separated, the organic was dried and evaporated to leave title compound as a foam (210 mg) MS (−ve ion electrospray) m/z 539 ($[M-H]^-$, 100%)

Examples 83–97 were prepared analogously to Example 82

Step (a)

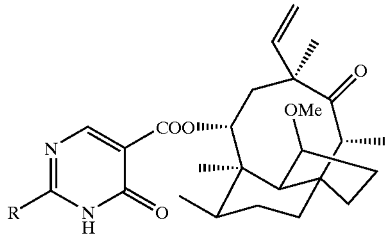

| Example No | R | yield (%) | MS (−ve ion electrospray) m/z |
|---|---|---|---|
| 83 | $BOCNHCH_2CH_2NH—$ | 78 | 613 ($[M - H]^-$, 100%) |
| 84 | 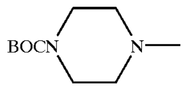 | 94 | 639 ($[M - H]^-$, 100%) |
| 85 | BOCNHNH— | 90 | 585 ($[M - H]^-$, 50%), 511 (100%) |
| 86 | 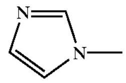 | 74 | 521 ($[M - H]^-$, 75%), 205 (100%) |
| 87 | $BOCNHCH_2CONHNH—$ | 68 | 642 ($[M - H]^-$, 100%) |
| 88 | 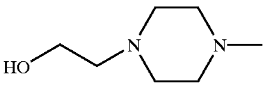 | 94 | 583 ($[M - H]^-$, 100%) |

-continued
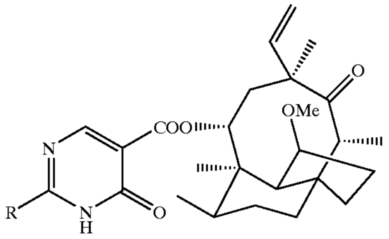
| Example No | R | yield (%) | MS (−ve ion electrospray) m/z |
|---|---|---|---|
| 89 | 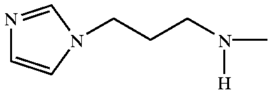 | 96 | 578 ([M − H]⁻, 100%) |
| 90 | 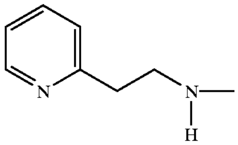 | 96 | 575 ([M − H]⁻, 100%) |
| 91 | 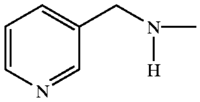 | 79 | 561 ([M − H]⁻, 100%) |
| 92 | 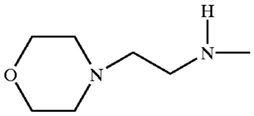 | 92 | 583 ([M − H]⁻, 100%) |
| 93 | 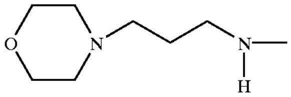 | 99 | 597 ([M − H]⁻, 100%) |
| 94 | 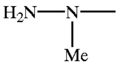 | 17 | 499 ([M − H]⁻, 100%) |
| 95 | 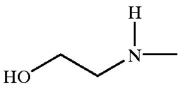 | 38 | 514 ([M − H]⁻, 100%) |
| 96 | 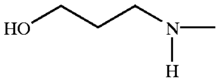 | 57 | 528 ([M − H]⁻, 100%) |
| 97 | 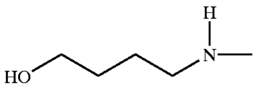 | 52 | 542 ([M − H]⁻, 100%) |

Step (b)
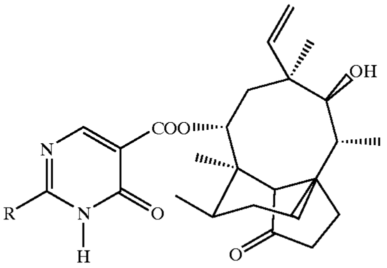
| Example No | R | yield (%) | MS (-ve ion electrospray) m/z |
|---|---|---|---|
| 83 | 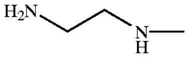 | 96 | 499 ($[M-H]^-$, 100%) |
| 84 | 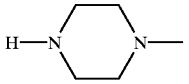 | 100 | 525 ($[M-H]^-$, 50%), 223 (100%) |
| 85 | $H_2NNH$— | 53 | 471 ($[M-H]^-$, 50%), 169 (100%) |
| 86 | 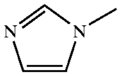 | 77 | 507 ($[M-H]^-$, 100%) |
| 87 | $H_2NCH_2CONHNH$— | 59 | 528 ($[M-H]^-$, 100%) |
| 88 | 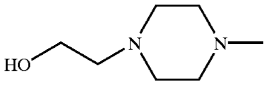 | 100 | 569 ($[M-H]^-$, 100%) |
| 89 | 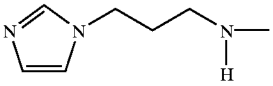 | 81 | 564 ($[M-H]^-$, 100%) |
| 90 | 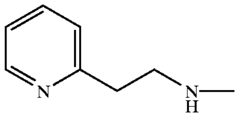 | 93 | 561 ($[M-H]^-$, 100%) |
| 91 | 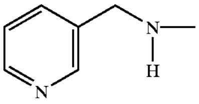 | 100 | 547 ($[M-H]^-$, 100%) |
| 92 | 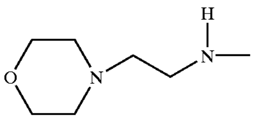 | 100 | 569 ($[M-H]^-$, 100%) |
| 93 | 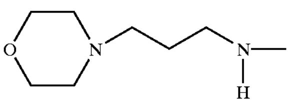 | 100 | 583 ($[M-H]^-$, 100%) |
| 94 | 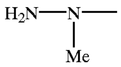 | 60 | 485 ($[M-H]^-$, 100%) |
| 95 | 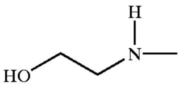 | 100 | 500 ($[M-H]^-$, 100%) |

-continued

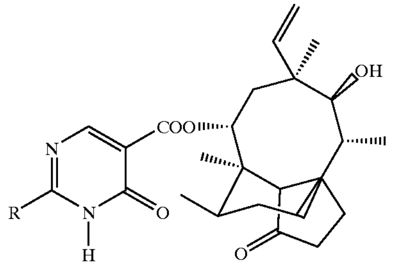

| Example No | R | yield (%) | MS (−ve ion electrospray) m/z |
|---|---|---|---|
| 96 | 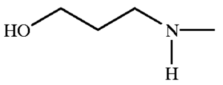 | 100 | 514 ([M − H]⁻, 100%) |
| 97 | 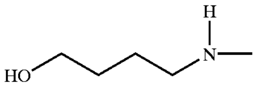 | 100 | 528 ([M − H]⁻, 100%) |

Example 98

{3,4-Dihydro-2-[2-(glycylaminoethyl)amino]-4-oxopyrimidine-5-carboxylic acid}mutilin 14-ester

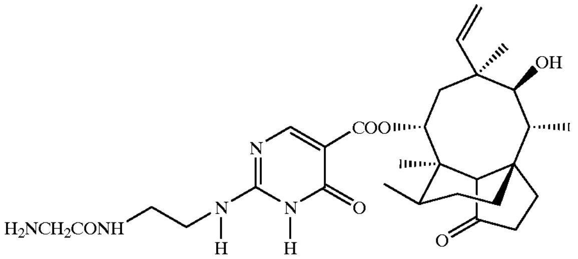

(a) {3,4-Dihydro-2-[2-(BOC glycylaminoethyl)amino]-4-oxopyrimidine-5-carboxylic acid}mutilin 14-ester A solution of {3,4-dihydro-2-[2-aminoethylamino]-4-oxopyrimidine-5-carboxylic acid}mutilin 14-ester (150 mg) in dichloromethane (3 ml)/DMF (1 ml) was ice-cooled, treated with BOC glycine (53 mg), pyridine (0.024 ml) and dicyclohexylcarbodiimide (74 mg) and stirred overnight. EtOAc (20 ml) was added, the solution washed with water (3×20 ml), dried and evaporated. Chromatography ($CHCl_3$/MeOH/0.88$NH_3$ aq) gave the title compound (193 mg). MS (+ve ion electrospray), m/z 658 ($MH^+$, 100%).

(b) {3,4-Dihydro-2-[2-(glycylaminoethyl)amino]-4-oxopyrimidine-5-carboxylic acid}mutilin 14-ester The material from step (a) was dissolved in TFA (10 ml), kept 2 hours and evaporated. The residue was dissolved in excess aqueous $NaHCO_3$ and extracted several times with 10% EtOH/$CHCl_3$. The organic was dried and evaporated to give the title compound as a white solid (150 mg). MS (−ve ion electrospray), m/z 556 ($[M-H]^-$, 100%).

Example 99

[3,4-Dihydro-2-(4-glycyl-1-piperazinyl)-4-oxopyrimidine-5-carboxylic acid]mutilin 14-ester Preparation according to the procedure of Example 98. MS (−ve ion electrospray), m/z 582 ($[M-H]^-$, 75%), 280 (100%).

Example 100

{3,4-Dihydro-2-[2-(carboxamidomethylaminoethyl)amino]-4-oxopyrimidine-5-carboxylic acid}mutilin 14-ester

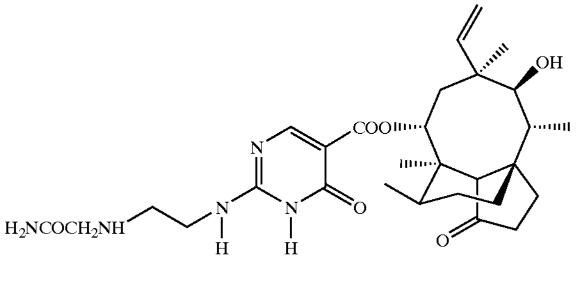

A solution of {3,4-dihydro-2-[2-aminoethylamino]-4-oxopyrimidine-5-carboxylic acid}mutilin 14-ester (150 mg) in DMF (4 ml) was treated with $K_2CO_3$ (83 mg) and 2-bromoacetamide (41 mg), stirred overnight and evaporated to dryness. The residue was taken up in chloroform, applied to a silica column and eluted $CHCl_3$/MeOH/0.88$NH_3$ (aq) to give title compound (65 mg). MS (−ve ion electrospray), m/z 556 ($[M-H]^-$, 100%).

Example 101

[3,4-Dihydro-2-(4-carboxamidomethyl-1-piperazinyl)-4-oxopyrimidine-5-carboxylic acid] mutilin 14-ester

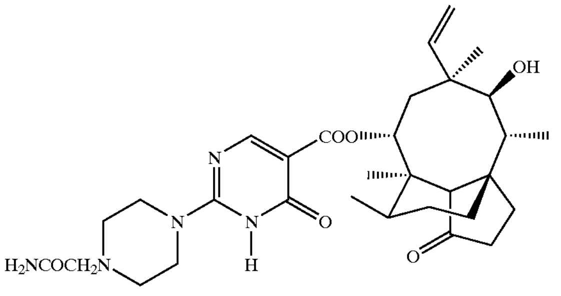

Preparation according to the procedure of Example 100. MS (−ve ion electrospray) m/z 582 ([M−H]$^-$, 95%), 280 (100%).

Example 102

(4-Oxo-6,7,8,9-tetrahydro-4H-pyrimido[1,2-a] pyrimidine-3-carboxylic acid)mutilin 14-ester and (2-oxo-6,7,8,9-tetrahydro-2H-pyrimido[1,2-a] pyrimidine-3-carboxylic acid)mutilin 14-ester

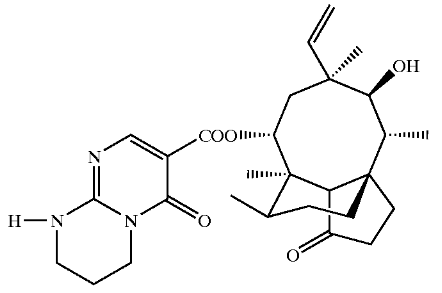

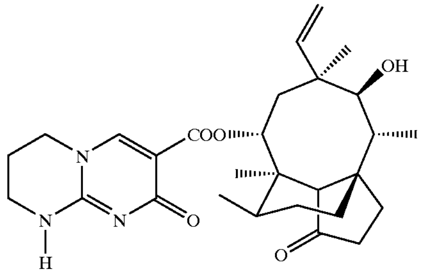

A solution of [3,4-dihydro-2-(3-hydroxypropylamino)-4-oxopyrimidine-5-carboxylic acid] (3R)-3-deoxo-11-deoxy-3-methoxy-11-oxo-4-epimutilin 14-ester (103 mg) in dichloromethane (3 ml) was treated with triethylamine (0.041 ml) and methanesulfonyl chloride (0.023 ml) and left 24 hours. The solution was added to a silica column and eluted with $CHCl_3/MeOH/0.88NH_3$ (aq) mixtures to separate 2 compounds. These were both treated with acid as in Example 82 step (b) to provide the title compounds.

(4-Oxo-6,7,8,9-tetrahydro-4H-pyrimido[1,2-a] pyrimidine-3-carboxylic acid) mutilin 14-ester (less polar, 19 mg). MS (−ve ion electrospray), m/z 496 ([M−H]$^-$, 100%). UV (EtOH) $\lambda_{max}$ 309 nm ($\epsilon$ 11930).

(2-Oxo-6,7,8,9-tetrahydro-2H-pyrimido[1,2-a] pyrimidine-3-carboxylic acid) mutilin 14-ester (more polar, 15 mg). MS (−ve ion electrospray), m/z 496 ([M−H]$^-$, 100%). UV (EtOH) $\lambda_{max}$ 284 nm ($\epsilon$ 7350).

Example 103

[1-Ethyl-6-fluoro-4-oxo-7-(4-methylsulfonylpiperazin-1-yl)-1,4-dihydroquinoline-3-carboxylic acid]mutilin 14-ester

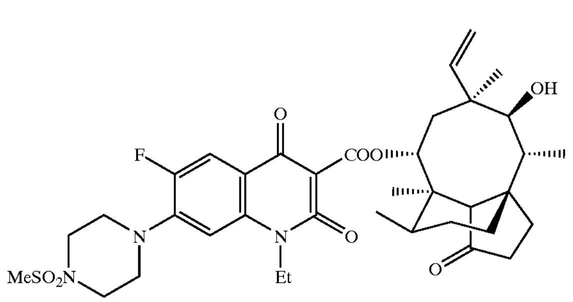

[1-Ethyl-6-fluoro-4-oxo-7-(piperazin-1-yl)-1,4-dihydro quinoline carboxylic acid]mutilin 14-ester (Example 34) (0.1 g) in dichloromethane (10 ml) was treated with triethylamine (0.025 ml) and methanesulfonyl chloride (0.014 ml) and stirred at ambient temperature for 18 hours. The solution was washed with water, dried ($Na_2SO_4$) and evaporated to dryness to give the title compound (0.078 g, 70%). MS (−ve ion electrospray), m/z 758 (MOAc$^-$, 100%).

Example 104

[1-Ethyl-6-fluoro-4-oxo-7-(4-carbamoylpiperazin-1-yl)-1,4-dihydroquinoline-3-carboxylic acid]mutilin 14-ester

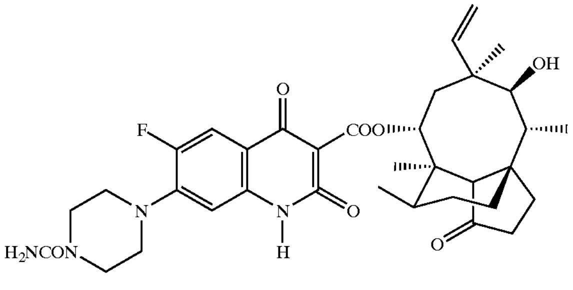

[1-Ethyl-6-fluoro-4-oxo-7-(piperazin-1-yl)-1,4-dihydroquinoline-3-carboxylic acid]mutilin 14-ester (0.1 g) in dichloromethane (10 ml) was treated with trimethylsilyl isocyanate (0.024 g) and stirred at ambient temperature for 18 hours. The mixture was washed with water, separated, dried and evaporated to give title compound (0.088 g, 82%). MS (−ve ion electrospray) m/z 723 (MOAc$^-$, 100%).

Example 105

(2-Aminonicotinic acid) mutilin 14-ester (a) (2-Aminonicotinic acid) (3R)-3-deoxo-11-deoxy-3-methoxy-11-oxo-4-epimutilin 14-ester The product of Example 20 (200 mg) and 32% aqueous ammonia (10 ml) were heated overnight in a bomb at 150° C., cooled and evaporated to give the title compound as a brown solid (180 mg). MS (+ve ion chemical ionisation) m/z 455 (MH$^+$, 30%), 285 (100%).

(b) (2-Aminonicotinic acid) mutilin 14-ester

Material from step (a) was rearranged by the procedure of Example 14 step (b) to give title compound (52%). MS (+ve ion chemical ionisation) m/z 441 ($MH^+$, 100%).

Example 106

(2-Methylthionicotinic acid) mutilin 14-ester (a) (2-Methylthionicotinic acid) (3R)-3-deoxo-11-deoxy-3-methoxy-11-oxo-4-epimutilin 14-ester The product of example 20, (200 mg) in THF (20 ml) was treated with sodium thiomethoxide (60 mg) and refluxed overnight. Solvent was evaporated and the residue partitioned between saturated aqueous $NaHCO_3$ (20 ml) and dichloromethane (20 ml). The organic was dried and evaporated to give the title compound (100 mg). MS (+ve ion chemical ionisation) m/z 486 ($MH^+$, 100%).

(b) (2-Methylthionicotinic acid) mutilin 14-ester

Material from step (a) was rearranged by the procedure of Example 14 step (b) to give title compound (50%). MS (+ve ion chemical ionisation) m/z 472 ($MH^+$, 100%).

Example 107

[7-(Piperazin-1-yl)-4-oxo-1,4-dihydropyrimido[4,5-c]pyridazine-3-carboxylic acid]19,20-dihydromutilin 14-ester

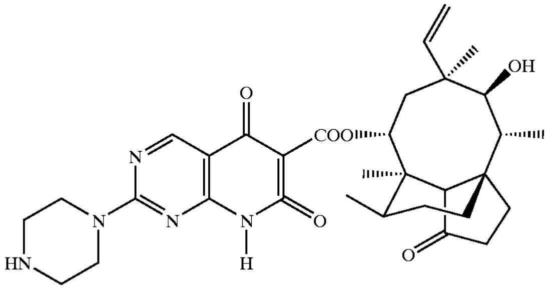

(a) (7-Methylsulfonyl-4-oxo-1,4-dihydropyrimido[4,5-c]pyridazine-3-carboxylic acid)19,20-dihydromutilin 14-ester (7-Methylthio-4-oxo-1,4-dihydropyrimido[4,5-c]pyridazine-3-carboxylic acid)19,20-dihydromutilin 14-ester (Example 8) (0.14 g) in chloroform (10 ml) was treated with 3-chloroperoxybenzoic acid (0.127 g) and stirred at ambient temperature for 18 hours. The mixture was washed with saturated sodium bicarbonate, dried and evaporated to dryness to give the title compound (0.14 g). MS (−ve ion electrospray) m/z 573 ($[M-H]^-$, 100%).

(b) [7-(4-t-Butoxycarbonylpiperazin-1-yl)-4-oxo-1,4-dihydropyrimido[4,5-c]pyridazine-3-carboxylic acid)19,20-dihydromutilin 14-ester (7-Methylsulfonyl-4-oxo-1,4-dihydropyrimido[4,5-c]pyridazine-3-carboxylic acid)19,20-dihydromutilin 14-ester (0.14 g) in ethanol (10 ml) was treated with 1-tert-butyloxycarbonylpiperazine (0.097 g) and heated under reflux for 1 hour, allowed to cool then evaporated to dryness. The residue was partitioned between saturated sodium hydrogen carbonate and dichloromethane. The organics were separated and dried ($Na_2SO_4$) then evaporated to dryness. Chromatography, eluting with 2:1 ethyl acetate/hexane gave the title compound (0.108 g, 64%). MS (−ve ion electrospray) m/z 679 ($[M-H]^-$, 100%).

(c) [7-(Piperazin-1-yl)-4-oxo-1,4-dihydropyrimido[4,5-c]pyridazine-3-carboxylic acid)19,20-dihydromutilin 14-ester Material from step (b) was deprotected by the procedure of Example 98 step (b) to give title compound (82%). MS (+ve ion electrospray) m/z 581 ($MH^+$, 100%).

Example 108

(1-Amino-2-hydroxynicotinic acid) mutilin 14-ester

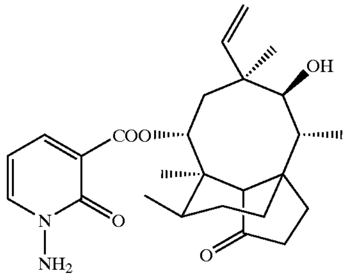

A solution of (2-hydroxynicotinic acid) mutilin 14-ester (70 mg) in DMF (10 ml) was treated with potassium carbonate (44 mg) and stirred for 3 hours. O-(2,4-dinitrophenyl)hydroxylamine (31.6 mg) was added and stirring continued for 3 days. The solvent was evaporated to dryness and the residue chromatographed, eluting with EtOAc/hexane, to provide the title compound (40 mg). MS (−ve ion electrospray) m/z 515 ($MOAc^-$, 60%), 455 ($[M-H]^-$, 80%), 153 (100%).

Examples 109–116 were prepared analogously to Example 108

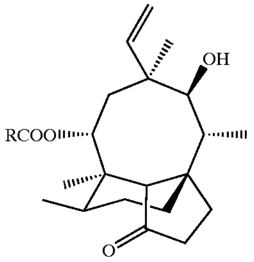

| Example No | R | yield (%) | MS (−ve ion electrospray) m/z |
|---|---|---|---|
| 109 | 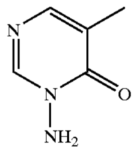 | 83 | 456 ($[M-H]^-$, 100%) |
| 110 | 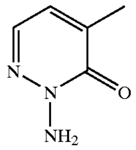 | 71 | 456 ($[M-H]^-$ (100%) |
| 111 | 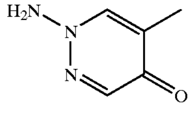 | 64 | 456 ($[M-H]^-$ (100%) |

-continued

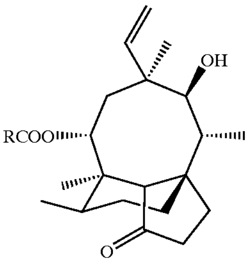

| Example No | R | yield (%) | MS (−ve ion electrospray) m/z |
|---|---|---|---|
| 112 | 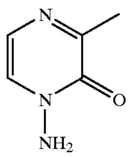 | | 456 ([M−H]$^-$ (100%) |
| 113 | 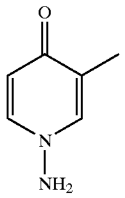 | 44 | 455 ([M−H]$^-$ (100%) |
| 114 | 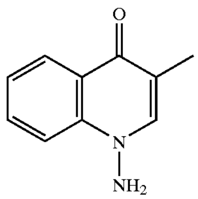 | 77 | 505 ([M−H]$^-$, 100%) |
| 115 | 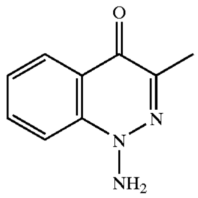 | 88 | 506 ([M−H]$^-$, 100%) |
| 116 | 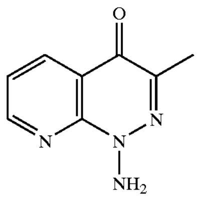 | 89 | 507 ([M−H]$^-$, 40%), 109(100%) |

Example 117

[1-Amino-4-oxo-7-(piperazin-1-yl)-1,4-dihydropyrimido[4,5-c]pyridazine-3-carboxylic acid]19,20-dihydromutilin 14-ester

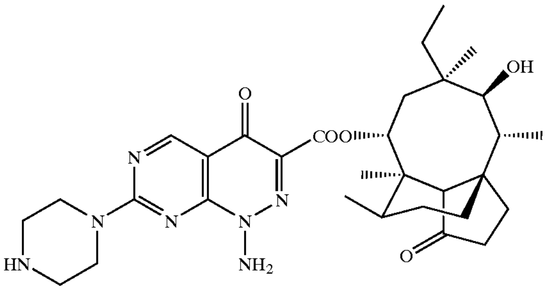

(a) [1-Amino-4-oxo-7-(4-t-butoxycarbonylpiperazin-1-yl)-1,4-dihydropyrimido[4,5-c]pyridazine-3-carboxylic acid]19,20-dihydromutilin 14-ester—Amination of [7-(4-t-butoxycarbonylpiperazin-1-yl)-4-oxo-1,4-dihydropyrimido[4,5-c]pyridazine-3-carboxylic acid]19,20-dihydromutilin 14-ester (Example 107 step (b)) by the procedure of Example 108 gave title compound (100%). MS (−ve ion electrospray) m/z 694 ([M−H]$^-$, 75%), 109 (100%).

(b) [1-Amino-4-oxo-7-(piperazin-1-yl)-1,4-dihydropyrimido[4,5-c]pyridazine-3-carboxylic acid]19,20-dihydromutilin 14-ester—Material from step (a) was deprotected by the procedure of Example 98 step (b) to give title compound (38%). MS (+ve ion electrospray) m/z 596 (MH$^+$, 65%), 292 (100%).

Example 118

(1,6-Dihydro-1-methylamino-6-oxopyridazine-5-carboxylic acid)mutilin 14-ester

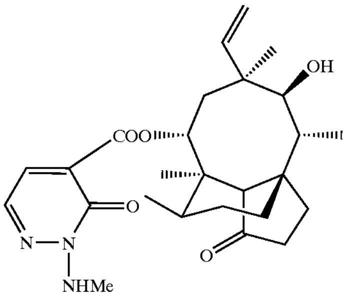

A solution of (3-pyridazinol-4-carboxylic acid)mutilin 14-ester (Example 14) (182 mg) in DMF (3 ml) was treated with $K_2CO_3$ (110 mg) and O-(2,4-dinitrophenyl)-N-methylhydroxylamine (T. Sheradsky, G. Salemnick and Z. Nir, Tet (1972), 28, 3833–43) (150 mg) and stirred 2 days. The solution was evaporated to dryness, the residue taken up in EtOAc, washed 3 times with water, dried and evaporated. Chromatography (EtOAc/hexane 1:1) gave the title compound (110 mg). MS (−ve ion electrospray) m/z 470 ([M−H]$^-$, 35%), 427 (100%).

Example 119

(1,4-Dihydro-1-methylamino-6-oxopyridazine-5-carboxylic acid)mutilin 14-ester

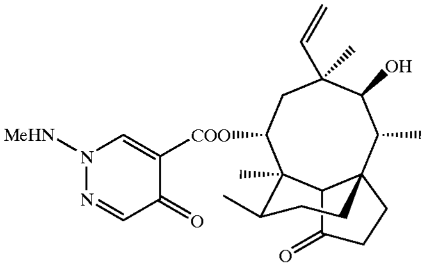

The title compound was prepared by the procedure of Example 118 (30%). MS (−ve ion electrospray) m/z 470 ([M−H]$^-$, 20%), 427 (100%).

Example 120

[1,6-Dihydro-1-(N-methyl-N-(D)-prolylamino)-6-oxopyridazine-5-carboxylic acid]mutilin 14-ester

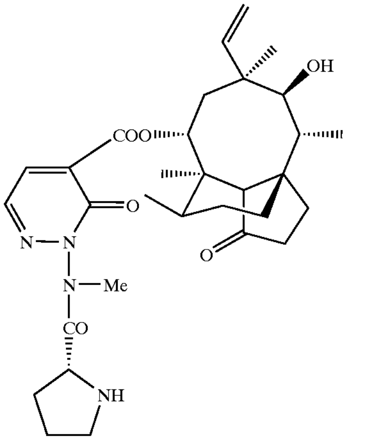

(a) [1,6-Dihydro-1-(N-BOC-(D)-prolylamino)-6-oxopyridazine-5-carboxylic acid] (3R)-3-deoxo-11-deoxy-3-methoxy-11-oxo-4-epimutilin 14-ester—A solution of (1,6-dihydro-1-amino-6-oxopyridazine-5-carboxylic acid) (3R)-3-deoxo-11-deoxy-3-methoxy-11-oxo-4-epimutilin 14-ester (70 mg, prepared from [1,6-dihydro-6-oxopyridazine-5-carboxylic acid](3R)-3-deoxo-11-deoxy-3-methoxy-11-oxo-4-epimutilin 14-ester by the procedure of Example 108) in dichloromethane (1 ml)/DMF (1 ml) was ice-cooled, treated with BOC-(D))-proline (96 mg), pyridine (0.036 ml) and dicyclohexylcarbodiimide (140 mg) and stirred overnight. The mixture was diluted with EtOAc (15 ml), washed with 0.5N HCl, water and aqueous $NaHCO_3$ (15 ml each), dried and evaporated. Chromatography gave the title compound (48 mg). MS (−ve ion electrospray) m/z 667 ([M−H]$^-$, 100%).

(b) [1,6-Dihydro-1-(N-methyl-N-BOC-(D)-prolylamino)-6-oxopyridazine-5-carboxylic acid] (3R)-3-deoxo-11-deoxy-3-methoxy-11-oxo-4-epimutilin 14-ester—Material produced as in step (a) (94 mg) in DMF (2 ml) was treated with $K_2CO_3$ (21 mg) and MeI (0.0093 ml) and stirred overnight. The mixture was diluted with EtOAc (15 ml), washed with water (3x15 ml), dried and evaporated. Chromatography (EtOAc/hexane) gave title compound (86 mg). MS (+ve ion electrospray) m/z 705 (MNa$^+$, 100%), 683 (MH$^+$, 15%).

(c) [1,6-Dihydro-1-(N-methyl-N-(D)-prolylamino)-6-oxopyridazine-5-carboxylic acid]mutilin 14-ester—Material from step (b) was subjected to the procedure of Example 14 step (b) to give title compound (70 mg). MS (+ve ion electrospray) m/z 569 (MH$^+$, 100%).

Example 121

[1,6-Dihydro-1-(N-methyl-N-(L)-trans-4-hydroxyprolylamino)-6-oxopyridazine-5-carboxylic acid]mutilin 14-ester

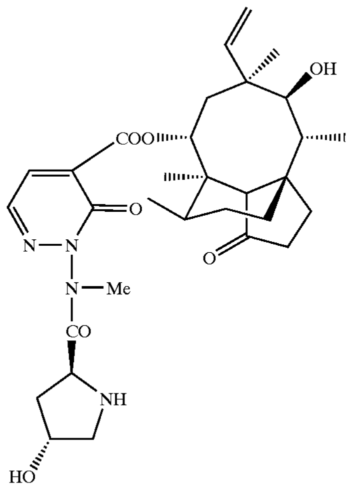

(a) [1,6-Dihydro-1-(N-BOC-(L)-trans-4-hydroxyprolylamino)-6-oxopyridazine-5-carboxylic acid] mutilin 14-ester.—A solution of (1,6-dihydro-1-amino-6-oxopyridazine-5-carboxylic acid)mutilin 14-ester (200 mg) in dichloromethane (3 ml)/DMF (3 ml) was ice-cooled, treated with BOC-(L)-trans-4-hydroxyproline dicyclohexylamine salt (290 mg), pyridine (0.106 ml) and dicyclohexylcarbodiimide (412 mg) and stirred 2 days. The mixture was diluted with EtOAc (20 ml), washed 0.5N HCl, water and aqueous $NaHCO_3$ (20 ml each), dried and evaporated. Chromatography (EtOAc) gave the title ompound (200 mg). MS (−ve ion electrospray) m/z 669 ([M−H]$^-$, 100%).

(b) [1,6-Dihydro-1-(N-methyl-N-BOC-(L)-trans-4-hydroxyprolylamino)-6-oxopyridazine-5-carboxylic acid] mutilin 14-ester.—Material from step (a) was converted into title compound by the procedure of Example 120 step (b) (110 mg). MS (+ve ion electrospray) m/z 707 (MNa$^+$, 50%), 685 (MH$^+$, 15%), 283 (100%).

(c) [1,6-Dihydro-1-(N-methyl-N-(L)-trans-4-hydroxy-6-oxopyridazine-5-carboxylic acid]mutilin 14-ester.—Material from step b) was dissolved in TFA, left 1.5 hours and evaporated. The residue was taken up in chloroform (10 ml), washed with aqueous $NaHCO_3$ (10 ml), dried and evaporated to give title compound (76 mg). MS (+ve ion electrospray) m/z 585 ($MH^+$, 100%).

Example 122

[1-(N-methyl-N-(D)-prolylamino)-2-oxo-1,2-dihydropyridine-3-carboxylic acid]mutilin 14-ester

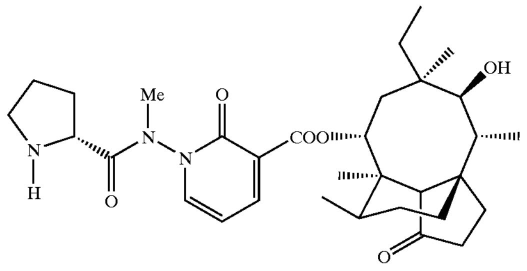

(a) [1-(N-BOC-(D)-prolylamino)-2-oxo-1,2-dihydropyridine-3-carboxylic acid]mutilin 14-ester—A solution of (1-amino-2-oxo-1,2-dihydropyridine-3-carboxylic acid)mutilin 14-ester (1.83 g) in DMF (30 ml) was treated with BOC-(D)-proline (1.72 g), 1-hydroxy-7-azabenzotriazole (165 mg) and 1-(3-dimethylaminopropyl)-3-ethylcarbodiimide hydrochloride (1.54 g) and stirred 16 hours. Work up as in Example 120 step (a) gave title compound (2.3 g). MS (−ve ion chemical ionisation) m/z 652 ($[M-H]^-$, 100%).

(b) [1-(N-methyl-N-BOC-(D)-prolylamino)-2-oxo-1,2-dihydropyridine-3-carboxylic acid]mutilin 14-ester—Material from step (a) was methylated by the procedure of Example 120 step (b) to give title compound (59%). MS (+ve ion chemical ionisation) m/z 690 ($MNa^+$, 100%).

(c) [1-(N-methyl-N-(D)-prolylamino)-2-oxo-1,2-dihydropyridine-3-carboxylic acid]mutilin 14-ester—Material from step (b) was deprotected by the procedure of Example 121 step (c) to give title compound (59%). MS (+ve ion chemical ionisation) m/z 590 ($MNa^+$, 100%).

Example 123

[1,6-Dihydro-1-(N-methyl-N-sarcosylamino)-6-oxopyridazine-5-carboxylic acid]mutilin 14-ester

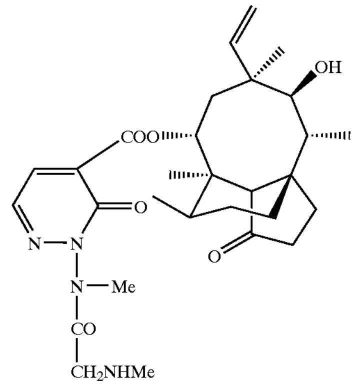

(a) [1,6-Dihydro-1-bis-(BOC-sarcosyl)amino-6-oxopyridazine-5-carboxylic acid]mutilin 14-ester—BOC sarcosine was reacted by the procedure of Example 120 to give title compound (76%). MS (+ve ion electrospray) m/z 822 ($MNa^+$, 90%), 817 ($MNH_4^+$, 80%), 342 (100%).

(b) [1,6-Dihydro-1-(BOC-sarcosylamino)-6-oxopyridazine-5-carboxylic acid]mutilin 14-ester—Material from step (a) (200 mg) in dioxan (5 ml)/water (2 ml) was treated with 2N NaOH (0.325 ml), stirred 2 hours and treated with water (10 ml) and 2N HCl (0.35 ml). After extraction with EtOAc (20 ml), the organic was dried and evaporated. Chromatography gave title compound (78 mg). MS (−ve ion electrospray), m/z 627 ($[M-H]^-$, 100%).

(c) [1,6-Dihydro-1-(N-methyl-N-BOC-sarcosylamino)-6-oxopyridazine-5-carboxylic acid]mutilin 14-ester—Material from step (b) was methylated by the procedure of Example 120 step (b) to give title compound (95%). MS (−ve ion electrospray) m/z 701 ($MOAc^-$, 100%), 641 ($[M-H]^-$, 20%).

(d) [1,6-Dihydro-1-(N-methyl-N-sarcosylamino)-6-oxopyridazine-5-carboxylic acid]mutilin 14-ester—Material from step (c) was deprotected by the procedure of Example 121 step (c) to give title compound (100%). MS (+ve ion electrospray) m/z 543 ($MH^+$, 100%).

Examples 124–139 were prepared using the procedures from Examples 120–122.

Thiomorpholine-4-acetic acid S,S-dioxide (Example 130) was obtained from Maybridge Chemical Co., Tintagel; morpholine-4-acetic acid (Example 131) from J. Rautio et. al., *J. Med. Chem.* (2000), 43, (8), 1489–94 and thietane-3-carboxylic acid (Example 126) from Allenmark, *Acta. Chem. Scand.* (1964), 18, 2197–8.

Step (a)
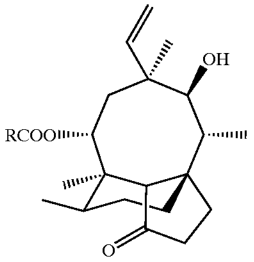
| Example No | R | yield (%) | MS m/z |
|---|---|---|---|
| 124 | 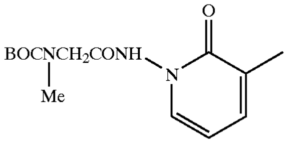 | 41 | (−ve ion chemical ionisation) 626 ([M−H]⁻, 100%) |
| 125 | 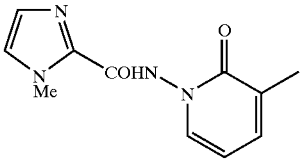 | 25 | (−ve ion electrospray) 563 ([M−H]⁻, 100%) |
| 126 | 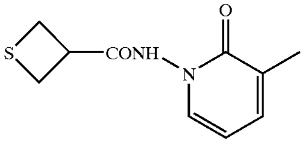 | 26 | (−ve ion electrospray) 555 ([M−H]⁻, 100%) |
| 127 | 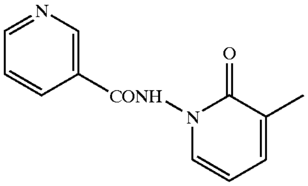 | 41 | (−ve ion electrospray) 560 ([M−H]⁻, 100%) |
| 128 | 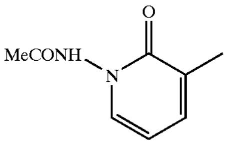 | 46 | (−ve ion electrospray) 497 ([M−H]⁻, 100%) |
| 129 | 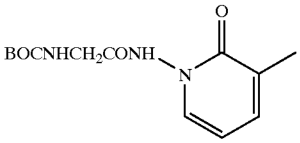 | 71 | (−ve ion electrospray) 612 ([M−H]⁻, 100%) |
| 130 | 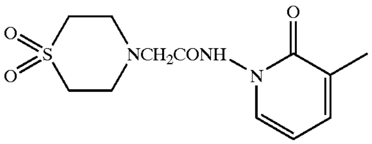 | 72 | (−ve ion electrospray) 630 ([M−H]⁻, 100%) |

-continued
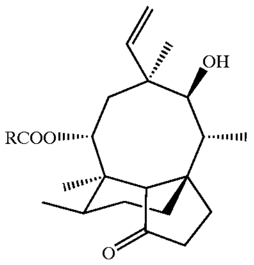
| Example No | R | yield (%) | MS m/z |
|---|---|---|---|
| 131 | 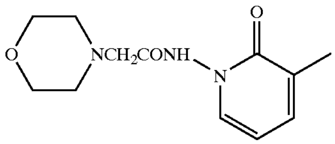 | 70 | (−ve ion electrospray) 582 ([M−H]⁻, 100%) |
| 132 | 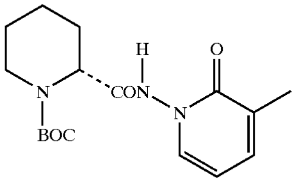 | 69 | (−ve ion electrospray) 666 ([M−H]⁻, 100%) |
| 133 | 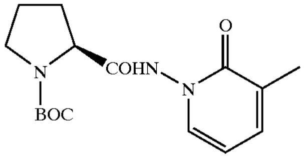 | 79 | |
| 134 | 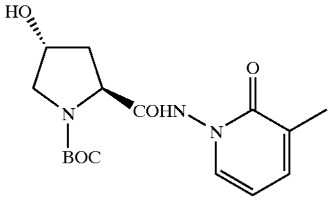 | 54 | (−ve ion electrospray) 668 ([M−H]⁻, 100%) |
| 135 | 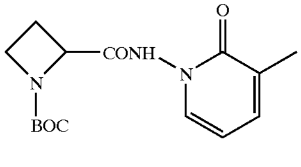 | 65 | (−ve ion electrospray) 638 ([M−H]⁻, 100%) |

-continued
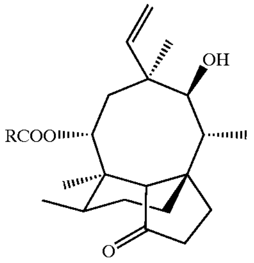
| Example No | R | yield (%) | MS m/z |
|---|---|---|---|
| 136 | 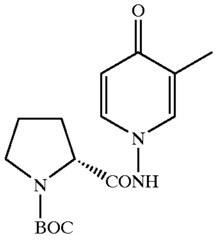 | 27 | (−ve ion electrospray) 652 ([M−H]$^-$, 12), 153 (100%) |
| 137 | 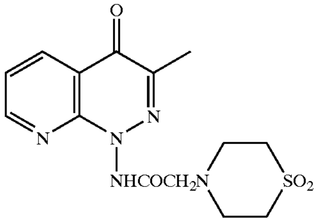 | 41 | (−ve ion electrospray) 682 ([M−H]$^-$, 100%) |
| 138 | 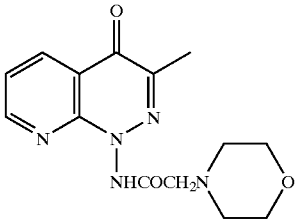 | 53 | (−ve ion electrospray) 634 ([M−H]$^-$, 100%) |
| 139 | 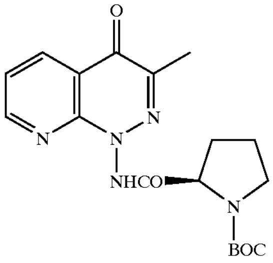 | 75 | (−ve ion electrospray) 704 ([M−H]$^-$, 100%) |

Step (b)
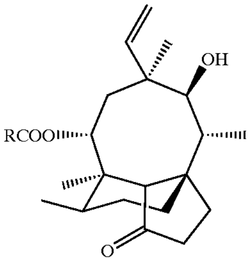
| Example No | R | yield (%) | MS m/z |
|---|---|---|---|
| 124 | 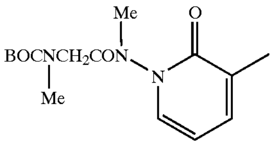 | 85 | (−ve ion ionisation) 700 ($MOAc^-$, 100%) |
| 125 | 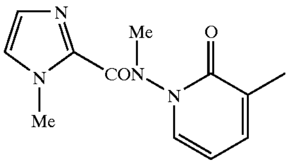 | 50 | (+ve ion chemical ionisation) 601 ($Mna^+$, 100%) |
| 126 | 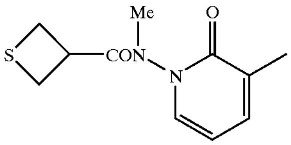 | 100 | (−ve ion electrospray) 629 ($MOAc^-$, 100%) |
| 127 | 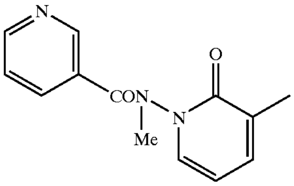 | 25 | (−ve ion electrospray) 638 ($MOAc^-$, 100%) |
| 128 | 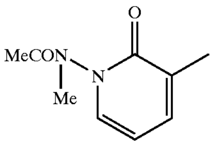 | 30 | (−ve ion electrospray) 571 ($MOAc^-$, 100%) |
| 129 | 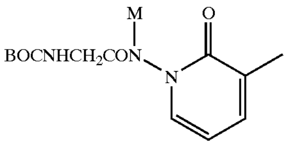 | 23 | (−ve ion electrospray) 626 ($[M-H]^-$, 100%) |
| 130 | 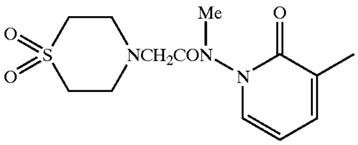 | 54 | (−ve ion electrospray) 704 ($MOAc^-$, 100%) |

-continued
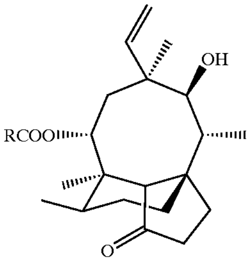
| Example No | R | yield (%) | MS m/z |
|---|---|---|---|
| 131 | 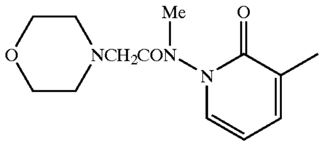 | 57 | (−ve ion electrospray) 656 (MOAc⁻, 100%) |
| 132 | 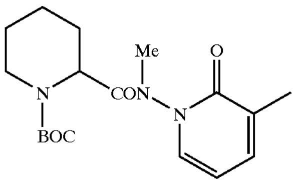 | 74 | (−ve ion electrospray) 740 (MOAc⁻, 100%) |
| 133 | 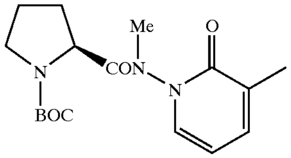 | 74 | |
| 134 | 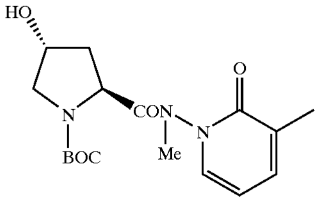 | 35 | |
| 135 | 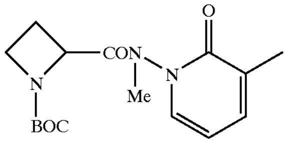 | 74 | (−ve ion electrospray) 712 (MOAc⁻, 100%) |
| 136 | 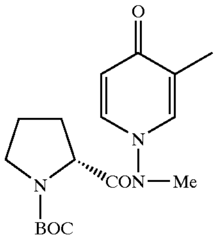 | 98 | (−ve ion electrospray) 726 (MOAc⁻, 100%) |

Step (c)
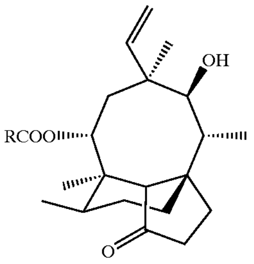
| Example No | R | yield (%) | MS m/z |
|---|---|---|---|
| 124 | 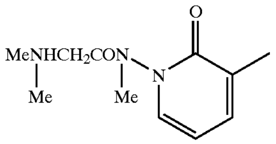 | 94 | (−ve ion chemical ionisation) 540 ([M−H]⁻, 100%) |
| 129 | 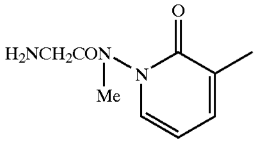 | 62 | (−ve ion electrospray) 526 ([M−H]⁻, 100%) |
| 132 | 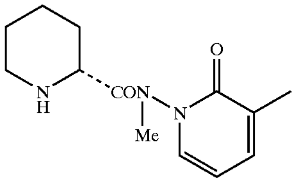 | 30 | (−ve ion electrospray) 580 ([M−H]⁻, 100%) |
| 133 | 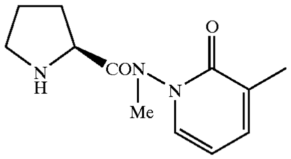 | 50 | (−ve ion electrospray) 566 ([M−H]⁻, 100%) |
| 134 | 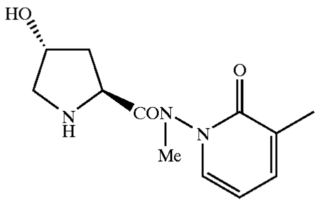 | 60 | (−ve ion electrospray) 582 ([M−H]⁻, 100%) |
| 135 | 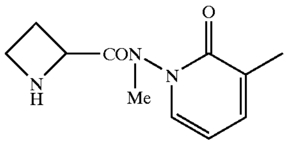 | 66 | (−ve ion electrospray) 552 ([M−H]⁻, 100%) |

-continued

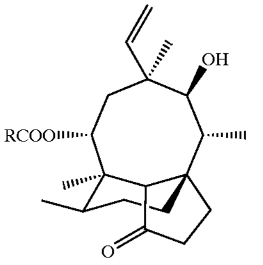

| Example No | R | yield (%) | MS m/z |
|---|---|---|---|
| 136 | 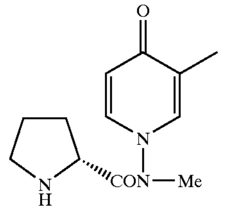 | 94 | (−ve ion electrospray) 566 ($[M-H]^-$, 100%) |

Example 140

{1-[N-Methyl-N-(N-methyl-(D)-prolyl)amino]-2-oxo-1,2-dihydropyridine-3-carboxylic acid}mutilin 14-ester

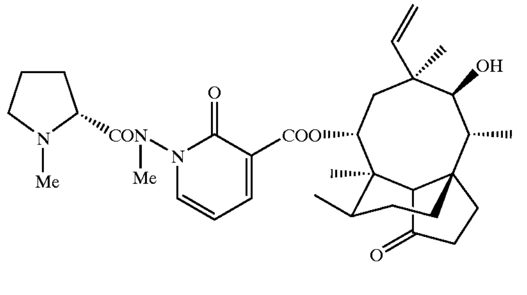

[1-(N-Methyl-N-(D)-prolylamino)-2-oxo-1,2-dihydropyridine-3-carboxylic acid]mutilin 14-ester was methylated by the procedure of Example 120 (step (b). Chromatography gave the title compound (48%). MS (+ve ion chemical ionisation), m/z 604 ($MNa^+$, 100%).

Example 141

(1-Methylamino-2-oxo-1,2-dihydropyridine-3-carboxylic acid)mutilin 14-ester

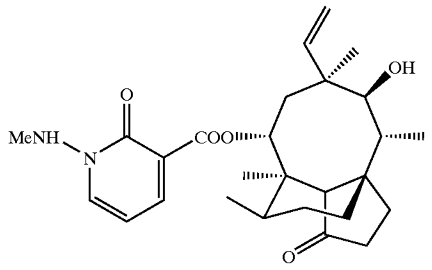

A solution of [1-(N-methyl-N-(D)-prolylamino)-2-oxo-1,2-dihydropyridine-3-carboxylic acid)mutilin 14-ester (65 mg) in dioxan (1 ml)/water (1 ml) was treated with 2N NaOH (0.2 ml) and heated at 60° C. for 16 hours. The mixture was partitioned between dichloromethane and water, the organic dried and evaporated. Chromatography gave the title compound (8 mg).

Example 142

{1-[N-(1,1-dioxothietane-3-carbonyl)-N-methylamino]-2-oxo-1,2-dihydropyridine-3-carboxylic acid}mutilin 14-ester

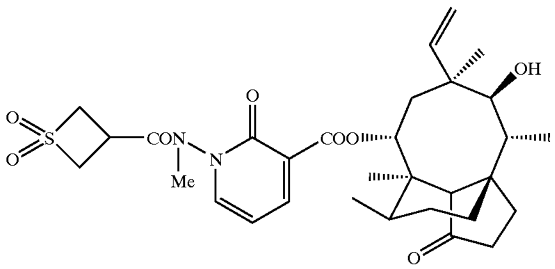

A solution of {1-[N-(thietane-3-carbonyl)-N-methylamino]-2-oxo-1,2-dihydropyridine-3-carboxylic acid}mutilin 14-ester (99 mg) in dichloromethane (4 ml) was treated with m-chloroperbenzoic acid (80 mg), stirred 1 hour, washed with aqueous $NaHCO_3$ (5 ml), dried and evaporated. Chromatography gave the title compound (48 mg). MS (+ve ion chemical ionisation) m/z 625 ($MNa^+$, 100%).

Example 143

(1-Formamido-2-oxo-1,2-dihydropyridine-3-carboxylic acid)mutilin 14-ester

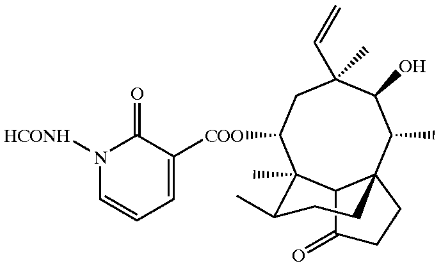

A solution of (1-amino-2-oxo-1,2-dihydropyridine-3-carboxylic acid)mutilin 14-ester (507 mg) in formic acid (10 ml) was treated at 0° C. with a prepared mixture of formic acid (20 ml) and acetic anhydride (20 ml) and stirred overnight at room temperature. Evaporation and chromatography gave title compound (100 mg). MS (−ve ion electrospray) m/z 483 ([M−H]$^-$, 100%).

Example 144

{1-[N-Formyl-N-(4-pyridylmethyl)amino]-2-oxo-1,2-dihydropyridine-3-carboxylic acid)mutilin 14-ester

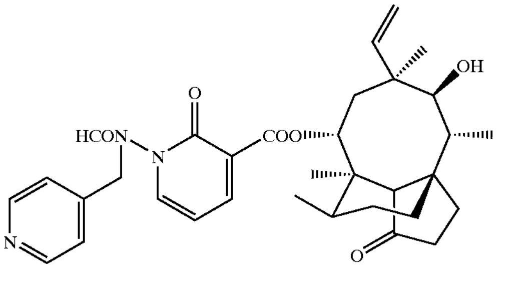

A solution of (1-formamido-2-oxo-1,2-dihydropyridine-3-carboxylic acid)mutilin 14-ester (100 mg) in DMF (4 ml) was treated with $K_2CO_3$ (200 mg) and 4-bromomethylpyridine (260 mg), stirred overnight and partitioned between water and dichloromethane (20 ml each). The aqueous was re-extracted with dichloromethane and the organic dried and evaporated. Purification by preparative HPLC gave the title compound (26 mg). MS (+ve ion electrospray) m/z 576 (MH$^+$, 40%), 231 (100%).

Example 145

[1-(N-Isonicotinoyl-N-methylamino)-2-oxo-1,2-dihydropyridine-3-carboxylic acid]mutilin 14-ester

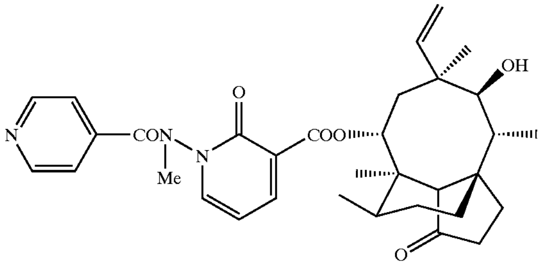

(a) [1-(N-isonicotinoylamino)-2-oxo-1,2-dihydropyridine-3-carboxylic acid]mutilin 14-ester—Isonicotinic acid (82 mg) in dichloromethane (4 ml) was treated with DMF (1 drop) and oxalyl chloride (0.15 ml), stirred 3 hours and evaporated to dryness. The resulting acid chloride was dissolved in pyridine (10 ml) and treated with a solution of (1-amino-2-oxo-1,2-dihydropyridine-3-carboxylic acid)mutilin 14-ester (200 mg) in pyridine (10 ml), stirred overnight and evaporated. Chromatography (dichloromethane/methanol) gave the title compound (20 mg).

(b) [1-(N-Isonicotinoyl-N-methylamino)-2-oxo-1,2-dihydropyridine-3-carboxylic acid]mutilin 14-ester—Material from step (a) was methylated by the procedure of Example 120 step (b) to give title compound (95%). MS (+ve ion electrospray), m/z 576 (MH$^+$, 40%), 274 (100%).

Example 146

(1-Acetamido-2-oxo-1,2-dihydropyridine-3-carboxylic acid)mutilin 14-ester

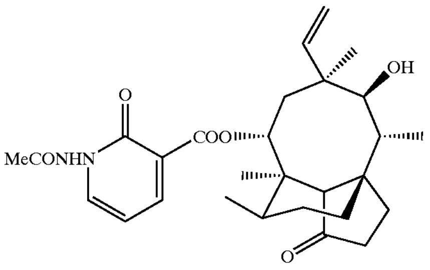

(a) (1-Diacetylamino-2-oxo-1,2-dihydropyridine-3-carboxylic acid)mutilin 14-ester—A solution of (1-amino-2-oxo-1,2-dihydropyridine-3-carboxylic acid)mutilin 14-ester (65 mg) in dichloromethane (2 ml) was treated with acetic anhydride (0.032 ml), pyridine (0.056 ml) and 4-dimethylaminopyridine (10 mg) and left overnight. The solution was diluted, washed with 2N HCl (5 ml), dried and evaporated. Chromatography gave title compound (36 mg).

(b) (1-Acetamido-2-oxo-1,2-dihydropyridine-3-carboxylic acid)mutilin 14-ester—Material from step (a) in dioxan (1 ml)/water (1 ml) was treated with 2N NaOH (0.033 ml), the solvent evaporated to dryness and the residue chromatographed to give title compound (6 mg).

Example 147

(4-Oxo-1-(D)-prolylamino-1,4-dihydropyrido[2,3-c]pyridazine-3-carboxylic acid)mutilin 14-ester

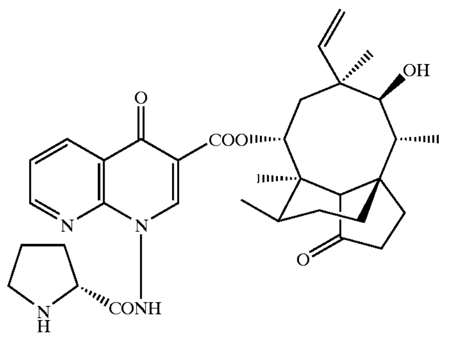

(4-Oxo-1-(D)-BOC-prolylamino-1,4-dihydropyrido[2,3-c]pyridazine-3-carboxylic acid)mutilin 14-ester (Example 139) was deprotected by the procedure of Example 121 step (c) to give title compound (87%). MS (−ve ion electrospray), m/z 604 ([M−H]$^-$, 100%).

Example 148

[1,6-Dihydro-1-(N-methyl-N-(L)-prolylamino)-6-oxopyridazine-5-carboxylic acid)mutilin 14-ester

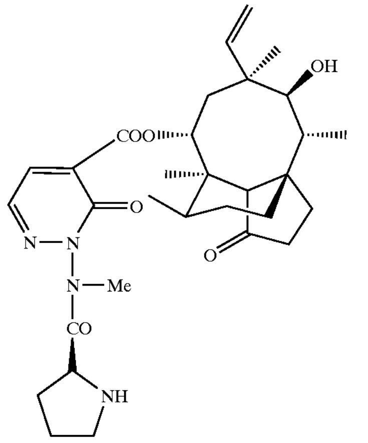

(a) [1,6-Dihydro-1-(N-methyl-N-BOC-(L)-prolylamino)-6-oxopyridazine-5-carboxylic acid]mutilin 14-ester—A solution of (1,6-Dihydro-1-methylamino-6-oxopyridazine-5-carboxylic acid)mutilin 14-ester (90 mg) in dichloromethane (1.3 ml)/DMF (1.3 ml) was ice-cooled, treated with BOC-(L)-proline (123 mg), pyridine (0.046 ml) and dicyclohexylcarbodiimide (180 mg) and stirred overnight. 4-Dimethylaminopyridine (20 mg) was added, the mixture stirred overnight and worked up according to Example 120 step (a) to give title compound (80 mg). MS (−ve ion electrospray) m/z 727 (MOAc$^-$, 100%), 667 ([M−H]$^-$, 10%).

(b) [1,6-Dihydro-1-(N-methyl-N-(L)-prolylamino)-6-oxopyridazine-5-carboxylic acid]mutilin 14-ester—Material from step (a) was deprotected by the procedure of Example 121 step (c) (100%). MS (+ve ion electrospray), m/z 569 (MH$^+$, 100%).

$^1$H NMR δ($d_6$-DMSO at 80° C.) inter alia 0.66 (3H, broad d, J 7.2 Hz), 0.88 (3H, d, J11 Hz), 1.11 (3H, s), 1.44 (3H, s), 2.42 (1H, broad s), 3.47 (1H, t, J10.4 Hz), 5.0–5.2 (2H, m), 5.78 (1H, d, J13.4 Hz), 6.21 (1H, dd, J28 and 18 Hz), 7.79 (1H, broad s), 8.02 (1H, broad s).

Example 149

[1,6-Dihydro-1-(N-methyl-N-(L)-trans-4-methoxyprolylamino)-6-oxopyridazine-5-carboxylic acid]mutilin 14-ester

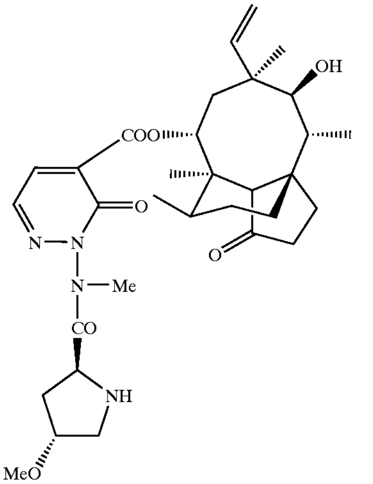

(a) [1,6-Dihydro-1-(N-methyl-N-BOC-(L)-trans-4-methoxyprolylamino)-6-oxopyridazine-5-carboxylic acid] mutilin 14-ester—BOC-(L)-trans-4-methoxyproline (D. J. Kyle and R. N. Hiner, PCT Int. Appl. (1992) WO9218155) was reacted by the procedure of Example 148 to give title compound (91%). MS (−ve ion electrospray) m/z 757 (MOAc$^-$, 100%).

(b) [1,6-Dihydro-1-(N-methyl-N-(L)-trans-4-methoxyprolylamino)-6-oxopyridazine-5-carboxylic acid] mutilin 14-ester—Material from step (a) was deprotected by the procedure of Example 121 step (c) (99%). MS (+ve ion electrospray) m/z 599 (MH$^+$, 100%).

Example 150

[1,6-Dihydro-1-(N-methyl-N-dimethylaminoacetylamino)-6-oxopyridazine-5-carboxylic acid]mutilin 14-ester

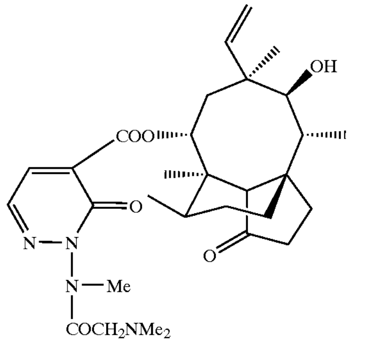

A solution of (1,6-dihydro-1-methylamino-6-oxopyridazine-5-carboxylic acid)mutilin 14-ester (160 mg) in dichloromethane (2 ml)/DMF (2 ml) was ice-cooled, treated with N,N-dimethylglycine (103 mg), 1-hydroxy-7-azabenzotriazole (136 mg) and dicyclohexylcarbodiimide (310 mg) and stirred 24 hours. The mixture was diluted with EtOAc (20 ml), washed with aqueous $NaHCO_3$ and water (2×20 ml), dried and evaporated. Chromatography ($CHCl_3$/MeOH/0.88$NH_3$ (aq)) gave title compound (150 mg). MS (+ve ion electrospray) m/z 557 ($MH^+$, 40%), 255 (100%).

Example 151

[1,6-Dihydro-1-(N-methyl-N-1-methyl-(L)-prolylamino)-6-oxopyridazine-5-carboxylic acid] mutilin 14-ester

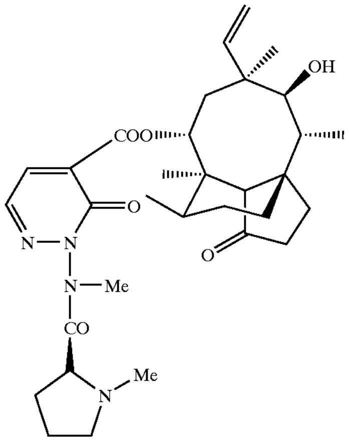

N-methyl-(L)-proline was reacted by the procedure of Example 150 to give title compound (55%). MS (+ve ion electrospray) m/z 605 ($MNa^+$, 100%), 583 ($MH^+$, 40%).

Example 152

(1-Methylamino-2-oxo-1,2-dihydropyrazine-3-carboxylic acid)mutilin 14-ester

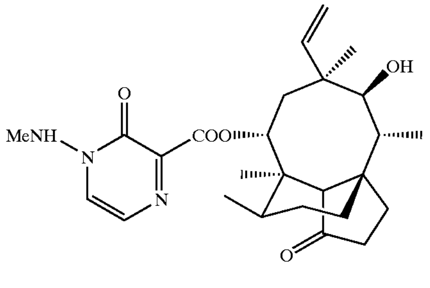

A solution of (2-oxo-1,2-dihydropyrazine-3-carboxylic acid)mutilin 14-ester (93 mg) in DMF (1.5 ml) was treated with $K_2CO_3$ (61 mg) and O-(2,4-dinitrophenyl)-N-methylhydroxylamine (94 mg), stirred overnight at room temperature then for 5 hours at 80° C. After partitioning between $CHCl_3$ and 2N NaOH solution, the organic solution was dried and evaporated to dryness. Chromatograpnhy gave title compound (19%). MS (+ve ion electrospray) m/z 494 (MNa+, 50%), 170 (100%).

Example 153

(1-Methoxycarbonylamino-4-oxo-1,4-dihydropyridine-3-carboxylic acid)mutilin 14-ester

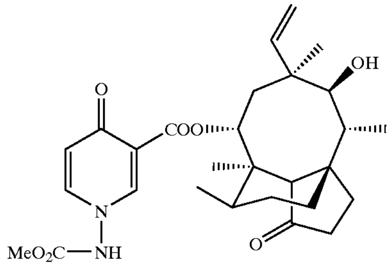

A solution of (1-amino-4-oxo-1,4-dihydropyridine-3-carboxylic acid)mutilin 14-ester (100 mg) in dichloromethane (20 ml) was treated with triethylamine (0.029 ml) and methyl chloroformate (0.017 ml), stirred 18 hours at room temperature, washed with aqueous $NaHCO_3$ (20 ml), dried and evaporated. Chromatography (EtOAc/hexane 1:1) gave title compound (20 mg). MS (−ve ion electrospray) m/z 513 ($[M-H]^-$, 35%).

Example 154

(1,4-Dihydro-1-formamido-4-oxoquinoline-3-carboxylic acid)mutilin 14-ester

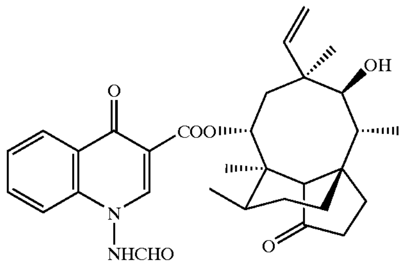

(1-Amino-4-oxo-1,4-dihydroquinoline-3-carboxylic acid) mutilin 14-ester was formylated by the procedure of Example 143 to give title compound (86%). MS (−ve ion electrospray) m/z 533 ($[M-H]^-$, 80%), 490 (100%).

Example 155

[1,4-Dihydro-1-(N-formyl-N-methylamino)-4-oxoquinoline-3-carboxylic acid)mutilin 14-ester

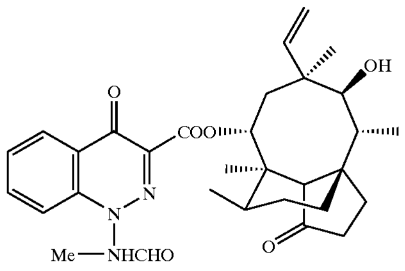

(1,4-Dihydro-1-formamido-4-oxoquinoline-3-carboxylic acid)mutilin 14-ester was methylated by the procedure of Example 120 step (b) to give title compound (36%). MS (+ve ion electrospray) m/z 571 ($MNa^+$, 35%), 310 (100%).

Example 156

[1-(3-Pyridylmethyleneamino)-2-oxo-1,2-dihydropyridine-3-carboxylic acid)mutilin 14-ester

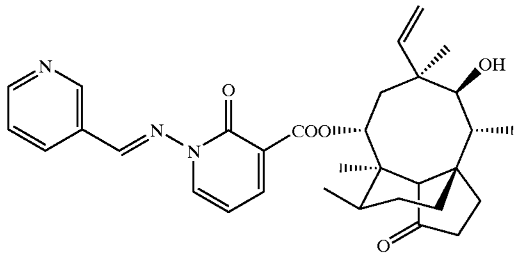

A solution of (1-amino-2-oxo-1,2-dihydropyridine-3-carboxylic acid)mutilin 14-ester (536 mg) in methanol (10 ml) was treated with HOAc (0.5 ml) and nicotinaldehyde (510 mg), refluxed 16 hours and evaporated. The residue was taken up in chloroform (20 ml), washed with water (20 ml), dried and evaporated. Chromatography gave the title compound (380 mg). MS (−ve ion electrospray) m/z 604 ($MOAc^-$, 100%).

Examples 157–164 were prepared by the procedure of Example 156.

3-(3-Pyridyl)propanal was prepared according to N. Adje, F. Vogeleisen and D. Uguen, *Tet. Lett.* (1996), 37(33), 5893–6. 2-Dimethylaminopyridine-5-carboxaldehyde was prepared according to I. Bennett, N. Broom, R. Cassels, J. Elder, N. D. Masson and P. O'Hanlon, *Bioorg and Med. Chem. Lett.* (1999), 9(13), 1847–1852.

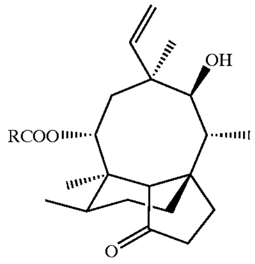

| Example No | R | yield (%) | MS m/z |
|---|---|---|---|
| 157 | 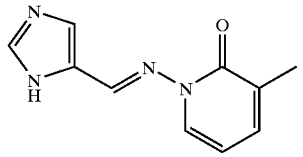 | 27 | (−ve ion electrospray) 533 ($[M-H]^-$, 100%) |
| 158 | 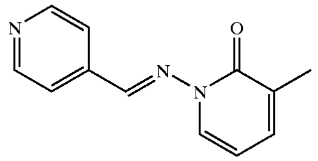 | 4 | (+ve ion chemical ionisation) 547 ($MH^+$, 100%) |
| 159 | 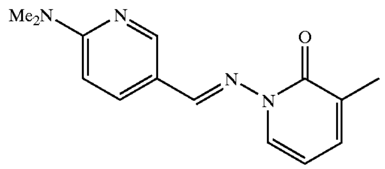 | 86 | (+ve ion chemical ionisation) 589 ($MH^+$, 100%) |

-continued
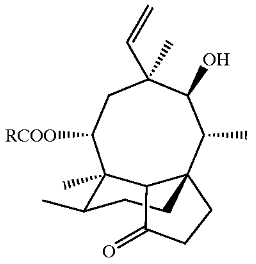
| Example No | R | yield (%) | MS m/z |
|---|---|---|---|
| 160 | 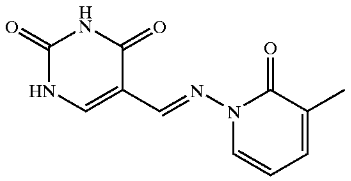 | 34 | (−ve ion electrospray) 577 ([M−H]$^-$, 100%) |
| 161 | 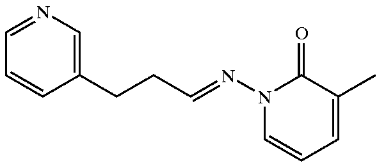 | 68 | (−ve ion electrospray) 572 ([M−H]$^-$, 100%) |
| 162 | 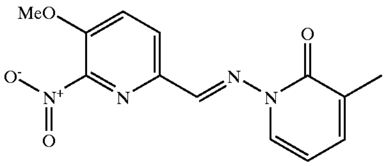 | 69 | |
| 163 | 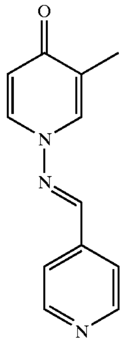 | 80 | (+ve ion electrospray) 568 (MNa$^+$, 45%), 244 (100%) |
| 164 | 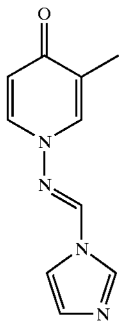 | 53 | (−ve ion electrospray) 547 ([M−H]$^-$, 100%) |

Example 165

[1-(3-Pyridylmethylamino)-2-oxo-1,2-dihydropyridine-3-carboxylic acid)mutilin 14-ester

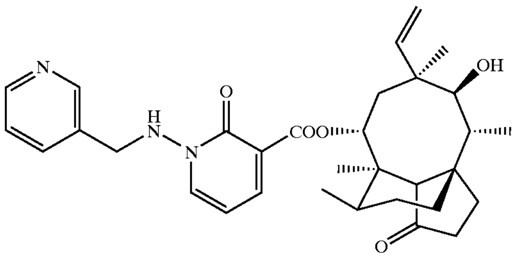

A solution of [1-(3-pyridylmethyleneamino)-2-oxo-1,2-dihydropyridine-3-carboxylic acid]mutilin 14-ester (88 mg) in methanol (2 ml) was treated with AcOH (0.04 ml) and sodium cyanoborohydride (20 mg), heated at 40° C. for 30 minutes and left 24 hours at room temperature. The mixture was diluted with dichloromethane (10 ml), washed with aqueous $NaHCO_3$ (10 ml), dried and evaporated. Chromatography (EtOAc) gave title compound (15 mg). MS (−ve ion electrospray), m/z 606 ($MOAc^-$, 100%).

Example 166

{1-[3-(3-Pyridyl)propylamino]-2-oxo-1,2-dihydropyridine-3-carboxylic acid}mutilin 14-ester

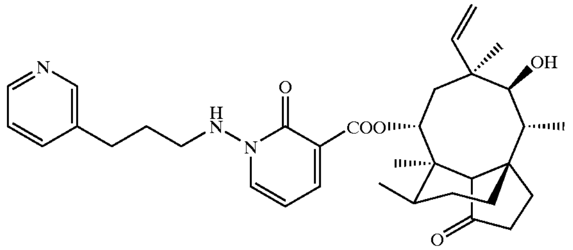

A solution of {1-[3-(3-pyridyl)propyleneamino]-2-oxo-1,2-dihydropyridine-3-carboxylic acid}mutilin 14-ester (120 mg) in MeOH (2 ml)/AcOH (2 ml) was treated with sodium cyanoborohydride (25 mg), stirred overnight and diluted with dichloromethane (20 ml). The mixture was washed with excess aqueous $NaHCO_3$, dried and evaporated to give title compound (102 mg). MS (+ve ion electrospray), m/z 598 ($MNa^+$, 100%).

Example 167

{1-[N-Methyl-N-3-(3-pyridyl)propylamino]-2-oxo-1,2-dihydropyridine-3-carboxylic acid}mutilin 14-ester

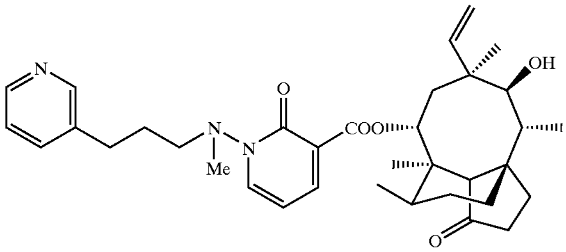

The product from Example 166 was methylated by the procedure of Example 120 step (b) and purified by preparative HPLC to give title compound (31%). MS (+ve ion electrospray) m/z 590 ($MH^+$, 100%).

Example 168

[1-(6-Dimethylamino-3-pyridylmethylamino)-2-oxo-1,2-dihydropyridine-3-carboxylic acid]mutilin 14-ester

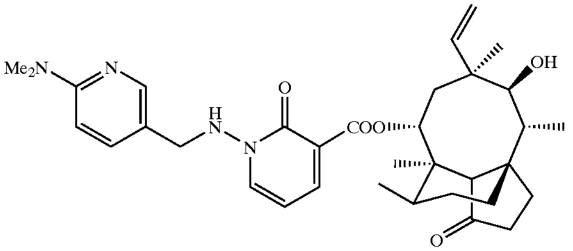

A solution of [1-(6-dimethylamino-3-pyridylmethyleneamino)-2-oxo-1,2-dihydropyridine-3-carboxylic acid]mutilin 14-ester (206 mg) in MeOH (20 ml) with 10% Pd/C (50 mg) was stirred under $H_2$ at atmospheric pressure for 6 hours, filtered through kieselguhr and evaporated. Chromatography gave the title compound (64 mg). MS (+ve ion chemical ionisation), m/z 591 ($MH^+$, 100%).

Example 169

[1-(2-Amino-3-methoxy-6-pyridylmethylamino)-2-oxo-1,2-dihydropyridine-3-carboxylic acid]mutilin 14-ester

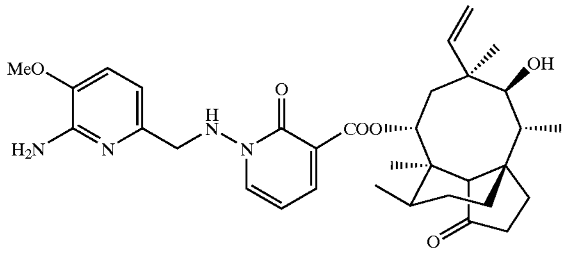

The title compound was produced from [1-(3-methoxy-2-nitro-6-pyridylmethyleneamino)-2-oxo-1,2- dihydropyridine-3-carboxylic acid]mutilin 14-ester (Example 162) by the procedure of Example 168 (16%). MS (+ve ion chemical ionisation) m/z 615 ($MNa^+$, 100%).

Biological Data

Compounds of the present invention were assessed for anti-bacterial activity in a conventional MIC assay against a range of pathogenic organisms.

The compounds of Examples 1 to 169 were found to have MICs ≦4 ug/ml against *Staphylococcus aureus* Oxford, *Streptococcus pneumoniae* 1629 and *Moraxella catarrhalis* Ravasio.

What is claimed is:

1. A compound of formula (IA) or (IB):

(IA)

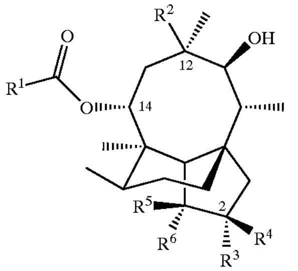

(IB)

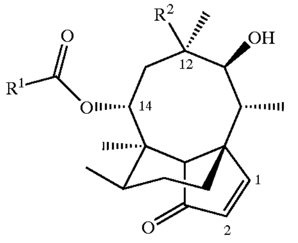

in which:

$R^1$ is:

a 5- or 6-membered aromatic or heteroaromatic ring attached via a ring carbon atom and having a substituent selected from halo, $R^7O$—, $R^7S$— or $R^8R^9N$— on a ring carbon adjacent to the carbon of attachment; or a 5- or 6-membered dihydro heteroaromatic ring attached via a ring carbon atom and having one oxygen or one or two nitrogen atoms and optionally fused to phenyl, a 5- or 6-membered heteroaryl ring having one or two nitrogen atoms or a 5- or 6-membered heterocyclyl ring having a sulphur, oxygen or nitrogen atom and further having a substituent selected from oxo or thioxo on a ring carbon adjacent to the carbon of attachment;

a 6-membered tetrahydro heteroaromatic ring attached via a ring carbon atom having one or two nitrogen atoms and further having two substituents independently selected from oxo or thioxo wherein one of the substituents is on a ring carbon adjacent to the carbon of attachment; or a bicyclic heteroaryl ring attached via a ring carbon atom and having nine or ten ring atoms and from one to four nitrogen atoms;

wherein the ring of $R^1$ may be optionally further substituted;

$R^2$ is vinyl or ethyl;

$R^3$ is H, OH or F and $R^4$ is H, or $R^3$ is H and $R^4$ is F and $R^5$ and $R^6$ together form an oxo group; or $R^3$ and $R^4$ is each H and $R^5$ is H, or OH and $R^6$ is H or $R^5$ is H and $R^6$ is H or OH;

$R^7$ is optionally substituted $C_{(1-6)}$alkyl; and $R^8$ and $R^9$ are independently selected from hydrogen or optionally substituted $C_{(1-6)}$alkyl.

2. A compound as claimed in claim 1 in which the ring in $R^1$ is selected from pyrazole, pyrazine, pyridine, pyrimidine, and pyran which may be optionally fused with a 6 membered aromatic or non-aromatic ring, optionally containing up to two nitrogen atoms.

3. A compound as claimed in claim 1 in which the ring in $R^1$ is selected from:

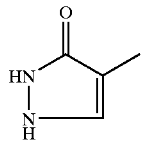
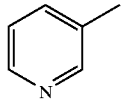
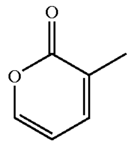
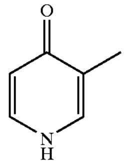
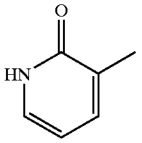
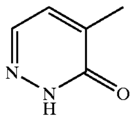
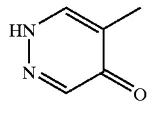
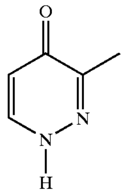
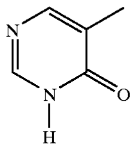
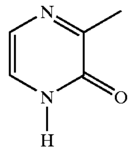
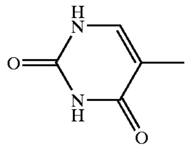
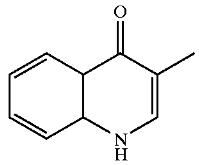
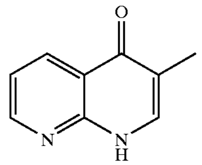
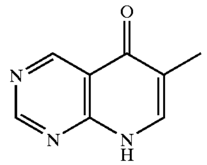
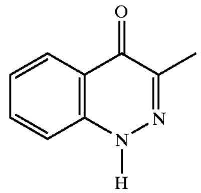
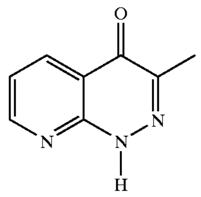
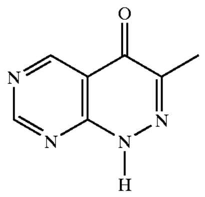
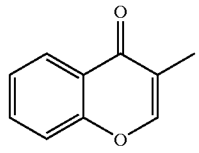
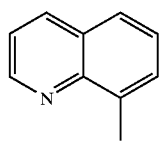

-continued

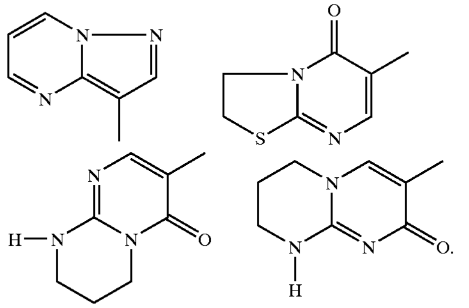

4. A compound as claimed in claim 1 in which the ring for $R^1$ is selected from:

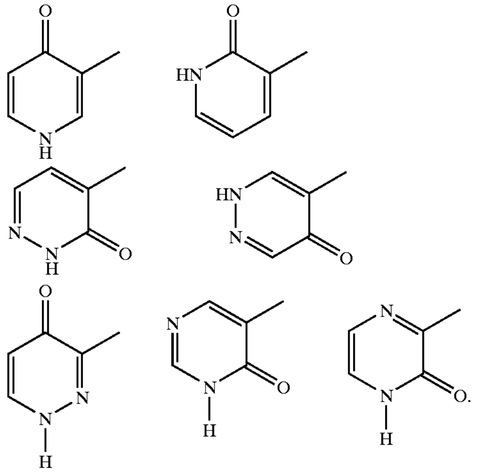

5. A compound as claimed in claim 1 in which the ring of $R^1$ is selected from:

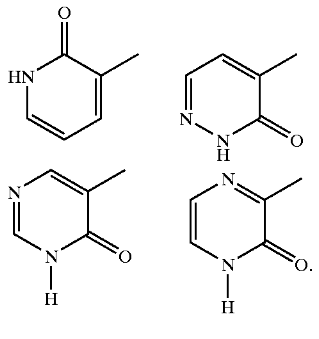

6. A compound as claimed in claim 1 in which a substituent for a carbon atom of a ring in $R^1$ is selected from $(C_{1-6})$alkyl, $(C_{1-6})$alkylthio, amino, mono- and di-N-$(C_{1-6})$ alkylamino, $R^{10}(C_{1-6})$alkylamino, imidazolinyl, piperidinyl, piperazinyl (optionally substituted on N by $R^{11}$), pyridyl, hydrazino, N-$(C_{1-3})$alkylhydrazino, aminomethylcarbonylhydrazino, heterocyclyl$(C_{1-3})$alkyl in which heterocyclyl comprises a 6-membered ring with 1 nitrogen atom and optionally an oxygen or a second nitrogen, and in which:

$R^{10}$ is hydroxy, amino, heteroaryl in which heteroaryl comprises a 5 or 6-membered ring with 1 or 2 nitrogen atoms, heterocyclyl in which heterocyclyl comprises a 6-membered ring with 1 nitrogen atom and optionally an oxygen or a second nitrogen, $R^{11}$-amino, in which:

$R^{11}$ is $(C_{1-3})$alkyl, hydroxy$(C_{1-3})$alkyl, carbamoyl, methylsulfonyl, or amino$(C_{1-3})$alkylcarbonyl.

7. A compound as claimed in claim 1 in which a substituent for a nitrogen atom of a ring in $R^1$ is selected from $R^{12}(C_{1-6})$alkyl, amino, mono- or di-$(C_{1-6})$alkylamino, N-(pyridyl$(C_{1-3})$alkyl)-N-$(C_{1-3})$alkylamino (in which pyridyl is optionally substituted by $(C_{1-6})$alkoxy and/or amino, mono- or di-$(C_{1-6})$alkylamino), acyl- or sulfonyl amino, acyl- or sulfonyl-mono$(C_{1-6})$alkylamino, optionally substituted phenyl, $R^{13}$C=N—, $R^{14}(C_{1-4})$alkylN(H/Me)-, $R^{15}$CON(H/Me)- and $R^{16}$N(CHO)—, in which:

$R^{12}$ is hydrogen, halo, nitrilo, amino, $(C_{1-6})$alkoxy, $(C_{1-3})$alkoxy$(C_{1-6})$alkoxy, $(C_{1-6})$alkylcarboxy, $(C_{1-6})$ alkoxy, heteroaryl, heteroarylcarbonyl, imidazolylthio, heterocyclyl, optionally substituted phenyl;

$R^{13}$ is $(C_{0-4})$alkylheteroaryl in which the heteroaryl ring is 5- or 6-membered and has 1 or 2 nitrogen atoms and which may be substituted by 1 or 2 substituents, chosen from: $(C_{1-6})$alkoxy, nitro, amino, $(C_{16})$alkylamino, di-$(C_{1-6})$alkylamino, or oxo;

$R^{14}$ is $(C_{1-4})$alkylheteroaryl in which the heteroaryl ring is 5 or 6 membered and has 1 or 2 nitrogen atoms, and which may be substituted by 1 or 2 substituents, chosen from: $(C_{1-6})$alkoxy, nitro, amino, $(C_{1-6})$alkylamino, di-$(C_{1-6})$alkylamino, or oxo;

$R^{15}$ is $(C_{1-6})$alkyl, $(C_{1-6})$alkoxy, aminomethyl, mono or dialkyl$(C_{1-6})$aminomethyl, a 4, 5 or 6 membered heterocyclic ring comprising a heteroatom selected from NH, NMe, and, for pyrrolidine, optionally substituted by hydroxy or methoxy, dioxothietane, imidazole, pyridine, pyridazine, pyrimidine, or pyrazine; and $R^{16}$ is hydrogen, $(C_{1-6})$alkyl, benzyl or pyridinylmethyl.

8. A compound as claimed in claim 1 in which $R^1$ is selected from:

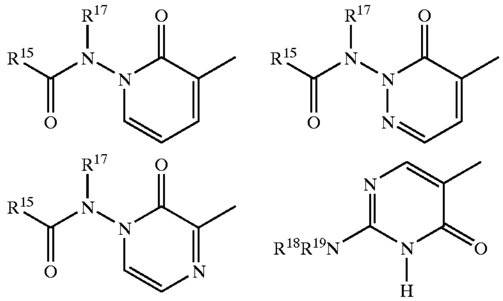

in which:

$R^{15}$ is $(C_{1-6})$alkyl, $(C_{1-6})$alkoxy, aminomethyl, mono or dialkyl$(C_{1-6})$aminomethyl, a 4, 5 or 6 membered heterocyclic ring comprising a heteroatom selected from NH, NMe, and, for pyrrolidine, optionally substituted by hydroxy or methoxy, dioxothietane, imidazole, pyridine, pyridazine, pyrimidine, or pyrazine;

$R^{17}$ is hydrogen or $(C_{1-6})$alkyl;

$R^{18}$ is $R^{10}(C_{1-6})$alkyl, and $R^{19}$ is hydrogen, or $R^{18}R^{19}$N— form a piperazinyl ring optionally substituted on N by $R^{11}$, in which:

$R^{10}$ is hydroxy, amino, heteroaryl$(C_{1-3})$alkyl in which heteroaryl comprises a 5 or 6-membered ring with 1 or 2 nitrogen atoms, heterocyclyl$(C_{1-3})$alkyl in which heterocyclyl comprises a 6-membered ring with 1 nitrogen atom and optionally an oxygen or a second nitrogen, or $R^{11}$-amino, in which:

$R^{11}$ is $(C_{1-3})$alkyl, hydroxy$(C_{1-3})$alkyl, carbamoyl, methylsulfonyl, or amino$(C_{1-3})$alkylcarbonyl.

9. A compound as claimed in claim 8 in which moiety $R^{15}NCO$ is derived from (D)- or (L)-proline.

10. A compound as claimes in claim 1 in which $R^3$ and $R^4$ are both hydrogen, and $R^5$ and $R^6$ together form an oxo group.

11. A compound according to claim 1 selected from:

(4-Oxo-6,7,8,9-tetrahydro-4H-pyrimido[1,2-a] pyrimidine-3-carboxylic acid) mutilin 14-ester;

[2-(3-Morpholino-propylamino)-6-oxo-1,6-dihydro-pyrimidine-5-carboxylic acid) mutilin 14-ester;

(8-Ethyl-2-piperazin-1-yl-5-oxo-5,8-dihydro-pyrido[2,3-d]pyrimidine-6-carboxylic acid) mutilin 14-ester;

{1,6-Dihydro-1-[N-methyl-N-(D)-prolylamino]-6-oxo-pyridazine-5-carboxylic acid} mutilin 14-ester;

{1,2-Dihydro-1-[N-methyl-N-(D)-prolylamino]-2-oxo-pyridine-3-carboxylic acid} mutilin 14-ester;

{1,6-Dihydro-1-[N-methyl-N-(L)-prolylamino]-6-oxo-pyridazine-5-carboxylic acid} mutilin 14-ester; and {1,6-Dihydro-1-[N-methyl-N-(L)-trans-methoxy-prolylamino]-6-oxo-pyridazine-5-carboxylic acid} mutilin 14-ester.

12. A method of preparing a compound of formula (IA) or (IB) according to claim 1 which comprises reacting a compound of formula (IIA) or (IIB):

(IIA)

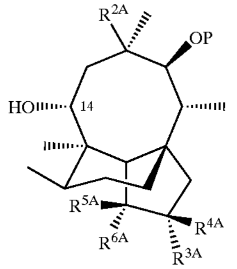

(IIB)

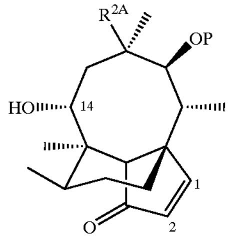

in which:

P is hydrogen or an hydroxy-protecting group;

$R^{2A}$, $R^{3A}$, $R^{4A}$, $R^{5A}$ and $R^{6A}$ are $R^2$, $R^3$, $R^4$, $R^5$ and $R^6$ as defined for formulae (IA) and (IB) or a group convertible to $R^2$, $R^3$, $R^4$, $R^5$ and $R^6$ respectively; and is as hereinbefore defined;

with a compound of formula (III):

(III)

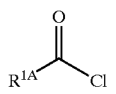

in which:

$R^{1A}$ is $R^1$ as defined for formulae (IA) and (IB) or a group convertible to $R^1$;

in an esterification reaction and thereafter, and if so needed;

converting P to hydrogen, and if necessary converting an $R^{2A}$, $R^{3A}$, $R^{4A}$, $R^{5A}$ and $R^{6A}$ group to an $R^2$, $R^3$, $R^4$, $R^5$ and $R^6$ group.

13. A pharmaceutical composition comprising a compound according to claim 1, and a pharmaceutically acceptable carrier or excipient.

14. A method of treating microbial infections in humans and in domesticated mammals, which comprises administering a compound according to claim 1, to a patient in need thereof.

15. A method of treating recurrent otitis media or recurrent acute bacterial sinusitis in humans, which comprises nasally administering a compound according to claim 1, to a patient in need thereof.

16. A method of treatment of skin and soft tissue infections and in the treatment of acne in humans, which comprises topically administering a compound according to claim 1, to a patient in need thereof.

17. A compound of formula (IA) or (IB):

(IA)

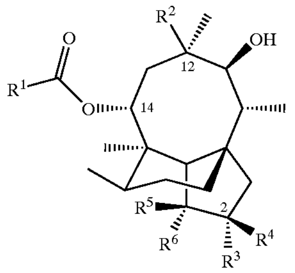

(IB)

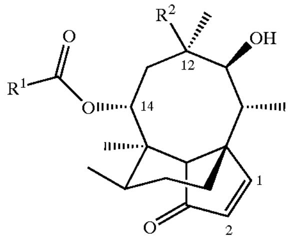

in which:

$R^1$ is:

a 5- or 6-membered aromatic or heteroaromatic ring attached via a ring carbon atom and containing a substituent selected from $R^7O$—, $R^7S$— or $R^8R^9N$— on a ring carbon adjacent to the carbon of attachment; or a 5- or 6-membered dihydro heteroaromatic ring attached via a ring carbon atom and containing a substituent selected from oxo or thioxo on a ring carbon adjacent to the carbon of attachment; or a 6-membered tetrahydro heteroaromatic ring attached via a ring carbon atom and containing two substituents independently selected from oxo or thioxo wherein one of the substituents is on a ring carbon adjacent to the carbon of attachment;

wherein the ring of $R^1$ may be optionally further substituted and/or may be fused to a second optionally substituted 5, 6, or 7 membered aromatic or non-aromatic ring, optionally containing up to four heteroatoms, each of which is selected from oxygen, nitrogen and sulphur;

$R^2$ is vinyl or ethyl;

$R^3$ is H, OH or F; and $R^4$ is H; or $R^3$ is H and $R^4$ is F;

$R^5$ is OH or H and $R^6$ is H; or $R^5$ is H and $R^6$ is OH or H; or $R^5$ and $R^6$ together form an oxo group;

$R^7$ is optionally substituted alkyl;

$R^8$ and $R^9$ are independently selected from hydrogen or optionally substituted alkyl; or $R^7$, $R^8$ or $R^9$, together with the atom to which they are attached, may form a second aromatic or non-aromatic ring fused to $R^1$.

18. A compound according to claim 17 in which $R^1$ is 4-substituted-quinolin-3-yl, 2-substituted-pyridin-3-yl, quinolin-8-yl, pyrazolo[1,5-a]pyrimidin-3-yl, 4-oxo-1,4-dihydro-quinolin-3-yl, 2-oxo-1,2-dihydro-pyridin-3-yl, 4-oxo-4-H-chromen-3-yl, 6-oxo-1,6-dihydro-pyridazin-5-yl, 2,4-dioxo-1,2,3,4-tetrahydro-pyrimidin-5-yl, 4-oxo-3,4-dihydro-pyrimidin-5-yl, 4-oxo-1,4-dihydro-[1,8]naphthyridin-3-yl, and 5-oxo-2,3-dihydro-5-H-thiazolo[3,2-a]pyrimidin-6-yl, all of which may be optionally substituted.

19. A compound according to claim 17 in which $R^1$ is a 6-membered dihydro or tetrahydro heteroaromatic ring with an oxo substituent adjacent to the atom of attachment which rings may be optionally further substituted.

20. A compound according to claim 17 in which $R^1$ is optionally substituted 2-pyridone or 4-pyridone.

* * * * *